United States Patent [19]
Lu et al.

[11] Patent Number: 5,792,769
[45] Date of Patent: Aug. 11, 1998

[54] GUANIDINO PROTEASE INHIBITORS

[75] Inventors: Tianbao Lu, Exton; Carl R. Illig, Phoenixville; Bruce E. Tomczuk, Collegeville, all of Pa.; Richard M. Soll, Lawrenceville, N.J.; Nalin L. Subasinghe, West Chester, Pa.; Roger F. Bone, Bridgewater, N.J.

[73] Assignee: 3-Dimensional Pharmaceuticals, Inc., Exton, Pa.

[21] Appl. No.: 698,401

[22] Filed: Aug. 15, 1996

Related U.S. Application Data

[63] Continuation-in-part of Ser. No. 536,939, Sep. 29, 1995, abandoned.

[51] Int. Cl.$^6$ .......................... A61K 31/445; C07F 9/06; C07D 241/04; C07C 279/00
[52] U.S. Cl. .................... 514/255; 514/317; 514/330; 514/331; 514/603; 514/604; 514/634; 514/822; 544/398; 544/399; 544/400; 544/402; 546/21; 546/229; 546/230; 546/231; 564/237
[58] Field of Search .................................... 514/330, 255, 514/317, 331, 603, 604, 634, 822; 546/21, 229, 230, 231; 564/237; 544/398, 399, 400, 402

[56] References Cited

U.S. PATENT DOCUMENTS

| | | | |
|---|---|---|---|
| 3,577,432 | 5/1971 | Hesley | 260/326.3 |
| 4,433,152 | 2/1984 | Muramatsu et al. | 546/193 |
| 5,260,307 | 11/1993 | Ackermann et al. | 514/323 |
| 5,466,811 | 11/1995 | Alexander | 546/283 |

FOREIGN PATENT DOCUMENTS

| | | |
|---|---|---|
| 0 372 486 | 6/1990 | European Pat. Off. . |
| 0 559 046 | 9/1993 | European Pat. Off. . |
| 50-140474 | 11/1975 | Japan . |
| 51-75042 | 6/1976 | Japan . |
| 58-194861 | 11/1983 | Japan . |
| WO 94/20467 | 9/1994 | WIPO . |
| WO 96/06832 | 3/1996 | WIPO . |
| WO 96/06849 | 3/1996 | WIPO . |

OTHER PUBLICATIONS

Benkert, B. et al., "Relations between structure and the noradrenaline depleting effects of guanidine and amidine derivatives," Chem. Abstr. 83:188217s (1975).

Brzozowski, Z., "Derivatives of 2–mercaptobenzenesulfonamide. I. Synthesis of some S– and N–substituted derivatives of 4–chloro–2–mercapto–5–methylbenzenesulfonamide," Acta. Pol. Pharm 44(6):486–490 (1987).

Jameson, G. W. and D. T. Elmore, "Affinity Chromatography of Bovine Trypsin. A Rapid Separation of Bovine α–and β Trypsin," Biochem. J. 41:555–565 (1974).

Lespagnol, A. et al., "Investigation of the series of diuretic sulfonamide derivatives," Chem. Abstr. 63:525 (1965).

Miyamoto, S. and M. Kojima, "$N^4$–(ω–Guanidinoalkanoyl)sulfanilamides," Chem. Abstr. 85:159726t (1976), English abstract of JP 51–75042 (Doc. AM1).

Nippon Chemifar Co., Ltd., "Piperidine Derivatives," Chem. Abst. 101:38355m (1984), English abstract of JP 58–194861 (Doc. AN1).

Protiva, M. et al., "Hypotensive 1–benzyl–4– guanylpiperazines," Chem. Abstr. 82:140187j (1975).

Ryznerski, Z. et al., "Synthesis and Pharmacological Properties of Phenoxylethypiperazine Derivatives," Pol. J. Pharmacol. Pharm. 41:191–199 (1989).

Saulnier, M. G. et al., "An Efficient Method for the Synthesis of Guanidino Prodrugs," Bioorgan. Med. Chem. Letts. 4(16):1985–1990 (Aug. 1994).

Somorin, O. and L. Ameghashitsi, "Synthesis of New Arginine Derivatives as Substrates of Trypsin," Bull. Chem. Soc. Jpn. 59:1593–1595 (1986).

Takahashi, T. and H. Sugimoto, "Quinazoline compounds," Chem. Abstr. 85:46769 (1976), English abstract of JP 50–140474 (Doc. AL1).

Primary Examiner—C. Warren Ivy
Assistant Examiner—Raymond Covington
Attorney, Agent, or Firm—Sterne, Kessler Goldstein & Fox P.L.L.C.

[57] ABSTRACT

Compounds of the formula:

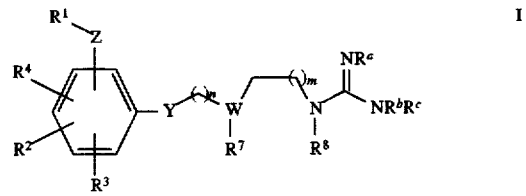

wherein $R^1$—$R^4$, $R^7$—$R^8$, $R^a$, $R^b$, $R^c$, Y, Z, n and m are set forth in the specification, as well as hydrates, solvates or pharmaceutically acceptable salts thereof, that inhibit a number of proteolytic enzymes are described. Also described are methods for preparing the compounds of Formula I.

49 Claims, No Drawings

GUANIDINO PROTEASE INHIBITORS

This application is a continuation-in-part of application Ser. No. 08/536,939, filed Sep. 29, 1995 now abandoned, the contents of which are fully incorporated by reference herein.

BACKGROUND OF THE INVENTION

1. Field of the Invention

The present invention relates to novel compounds that function as enzyme inhibitors, and particularly to a new class of non-peptidic inhibitors of proteolytic enzymes.

2. Related Art

Proteases are enzymes that cleave proteins at single, specific peptide bonds. Proteases can be classified into four generic classes: serine, thiol or cysteinyl, acid or aspartyl, and metalloproteases (Cuypers et al., *J. Biol. Chem.* 257:7086 (1982)). Proteases are essential to a variety of biological activities, such as digestion, formation and dissolution of blood clots, reproduction and the immune reaction to foreign cells and organisms. Aberrant proteolysis is associated with a number of disease states in man and other mammals. The human neutrophil proteases, elastase and cathepsin G, have been implicated as contributing to disease states marked by tissue destruction. These disease states include emphysema, rheumatoid arthritis, corneal ulcers and glomerular nephritis. (Barret, in *Enzyme Inhibitors as Drugs*, Sandler, ed., University Park Press, Baltimore, (1980)). Additional proteases such as plasmin, C-1 esterase, C-3 convertase, urokinase, plasminogen activator, acrosin, and kallikreins play key roles in normal biological functions of mammals. In many instances, it is beneficial to disrupt the function of one or more proteolytic enzymes in the course of therapeutically treating a mammal.

Serine proteases include such enzymes as elastase (human leukocyte), cathepsin G, plasmin, C-1 esterase, C-3 convertase, urokinase, plasminogen activator, acrosin, chymotrypsin, trypsin, thrombin, factor Xa and kallikreins.

Human leukocyte elastase is released by polymorphonuclear leukocytes at sites of inflammation and thus is a contributing cause for a number of disease states. Cathepsin G is another human neutrophil serine protease. Compounds with the ability to inhibit the activity of these enzymes are expected to have an anti-inflammatory effect useful in the treatment of gout, rheumatoid arthritis and other inflammatory diseases, and in the treatment of (emphysema. Chymotrypsin and trypsin are digestive enzymes. Inhibitors of these enzymes are useful in treating pancreatitis. Inhibitors of urokinase and plasminogen activator are useful in treating excessive cell growth disease states, such as benign prostatic hypertrophy, prostatic carcinoma and psoriasis.

The serine protease thrombin occupies a central role in hemostasis and thrombosis, and as a multifactorial protein, induces a number of effects on platelets, endothelial cells, smooth muscle cells, leukocytes, the heart, and neurons (Tapparelli et al., *Trends in Pharmacological Sciences* 14:366–376 (1993); Lefkovits and Topol, *Circulation* 90(3):1522–1536 (1994); Harker, *Blood Coagulation and Fibrinolysis* 5 (*Suppl* 1):S47–S58 (1994)). Activation of the coagulation cascade through either the intrinsic pathway (contact activation) or the extrinsic pathway (activation by exposure of plasma to a non-endothelial surface, damage to vessel walls or tissue factor release) leads to a series of biochemical events that converge on thrombin. Thrombin cleaves fibrinogen ultimately leading to a hemostatic plug (clot formation), potently activates platelets through a unique proteolytic cleavage of the cell surface thrombin receptor (Coughlin, *Seminars in Hematology* 31(4):270–277 (1994)), and autoamplifies its own production through a feedback mechanism. Thus, inhibitors of thrombin function have therapeutic potential in a host of cardiovascular and non-cardiovascular diseases, including: myocardial infarction; unstable angina; stroke; restenosis; deep vein thrombosis; disseminated intravascular coagulation caused by trauma, sepsis or tumor metastasis; hemodialysis; cardiopulmonary bypass surgery; adult respiratory distress syndrome; endotoxic shock; rheumatoid arthritis; ulcerative colitis; induration; metastasis; hypercoagulability during chemotherapy; Alzheimer's disease; and Down's syndrome.

Factor Xa is another serine protease in the coagulation pathway. Factor Xa associates with factor Va and calcium on a phospholipid membrane thereby forming a prothrombinase complex. This prothrombinase complex then converts prothrombin to thrombin (Claeson, *Blood Coagulation and Fibrinolysis* 5:411–436 (1994); Harker, *Blood Coagulation and Fibrinolysis* 5 (*Suppl* 1):S47–S58 (1994)). Inhibitors of factor Xa are thought to offer an advantage over agents that directly inhibit thrombin since direct thrombin inhibitors still permit significant new thrombin generation (Lefkovits and Topol, *Circulation* 90(3):1522–1536 (1994); Harker, *Blood Coagulation and Fibrinolysis* 5 (*Suppl* 1):S47–S58 (1994)).

A need continues to exist for non-peptidic compounds that are potent and selective protease inhibitors, and which possess greater bioavailability and fewer side-effects than currently available protease inhibitors. Accordingly, new classes of potent protease inhibitors, characterized by potent inhibitory capacity and low mammalian toxicity, are potentially valuable therapeutic agents for a variety of conditions, including treatment of a number of mammalian proteolytic disease states.

U.S. Pat. No. 5,260,307, issued Nov. 9, 1993, discloses amidinopiperidine compounds that inhibit thrombin-induced platelet aggregation and clotting of fibrinogen in plasma. See, for example, column 5, lines 11–63 and column 9, lines 13–16.

European patent application EP 559046, published Sep. 8, 1993, discloses guanidine derivatives having specificity for the inhibition of thrombin. The compounds are useful for inhibiting platelet aggregation induced by thrombin and thrombin-induced clotting of fibrinogen in blood plasma.

PCT International application WO 94/20467, published Sep. 15, 1994, discloses 4-aminopyridine derivatives that also include an aryl ether or arylamino moiety. The compounds are useful for inhibiting thrombin.

U.S. Pat. No. 4,433,152, issued Feb. 21, 1984, discloses 1-piperidinecarboxamidines having the formula:

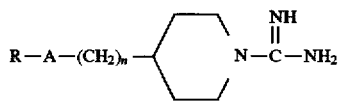

including compounds where n is 0–3, A is oxygen or sulfur, and R is phenyl substituted with alkoxy, sulfamoyl (—SO$_2$NH—) or benzyl. See column 2, lines 4–36. The patent discloses that these compounds can be employed to inhibit a complement reaction, inflammation caused by an allergic reaction, and platelet aggregation.

Laid-open application Jpn. Kokai Tokkyo Koho JP 58194861 A2, published Nov. 12, 1983, discloses preparation of piperidine derivatives by reaction of 1-amidino-4-piperidinepropionic acid or its reactive derivatives with 2,4-RR₁C₆H₃OH, optionally followed by deprotection. Thus, compounds were formed having the formula:

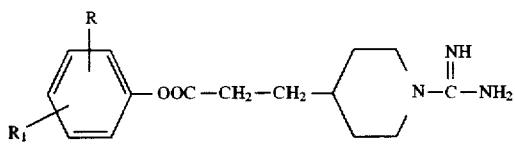

where R can be methoxy and R₁ can be 2-propenyl. Platelet aggregation inhibitory activity was shown in rabbit platelet-rich plasma.

U.S. Pat. No. 3,577,432, patented May 4, 1971, discloses 1-substituted-3-phenoxypyrrolidines and their salts. One compound disclosed therein has the formula:

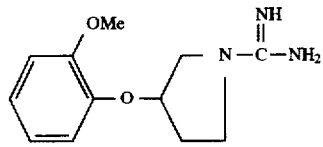

The patent discloses that the compounds and their salts can be employed as tranquilizers, muscle relaxants and anticonvulsants.

Chemical Abstracts 82:140187 (1974) discloses hemisulfate salts of 1-benzyl-4-guanylpiperazines wherein the phenyl ring is optionally substituted with Me, Cl, OMe, SMe and SPh. The compounds are alleged to have hypotensive, antiarrhythmic, local anesthetic, spasmolytic, myorelaxant, and central depressant activity.

Chemical Abstracts 83:188217 (1975) reports that 2-(2-methoxyphenoxy)ethylguanidine was the most potent compound among a series of 24 guanidine and amidine derivatives in depleting noradrenaline in sympathetic nerve terminals of the guinea pig heart in vivo.

Laid-open application Jpn. Kokai Tokkyo Koho JP 50 140474 A, published Nov. 11, 1975 discloses the following N-amidinodiazepine derivatives including:

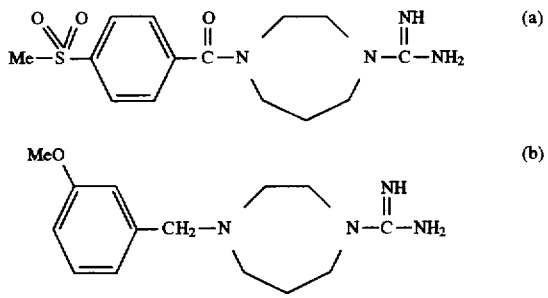

Ryznerski et al.; "Synthesis and pharmacological properties of phenoxyethylpiperazine derivatives," Pol. J Pharmacol. Pharm. 41:191–199 (1989) discloses 2,6-dimethoxyphenoxyethylpiperezine and the 4-amidine derivative thereof. The compounds were tested for their effect on arterial blood pressure in normotensive rats and their effect upon isolated rat heart.

Jameson et al., "Affinity Chromatography of Bovine Trypsin: A Rapid Separation of Bovine α- and β-Trypsin," Biochem J. 141:555–565 (1974) reports on the trypsin-binding ability of affinity columns that comprise a trypsin-substrate coupled to cellulose or Sepharose 40. 4-Amino-N-[[4-[(4-aminoiminomethyl)-amino]butyl]amino]sulfonylphenyl-N-methyl-benzenesulfonamide was disclosed as a trypsin-substrate.

Laid-open application Jpn. Kokai Tokkyo Koho JP 51 75042 A2, published Jun. 29, 1976, discloses compounds having the formula:

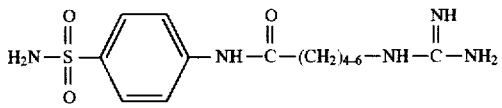

The application discloses that these compounds are effective against ascites sarcoma in mice.

European application EP 372,486, published Jun. 13, 1990, discloses N-amidobenzoyl-β-alanines and analogs thereof that are useful as fibrinogen antagonists.

Chemical Abstracts 110:212261 (1987) discloses a number of 2-mercaptobenzenesulfonamide derivatives, including a compound having the formula:

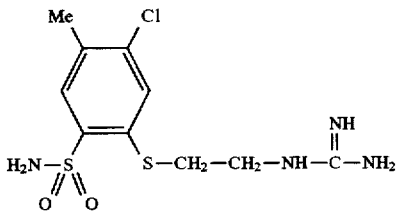

Somorin et al., "Synthesis of New Arginine Derivatives as Substrates of Trypsin," Bull. Chem. Soc. Jpn. 59:1593–1595 (1986) discloses a compound having the formula:

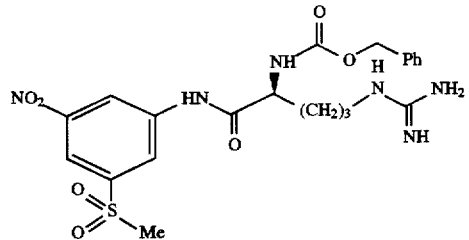

The reference teaches that this compound is a chromogenic arginine substrate for trypsin hydrolysis.

Chemical Abstracts 63:525c (1965) discloses the compound 4-chloro-5-(2-guanidylethylamino)benzene-1,3-disulfonamide. The abstract further discloses that this compound is an effective diuretic.

SUMMARY OF THE INVENTION

The present invention is directed to novel compounds having Formula I (below). Also provided are processes for preparing compounds of Formula I. The novel compounds of the present invention are potent inhibitors of proteases, especially serine proteases, such as chymotrypsin, trypsin, thrombin, plasmin and factor Xa. Certain of the compounds exhibit antithrombotic activity via direct inhibition of thrombin, or are intermediates useful for forming compounds having antithrombotic activity. Other compounds are inhibitors of trypsin and/or chymotrypsin, and are therefore useful in treating pancreatitis. Also provided are methods of inhibiting or treating aberrant proteolysis in a mammal and methods of treating thrombosis, ischemia, stroke, restenosis or inflammation in a mammal by administering an effective amount of a compound of Formula I. Further provided are pharmaceutical compositions comprising a compound of Formula I and one or more pharmaceutically acceptable carriers or diluents.

DETAILED DESCRIPTION OF THE PREFERRED EMBODIMENTS

Compounds of the present invention include compounds of Formula I:

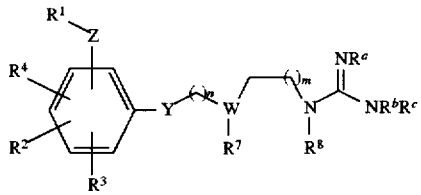

or solvates, hydrates or pharmaceutically acceptable salts thereof;

wherein:

$R^1$ is one of $C_{6-12}$ alkyl, cycloalkyl, alkenyl, alkynyl, aryl, aralkyl or heteroaryl, any of which may be optionally substituted;

Z is one of $-NR^{10}SO_2-$, $-SO_2NR^{10}-$, $-NR^{10}C(R^yR^z)-$, $-C(R^yR^z)NR^{10}-$, $-OSO_2-$, $-SO_2O-$, $-OC(R^yR^z)-$, $-C(R^yR^z)O-$, $-NR^{10}CO-$ or $-CONR^{10}-$, where $R^y$ and $R^z$ are each independently one of hydrogen, alkyl, cycloalkyl, aryl, aralkyl, hydroxyalkyl, carboxyalkyl, aminoalkyl, monoalkylaminoalkyl, dialkylaminoalkyl or carboxy; and $R^{10}$ is defined below;

$R^2$, $R^3$ and $R^4$ are each independently one of hydrogen, alkyl, cycloalkyl, alkenyl, alkynyl, aryl, aralkyl, heteroaryl, trifluoromethyl, halogen, hydroxyalkyl, cyano, nitro, carboxamido, $-CO_2R^x$, $-CH_2OR^x$ or $-OR^x$, or when present on adjacent carbon atoms $R^2$ and $R^3$ may also be taken together to form one of $-CH=CH-CH=CH-$ or $-(CH_2)_q-$, where q is from 2 to 6, and $R^4$ is defined as above;

$R^x$, in each instance, is independently one of hydrogen, alkyl or cycloalkyl wherein said alkyl or cycloalkyl groups may optionally have one or more unsaturations;

Y is one of $-O-$, $-NR^5-$, $-S-$, $-CR^5R^9-$ or a covalent bond;

W is N or $CR^{10}$;

$R^7$ and $R^8$ are each independently one of hydrogen, alkyl, aralkyl, aryl, hydroxyalkyl or carboxyalkyl, or $R^7$ and $R^8$ are taken together to form $-(CH_2)_y-$, where y is zero, 1 or 2, with the proviso that when W is: N, y cannot be zero or 1;

$R^5$, in each instance, is independently one of hydrogen, alkyl, aralkyl, aryl, hydroxyalkyl, aminoalkyl, monoalkylaminoalkyl, dialkylaminoalkyl or carboxyalkyl;

$R^9$ is one of alkyl, aralkyl, aryl, hydroxyalkyl or carboxyalkyl;

$R^{10}$ is hydrogen, aryl, aralkyl, alkyl, alkyloxyalkyl, wherein said alkyl or alkyloxyalkyl may be substituted by a single amino, monoalkylamino, dialkylamino, carboxy, or by one or more hydroxy groups, wherein the hydroxy groups can be further substituted by alkyl, hydroxyalkyl, alkyloxyalkyl, hydroxyalkyloxyalkyl or alkylcarbonyl groups and wherein two vicinal hydroxy groups can each be linked by an alkylidene group; or $R^{10}$ can form the group $-E-P(O)R^{11}R^{12}$, where E is alkylene, preferably having one to 4 carbon atoms; and $R^{11}$ and $R^{12}$ are independently $C_{1-6}$ alkyl groups;

$R^a$, $R^b$ and $R^c$ are independently hydrogen, alkyl, hydroxy, alkoxy, aryloxy, aryloxy, alkoxycarbonyloxy, cyano or $-CO_2R^w$, where $R^w$ is alkyl, cycloalkyl, phenyl, benzyl,

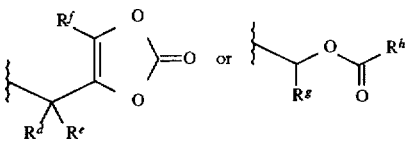

where $R^d$ and $R^e$ are independently hydrogen, $C_{1-6}$ alkyl, $C_{2-6}$ alkenyl or phenyl, $R^f$ is hydrogen, $C_{1-6}$ alkyl, $C_{2-6}$ alkenyl or phenyl, $R^g$ is hydrogen, $C_{1-6}$ alkyl, $C_{2-6}$ alkenyl or phenyl, and $R^h$ is aralkyl or $C_{1-6}$ alkyl;

n is from zero to 8, with the proviso that when W is N and Y is other than $-CR^5R^9-$, then n is from 2 to 8; and m is from zero to 4, provided that when (a) W is N, or (b) W is C, $R^7$ and $R^8$ together form $-(CH_2)_y-$ and y is 2, then m is not zero.

One preferred group of compounds are compounds of Formula I wherein:

$R^1$ is one of $C_{6-12}$ alkyl, cycloalkyl, aryl, aralkyl or heteroaryl, any of which may be optionally substituted by one or more of hydroxy, nitro, trifluoromethyl, halogen, alkoxy, cyano, amino, monoalkylamino, dialkylamino, carboxyalkoxy, mono(carboxyalkyl)amino, di(carboxyalkyl)amino, amidino, guanidino, trifluoromethoxy or perfluoroethoxy, and wherein said aryl, heteroaryl, cycloalkyl and aralkyl may further be optionally substituted by ones or more alkyl moieties;

Z is one of $-NR^{10}SO_2-$, $-SO_2NR^{10}-$, $-NR^{10}CH_2-$, $-CH_2NR^{10}-$, $-OSO_2-$, $-SO_2O-$, $-OCH_2-$ or $-CH_2O-$;

$R^2$, $R^3$ and $R^4$ are each independently one of hydrogen, alkyl, cycloalkyl, aryl, aralkyl, heteroaryl, trifluoromethyl, halogen, hydroxyalkyl, cyano, nitro, carboxamide, $-CO_2R^x$, $-CH_2OR^x$ or $-OR^x$, or when present on adjacent carbon atoms, $R^2$ and $R^3$ may also be taken together to form one of $-CH=CH-CH=CH-$ or $-(CH_2)_q-$, where q is from 2 to 6, and $R^4$ is defined as above;

$R^x$, in each instance, is independently one of hydrogen, alkyl or cycloalkyl wherein said alkyl or cycloalkyl groups may optionally have one or more unsaturations;

Y, W, $R^7$, $R^8$, $R^9$, n and m are defined above; and $R^5$ and $R^{10}$, in each instance, are independently one of hydrogen, alkyl, aralkyl, aryl, $C_{2-10}$ hydroxyalkyl or carboxyalkyl.

A second preferred subgenus of compounds falling within the scope of the present invention include compounds of Formula I wherein:

$R^1$ is one of $C_{6-10}$ aryl, pyridinyl, quinizolinyl, quinolinyl or tetrahydroquinolinyl, any of which is optionally substituted by one or two of hydroxy, nitro, trifluoromethyl, halogen, $C_{1-6}$ alkyl, $C_{1-6}$ alkoxy, $C_{1-6}$ aminoalkyl, $C_{1-6}$ aminoalkoxy, amino, mono($C_{1-4}$) alkylamino, di($C_{1-4}$)alkylamino, $C_{2-6}$ alkoxycarbonylamino, $C_{2-6}$ alkoxycarbonyl, carboxy, $C_{1-6}$ hydroxyalkyl, $C_{2-6}$ hydroxyalkoxy, $C_{2-10}$ mono (carboxyalkyl)amino, di($C_{2-10}$ carboxyalkyl)amino, $C_{6-14}$ ar($C_{1-6}$)alkoxycarbonyl, $C_{2-6}$ alkynylcarbonyl, $C_{1-6}$ alkylsulfonyl, $C_{2-6}$ alkenylsulfonyl, $C_{2-6}$ alkynylsulfonyl, $C_{1-6}$ alkylsulfinyl, $C_{1-6}$ alkylsulfonamido, amidino, guanidino, $C_{1-6}$ alkyliminoamino, formyliminoamino, $C_{2-6}$ carboxyalkoxy, $C_{2-6}$ carboxyalkyl, carboxyalkylamino, cyano, trifluoromethoxy, and perfluoroethoxy;

Z is one of —SO$_2$O—, —SO$_2$NR$^{10}$—, —C(R$^y$R$^z$)O— or —OC(R$^y$R$^z$)—, where R$^y$ and R$^z$ are each hydrogen;

R$^2$, R$^3$ and R$^4$ are independently one of hydrogen, C$_{1-6}$ alkyl, C$_{3-8}$ cycloalkyl, phenyl, benzyl, trifluoromethyl, halogen, hydroxy(C$_{1-8}$)alkyl, cyano, nitro, carboxamido, carboxy, C$_{1-4}$ alkoxycarbonyl, C$_{1-4}$ alkoxymethyl or C$_{1-4}$ alkoxy; or alternatively, R$^2$ and R$^3$, when present on adjacent carbon atoms, may also be taken together to form one of —CH=CH—CH=CH— or —(CH$_2$)$_q$—, where q is from 2 to 6, and R$^4$ is as defined above;

Y is one of —O—, —S—, —NR$^{10}$—, or a covalent bond;

R$^6$ is one of hydrogen, C$_{1-6}$ alkyl, C$_{6-10}$ ar(C$_{1-6}$)alkyl, C$_{6-10}$ aryl, C$_{2-10}$ hydroxyalkyl, C$_{2-10}$ aminoalkyl, mono (C$_{1-4}$)alkylamino(C$_{2-8}$)alkyl, di(C$_{1-4}$)alkylamino(C$_{2-8}$) alkyl or C$_{2-10}$ carboxyalkyl;

R$^7$ and R$^8$ are independently one of hydrogen, C$_{1-6}$ alkyl, C$_{2-10}$ carboxyalkyl or C$_{2-10}$ hydroxyalkyl, or R$^7$ and R$^7$ are taken together to form —(CH$_2$)$_y$— where y is zero, 1 or 2;

R$^5$, in each instance, is independently hydrogen, C$_{1-6}$ alkyl, benzyl, phenyl, C$_{2-10}$ hydroxyalkyl, C$_{2-10}$ aminoalkyl, C$_{1-4}$ monoalkylamino(C$_{2-8}$)alkyl, C$_{1-4}$ dialkylamino(C$_{22-8}$)alkyl or C$_{2-10}$ carboxyalkyl;

R$^9$ is one of C$_{1-6}$ alkyl, benzyl, phenyl, C$_{2-10}$ hydroxyalkyl or C$_{2-10}$ carboxyalkyl;

R$^{10}$ is hydrogen, C$_{1-6}$ alkyl, benzyl, phenyl, C$_{1-6}$ alkyloxy (C$_{1-6}$)alkyl, wherein said C$_{1-6}$ alkyl or C$_{1-6}$ alkyloxy (C$_{1-6}$)alkyl may be substituted by a single amino, C$_{1-4}$ monoalkylamino, di(C$_{1-4}$)alkylamino, carboxy, or by one or more hydroxy groups, or R$^{10}$ can form the group —E—P(O)R$^{11}$R$^{12}$, where E is alkylene, preferably having one to 4 carbon atoms; and R$^{11}$ and R$^{12}$ are independently C$_{1-6}$ alkyl groups;

R$^a$, R$^b$ and R$^c$ are each one of hydrogen, C$_{1-4}$ alkyl, hydroxy, C$_{1-4}$ alkoxy, phenoxy, C$_{1-4}$ alkyloxycarbonyl, benzyloxycarbonyl, cyano,

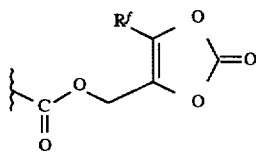

or

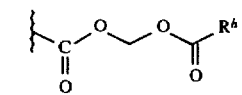

where R$^h$ is benzyl, methyl, ethyl, isopropyl, sec-butyl or t-butyl, and where R$^f$ is hydrogen or C$_{1-6}$ alkyl;

n is from zero to 8, with the proviso that when W is N, then n is from 2 to 8; and m is from zero to 4, provided that when W is N, then m is not zero.

An especially preferred subgenus of compounds include compounds of Formula I wherein:

R$^1$ is one of phenyl or naphthyl, optionally substituted by one or two of chloro, trifluoromethyl, amino or dimethylamino;

Z is one of —SO$_2$O—, —SO$_2$NR$^{10}$—, —CH$_2$O— or —OCH$_2$—;

R$^2$ and R$^3$ are each hydrogen or R$^2$ and R$^3$ may also be taken together to form —CH=CH—CH=CH— or —CH$_2$—CH$_2$—CH$_2$—;

R$^4$ is one of hydrogen, methyl, methoxy or trifluoromethyl;

Y is one of —O—, —NR$^{10}$— or a covalent bond, where R$^{10}$ is defined below;

R$^7$ and R$^8$ are independently one of hydrogen, C$_{1-6}$ alkyl, C$_{2-10}$ hydroxyalkyl or C$_{2-10}$ carboxyalkyl, or R$^7$ and R$^8$ are taken together to form —(CH$_2$)$_y$— where y is zero, 1 or 2;

R$^{10}$ is independently hydrogen, C$_{1-4}$ alkyl, C$_{2-4}$ hydroxyalkyl, C$_{2-4}$ carboxyalkyl, C$_{2-4}$ aminoalkyl, dimethylamino(C$_{2-8}$)alkyl, methylamino(C$_{2-8}$)alkyl;

R$^a$, R$^b$ and R$^c$ are hydrogen, hydroxy,

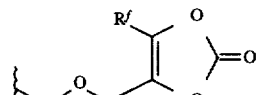

or

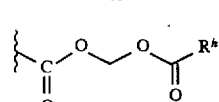

where R$^h$ is benzyl or t-butyl, and where R$^f$ is hydrogen or methyl;

n is from zero to 4; and m is zero, 1, 2 or 3.

Other preferred groups of compounds falling within the scope of the present invention include compounds of the following formulas:

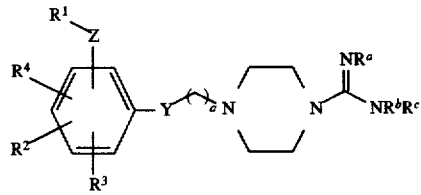

II

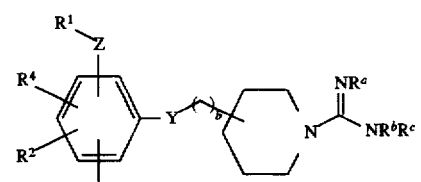

III

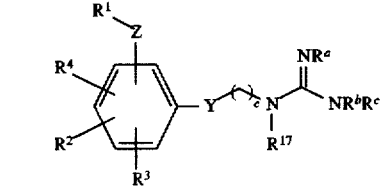

IV

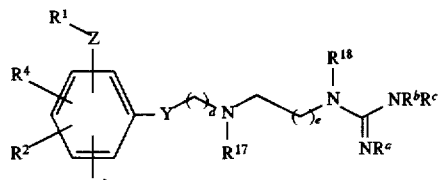

V or solvates, hydrates or pharmaceutically acceptable salts thereof; wherein

Z, Y, $R^1$, $R^2$, $R^3$, $R^4$, $R^a$, $R^b$ and $R^c$ are defined as above;

$R^{17}$ and $R^{18}$ are each independently one of hydrogen, alkyl, aralkyl, aryl, $C_{2-10}$ hydroxyalkyl or carboxyalkyl;

a is from 1 to 8, provided that when Y is other than —$CR^9R^{10}$—, then a is from 2 to 8;

b is from 0 to 8;

c is from 1 to 14, provided that when Y is other than —$CR^5R^9$—, then c is from 2 to 14;

d is from 1 to 8, provided that when Y is other than —$CR^5R^9$—, then d is from 2 to 8; and e is from 1 to 4.

The moiety —Z—$R^1$ of Formulae I–V is attached to the benzene ring in a position ortho-, meta- or para- to Y, preferably ortho- or meta-.

Preferred values of Y for compounds of the present invention are divalent oxygen (—O—) or —$NR^{10}$— and preferred values of Z are —$SO_2NR^{10}$—, —$SO_2O$— or —$CH_2O$—.

Preferred values of $R^1$ for compounds of the present invention are $C_{6-12}$ alkyl, $C_{4-7}$ cycloalkyl, $C_{2-8}$ alkenyl, $C_{2-8}$ alkynyl or $C_{6-14}$ aryl, especially $C_{6-10}$ aryl any of which is optionally substituted. Substituents that can be optionally present on the $R^1$ moieties include one or more, preferably one or two, hydroxy, nitro, trifluoromethyl, halogen, $C_{1-6}$ alkyl, $C_{1-6}$ alkoxy, amino, mono($C_{1-6}$)alkylamino, di($C_{1-6}$)alkylamino, amidino, guanidino, carboxyalkoxy, carboxyalkylamino, cyano, trifluoromethoxy, or perfluoroethoxy. An additional set of preferred values of optional substituents on $R^1$ include hydroxy, nitro, trifluoromethyl, halogen, $C_{1-6}$ alkyl, $C_{1-6}$ alkoxy, $C_{1-6}$ aminoalkyl, $C_{1-6}$ aminoalkoxy, amino, mono($C_{1-4}$)alkylamino, di($C_{1-4}$)alkylamino, $C_{2-6}$ alkoxycarbonylamino, $C_{2-6}$ alkoxycarbonyl, carboxy, $C_{1-6}$ hydroxyalkyl, $C_{2-10}$ mono(carboxyalkyl)amino, di($C_{2-10}$ carboxyalkyl)amino, $C_{6-14}$ ar($C_{1-6}$ alkoxycarbonyl, $C_{2-6}$ alkynylcarbonyl, $C_{1-6}$ alkylsulfonyl, $C_{2-6}$ alkenylsulfonyl, $C_{2-6}$ alkynylsulfonyl, $C_{1-6}$ alkylsulfinyl, $C_{1-6}$ alkylsulfonamido, amidino, guanidino, $C_{1-6}$ alkyliminoamino, formyliminoamino, $C_{2-6}$ carboxyalkoxy, carboxyalkylamino, cyano, trifluoromethoxy, and perfluoroethoxy.

Another set of preferred values for $R^1$ when $R^1$ is heteroaryl or substituted heteroaryl includes pyridyl, thienyl, chromenyl, benzoxazolyl, quinazolinyl, quinolinyl and tetrahydroquinolinyl. Preferred subsitutents when $R^1$ is substituted heteroaryl include one or more substituents independently selected from halogen, $C_{1-6}$ alkyl, $C_{1-6}$ alkoxy, amidino, guanidino, carboxyalkoxy, carboxyalkylamino, amino, mono$C_{1-6}$ alkylamino and/or di($C_{1-6}$)alkylamino.

Useful values of $R^1$ include phenyl, chlorophenyl, iodophenyl, dichlorophenyl, bromophenyl, trifluoromethylphenyl, di-(trifluoromethyl)phenyl, methylphenyl, methoxyphenyl, dimethoxyphenyl, hydroxyphenyl, carboxyphenyl, methylaminophenol, n-butylaminophenyl, amidinophenyl, guanidinophenyl, methoxycarbonylphenyl, naphthyl, hydroxynaphthyl, t-butylphenyl, cyclohexyl, cyclopentyl, 2-propylbutyl, quinolinyl and tetrahydroquinolinyl. Additional useful values of $R^1$ include aminophenyl, formyliminoaminophenyl, acetimidoylaminophenyl, methoxycarbonylphenyl, ethoxycarbonylphenyl and carboxymethoxyphenyl.

The groups $R^2$, $R^3$ and $R^4$ in Formulae I–V substitute for any remaining hydrogen atoms on the benzene ring after allowing for attachment of the moiety —Z—$R^1$. Preferred values for $R^2$, $R^3$ and $R^4$ independently include hydrogen, $C^{1-4}$ alkyl, $C_{4-7}$ cycloalkyl, $C_{6-14}$ aryl, especially $C_{6-10}$ aryl, $C_{6-10}$ ar($C_{1-4}$)alkyl, trifluoromethyl, halogen, hydroxyalkyl, cyano, nitro, carboxamide, —$CO_2R^x$, or —$CH_2CO_2R^x$, where $R^x$, in each instance, is preferably one of, hydrogen, $C_{1-4}$ alkyl or $C_{4-7}$ cycloalkyl. Alternatively, $R^2$ and $R^3$, when attached to adjacent carbon atoms on the benzene ring, are one of —CH=CH—CH=CH— or —$(CH_2)_q$—, where q is from 2 to 6, thereby forming a fused ring. Preferred values of $R^2$ together with $R^3$ include —CH=CH—CH=CH—, —$CH_2$—$CH_2$—$CH_2$— and —$CH_2$—$CH_2$—$CH_2$—$CH_2$—. When $R^2$ and $R^3$ together form a fused ring, $R^4$ is preferably hydrogen.

Useful values of $R^2$, $R^3$ and $R^4$ include hydrogen, methyl, ethyl, chloro, bromo, trifluoromethyl, hydroxymethyl, methoxy, ethoxy, carboxamide, nitro, phenyl, cyclopropyl, hydroxy, isopropyl, methoxycarbonyl, ethoxycarbonyl and benzyl. Additional useful values of $R^2$, $R^3$ and $R^4$ include: $R^2$ and $R^3$ together forming —CH=CH—CH=CH— or —$CH_2$—$CH_2$—$CH_2$— and $R^4$ is hydrogen.

Preferred values of $R^7$ and $R^8$ in Formula I independently include hydrogen, $C_{1-6}$ alkyl, $C_{6-10}$ ar($C_{1-6}$)alkyl, $C_{6-10}$ aryl, $C_{2-10}$ hydroxyalkyl or $C_{2-7}$ carboxyalkyl, or $R^7$ and $R^8$ are taken together to form —$(CH_2)_y$—, where y is most preferably 2. Useful values of $R^7$ and $R^8$ include hydrogen, methyl, ethyl, propyl, n-butyl, benzyl, phenylethyl, 2-hydroxyethyl, 3-hydroxypropyl, 4-hydroxybutyl, 2-carboxymethyl, 3-carboxyethyl and 4-carboxypropyl.

A preferred value of $R^5$ includes hydrogen. Other preferred values of $R^5$, and the preferred values of $R^9$, include $C_{1-6}$ alkyl, $C_{6-10}$ ar($C_{1-6}$)alkyl, $C_{6-10}$ aryl, $C_{2-10}$ hydroxyalkyl and $C_{2-7}$ carboxyalkyl. Suitable values of $R^5$ and $R^9$ include methyl, ethyl, propyl, n-butyl, benzyl, phenylethyl, 2-hydroxyethyl, 3-hydroxypropyl, 4-hydroxybutyl, 2-carboxymethyl, 3-carboxyethyl and 4-carboxypropyl.

Preferred values of $R^{10}$ include hydrogen, $C_{1-6}$ alkyl, $C_{6-10}$ ar($C_{1-6}$)alkyl, $C_{6-10}$ aryl, $C_{2-10}$ hydroxyalkyl $C_{2-10}$ aminoalkyl, $C_{2-7}$ carboxyalkyl, mono($C_{1-4}$ alkyl)amino($C_{1-8}$)alkyl, and di($C_{1-4}$ alkyl)amino ($C_{1-8}$)alkyl. Suitable values of $R^{10}$ include methyl, ethyl, propyl, n-butyl, benzyl, phenylethyl, 2-hydroxyethyl, 3-hydroxypropyl, 4-hydroxybutyl, 2-aminoethyl, 2-carboxymethyl, 3-carboxyethyl, 4-carboxypropyl and 2-(dimethylamino) ethyl.

Preferred values of $R^a$, $R^b$ and $R^c$ include hydrogen, $C_{1-6}$ alkyl, cyano or —$CO_2R^y$, where $R^y$, in each instance, is preferably one of, $C_{1-4}$ alkyl or $C_{4-7}$ cycloalkyl. Suitable values of $R^6$ include hydrogen, methyl, ethyl, propyl, n-butyl, cyano, —$CO_2CH_3$, —$CO_2CH_2CH_3$ and —$CO_2CH_2CH_2CH_3$. In a more preferred embodiment, $R^a$, $R^b$ and $R^c$ are each hydrogen. An additional set of preferred values of $R^a$, $R^b$ and $R^c$ includes hydrogen, hydroxy, $C_{1-6}$alkyl, $C_{1-6}$ alkoxy, cyano or —$CO_2R^y$, where $R^y$ is one of $C_{1-4}$ alkyl, $C_{4-7}$ cycloalkyl or benzyl. Additional suitable values include hydroxy, methoxy, ethoxy and cyano.

Also preferred at $R^a$, $R^b$ and $R^c$ is the group —$CO_2R^w$, where $R^w$ is one of

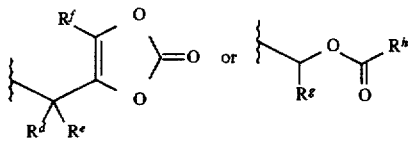

where $R^d$–$R^h$ are defined as above. When $R^a$, $R^b$ and $R^c$ are —$CO_2R^w$, where $R^w$ is one of one of these moieties, the resulting compounds are prodrugs that possess desirable formulation and bioavailability characteristics. A preferred value for each of $R^d$, $R^e$, $R^f$ and $R^g$ is hydrogen, and preferred values for $R^h$ include benzyl and tert-butyl.

Preferred values of n include from 1 to 6, more preferably from 1 to 4, and most preferably 1 or 2, with the proviso that when W is N and Y is other than —CR$^5$R$^9$—, then n is not 1. Preferred values of m include from zero to 4, more preferably zero, 1 or 2, provided that when (a) W is N, or (b) W is C, R$^7$ and R$^8$ together form —(CH$_2$)$_y$— and y is 2, then m is not zero).

Preferred compounds of Formulae IV and V are those where R$^{17}$ and R$^{18}$ are independently one of hydrogen, C$_{1-6}$ alkyl, C$_{6-10}$ar(C$_{1-6}$)alkyl, C$_{6-10}$ aryl, C$_{2-10}$ hydroxyalkyl and C$_{2-7}$ carboxyalkyl. Most preferred compounds are those where R$^{17}$ and R$^{18}$ are hydrogen. Useful values of R$^{17}$ and R$^{18}$ include hydrogen, methyl, ethyl, propyl, n-butyl, benzyl, phenylethyl, 2-hydroxyethyl, 3-hydroxypropyl, 4-hydroxybutyl, 2-carboxymethyl, 3-carboxyethyl and 4-carboxypropyl.

Specific compounds within the scope of the invention include the following examples:

2-chlorobenzenesulfonic acid 3-[[1-(aminoiminomethyl) piperidin-4-yl]methoxy]phenyl ester, 2-chlorobenzenesulfonic acid 3-[[1-(aminoiminomethyl) piperidin-3-yl]methoxy]phenyl ester, 2-chlorobenzenesulfonic acid 3-[[1-(aminoiminomethyl) piperidin-4-yl]methoxy]-5-methylphenyl ester, 2-chlorobenzenesulfonic acid 3-[[1-(aminoiminomethyl) piperidin-3-yl]methoxy]-5-methylphenyl ester, 2-chlorobenzenesulfonic acid 3-[2-[1-(aminoiminomethyl) piperazin-4-yl]-ethoxy]phenyl ester diacetic acid salt, 2-chlorobenzenesulfonic acid 3-[2-[1-(aminoiminomethyl) piperazin-4-yl]ethoxy]-5-methylphenyl ester diacetic acid salt, 2-chlorobenzenesulfonic acid 3-[[1-(aminoiminomethyl) piperidin-4-yl]methoxy]-5-carbomethoxyphenyl ester, 3-(2-chlorobenzyloxy)-5-[[(1-aminoiminomethyl) piperidin-4-yl]methoxy]toluene acetic acid salt, N-methyl-N-[2-[(4-aminoiminomethylamino)butyloxy]-4-methylphenyl]-benzenesulfonamide, acetic acid salt, N-benzyl-N-[[3-(1-aminoiminomethyl)piperidin-4-ylmethylamino]phenyl]benzenesulfonamide, 2-chlorobenzenesulfonic acid 3-[[1-aminoiminomethyl) piperidin-4-yl]methoxy]-4-benzylphenyl ester acetic acid salt, 2-chlorobenzenesulfonic acid 3-[3-(aminoiminomethyl) amino]propoxy]-5-methylphenyl ester acetic acid salt, 2-chlorobenzenesulfonic acid 3-[[4-(aminoiminomethyl) amino]butoxy]-5-methylphenyl ester acetic acid salt, 1-naphthalenesulfonic acid 3-[[1-(aminoiminomethyl) piperidin-4-yl]methoxy]-5-methylphenyl ester acetic acid salt, 3-trifluoromethylbenzenesulfonic acid 3-[[1-(aminoiminomethyl)piperidin-4-yl]methoxy]-5-methylphenyl ester acetic acid salt, benzenesulfonic acid 3-[[1-(aminoiminomethyl)piperidin-4-yl]methoxy]-5-methylphenyl ester acetic acid salt, 3-chlorobenzenesulfonic acid 3-[[1-(aminoiminomethyl) piperidin-4-yl)methoxy]-5-methylphenyl ester acetic acid salt, 2-chlorobenzenesulfonic acid 3-[[1-(aminoiminomethyl) piperidin-4-yl]methoxy]-5-methoxyphenyl ester, 2-chlorobenzenesulfonic acid 3-[[1-(aminoiminomethyl) piperidin-4-yl]methoxy]-4-ethoxycarbonyl-5-methylphenyl ester hydrochloride, 2-trifluoromethylbenzenesulfonic acid 3-[[1-(aminoiminomethyl)piperidin-4-yl]methoxy]-5-methylphenyl ester acetic acid salt, 3-methylbenzenesulfonic acid 3-[[1-(aminoiminomethyl) piperidin-4-yl]methoxy]-5-methylphenyl ester acetic acid salt, 2-chlorobenzenesulfonic acid 3-[[1-aminoiminomethyl) piperidin-4-yl]methoxy]-5-ethylphenyl ester hydrochloride, 2-chlorobenzenesulfonic acid 3-[[5-(aminoiminomethyl) amino]pentoxy]-5-methylphenyl ester hydrochloride, 2,3-dichlorobenzenesulfonic acid 3-[[1-(aminoiminomethyl)piperidin-4-yl]methoxy]-5-methylphenyl ester hydrochloride, 2-chlorobenzenesulfonic acid 3-[[1-(aminoiminomethyl) piperidin-4-yl]methoxy]naphthalen-1-yl ester hydrochloride, 2-chlorobenzenesulfonic acid 3-[[1-(aminoiminomethyl) piperidin-4-yl]methoxy]-5-hydroxymethylphenyl ester, 2-{(2-chlorobenzenesulfonyl)[3-[[1-(aminoiminomethyl) piperidin-4-yl]methoxy]-5-[trifluoromethyl]phenyl] amino}acetic acid hydrochloride, 2-{benzenesulfonyl-[3-[[1-(aminoiminomethyl)piperidin-4-yl]methoxy]-5-[trifluoromethyl]phenyl]amino}acetic acid hydrochloride, 2-chloro-N-{3-[[1-(aminoiminomethyl)piperidin-4-yl] methoxy]-5-[trifluoromethyl]phenyl}benzenesulfonamide hydrochloride, and N-benzyl-N-[[3-(1-aminoiminomethyl)-piperidin-4-ylmethyl]-carboxymethyl]amino]phenyl]-2-chlorobenzernesulfonamide.

Additional compounds within the scope of the present invention include:

3-methoxybenzenesulfonic acid 3-[[1-(aminoiminomethyl) piperidin-4-yl]methoxy]-5-methylphenyl ester hydrochloride;

3-[(carboxy)methoxy]benzenesulfonic acid 3-[[1-(aminoiminomethyl)piperidin-4-yl]methoxy]-5-methylphenyl ester;

3-hydroxybenzenesulfonic acid 3-[[1-(aminoiminomethyl) piperidin-4-yl]methoxy]-5-methylphenyl ester hydrochloride;

3-(2'-hydroxyethoxy)benzenesulfonic acid 3-[[1-(aminoiminomethyl)piperidine-4-yl]methoxy]-5-methylphenyl ester hydrochloride;

3-(2',3'-dihydroxypropoxy)benzenesulfonic acid 3-[[1-(aminoiminomethyl)piperidin-4-yl]methoxy]5-methylphenyl ester hydrochloride;

2-chlorobenzenesulfonic acid 3-[[1-(aminoiminomethyl) piperidin-4-yl]methoxy]-5-chlorophenyl ester hydrochloride;

3-nitrobenzenesulfonic acid 3-[[1-(aminoiminomethyl) piperidin-4-yl]methoxy]-5-methylphenyl ester hydrochloride;

3-aminobenzenesulfonic acid 3-[[1-(aminoiminomethyl) piperidin-4-yl]methoxy]-5-methylphenyl ester hydrochloride;

2-methoxycarbonylbenzenesulfonic acid 3-[[1-(aminoiminomethyl)piperidin-4-yl]methoxy]-5-methylphenyl ester hydrochloride;

4-nitrobenzenesulfonic acid 3-[[1-(aminoiminomethyl) piperidin-4-yl]methoxy]-5-methylphenyl ester hydrochloride; and 4-aminobenzenesulfonic acid 3-[[1-(aminoiminomethyl) piperidin-4-yl]methoxy]-5-methylphenyl ester hydrochloride;

2-nitrobenzenesulfonic acid 3-[[1-(aminoiminomethyl) piperidin-4-yl]methoxy]-5-methylphenyl ester hydrochloride;

2-aminobenzenesulfonic acid 3-[[1-(aminoiminomethyl) piperidin-4-yl]methoxy]-5-methylphenyl ester hydrochloride;

2-chloro-3-nitrobenzenesulfonic acid 3-[[1-(aminoiminomethyl)piperidin-4-yl]methoxy]-5-methylphenyl ester hydrochloride;

3-amino-2-chlorobenzenesulfonic acid 3-||1-(aminoiminomethyl)piperidin-4-yl|methoxy|-5-methylphenyl ester dihydrochloride;

2-chlorobenzenesulfonic acid 5-||1-(aminoiminomethyl)piperidin-4-yl|methoxy|-2-(ethoxycarbonyl)-3-methylphenyl ester hydrochloride;

2-chlorobenzenesulfonic acid 1-||1-(aminoiminomethyl)piperidin-4-yl|methoxy|naphthalen-3-yl ester acetic acid salt;

3-(2-chlorobenzyloxy)-1-||(1-aminoiminomethyl)piperidin-4-yl|methoxy|benzene acetic acid salt;

6-((2-chlorobenzenesulfonyl)-{3-||(1-aminoiminomethyl)piperidin-4-yl|methoxy|-5-methylphenyl}amino) hexanoic acid methyl ester hydrochloride;

6-((2-chlorobenzenesulfonyl)-{3-||(1-aminoiminomethyl)piperidin-4-yl|methoxy|-5-methylphenyl}amino) hexanoic acid hydrochloride;

6-((2-chlorobenzenesulfonyl)-{3-||(1-aminoiminomethyl)piperidin-4-yl]methoxy|-5-(trifluoromethyl)phenyl}amino)hexanoic acid;

N-(2-propyl)-N-{|3-(1-aminoiminomethyl)piperidin-4-ylmethoxy|-5-trifluoromethyl}phenyl-2-chorobenzenesulfonamide hydrochloride;

2-chlorobenzenesulfonic acid 3-|[1-(N-methoxycarbonyl-aminoiminomethyl)piperidin-4-yl|methoxy]-5-methylphenyl ester;

2-chlorobenzenesulfonic acid 3-[[1-((N-methoxycarbonylamino)-N-methoxycarbonyliminomethyl)piperidin-4-yl]methoxy]-5-methylphenyl ester;

2-chlorobenzenesulfonic acid 3-[[1-((N,N-di(methoxycarbonyl)-amino)-N-methoxycarbonyliminomethyl)piperidin-4-yl]methoxy]-5-methylphenyl ester; and 2-chlorobenzenesulfonic acid 3-{N-[[3-(aminoiminomethyl)amino|propyl]-N-(methyl)aminomethyl}phenyl ester acetic acid salt.

It is also to be understood that the present invention is considered to include stereoisomers as well as optical isomers, e.g. mixtures of enantiomers as well as individual enantiomers and diastereomers, which arise as a consequence of structural asymmetry in selected compounds of the present series.

The compounds of Formulae I–V may also be solvated, especially hydrated. Hydration may occur during manufacturing of the compounds or compositions comprising the compounds, or the hydration may occur over time due to the hygroscopic nature of the compounds.

Certain compounds within the scope of Formulae I–V are derivatives referred to as prodrugs. The expression "prodrug" denotes a derivative of a known direct acting drug, which derivative has enhanced delivery characteristics and therapeutic value as compared to the drug, and is transformed into the active drug by an enzymatic or chemical process; see Notari, R. E., "Theory and Practice of Prodrug Kinetics," *Methods in Enzymology*, 112:309–323 (1985); Bodor, N., "Novel Approaches in Prodrug Design," *Drugs of the Future*, 6(3):165–182 (1981); and Bundgaard, H., "Design of Prodrugs: Bioreversible-Derivatives for Various Functional Groups and Chemical Entities," in *Design of Prodrugs* (H. Bundgaard, ed.), Elsevier, New York (1985). Useful prodrugs are those where $R^a$, $R^b$ and/or $R^c$ are —$CO_2R^w$, where $R^w$ is defined above. See, U.S. Pat. No. 5,466,811 and Saulnier et al., *Bioorg Med. Chem. Lett.* 4:1985–1990 (1994).

The term "alkyl" as employed herein by itself or as part of another group refers to both straight and branched chain radicals of up to 12 carbons, such as methyl, ethyl, propyl, isopropyl, butyl, t-butyl, isobutyl, pentyl, hexyl, isohexyl, heptyl, 4,4-dimethylpentyl, octyl, 2,2,4-trimethylpentyl, nonyl, decyl, undecyl, dodecyl.

The term "aryl" as employed herein by itself or as part of another group refers to monocyclic or bicyclic aromatic groups containing from 6 to 12 carbons in the ring portion, preferably 6–10 carbons in the ring portion, such as phenyl, naphthyl or tetrahydronaphthyl.

The term "heteroaryl" as employed herein refer s to groups having 5 to 14 ring atoms; 6, 10 or 14 π electrons shared in a cyclic array; and containing carbon atoms and 1, 2 or 3 oxygen, nitrogen or sulfur heteroatoms (where examples of heteroaryl groups are: thienyl, benzo|b|thienyl, naphtho|2,3-b|thienyl, thianthrenyl, furyl, pyranyl, isobenzofuranyl, benzoxazolyl, chromenyl, xanthenyl, phenoxathiinyl, 2H-pyrrolyl, pyrrolyl, imidazolyl, pyrazolyl, pyridyl, pyrazinyl, pyrimidinyl, pyridazinyl, indolizinyl, isoindolyl, 3H-indolyl, indolyl, indazolyl, purinyl, 4H-quinolizinyl, isoquinolyl, quinolyl, phthalazinyl, naphthyridinyl, quinazolinyl, cinnolinyl, pteridinyl, 4aH-carbazolyl, carbazolyl, β-carbolinyl, phenanthridinyl, acridinyl, pyrimidinyl, phenanthrolinyl, phenazinyl, isothiazolyl, phenothiazinyl, isoxazolyl, furazanyl and phenoxazinyl groups).

The term "aralkyl" or "arylalkyl" as employed herein by itself or as part of another group refers to $C_{1-6}$ alkyl groups as discussed above having an aryl substituent, such as benzyl, phenylethyl or 2-naphthylmethyl.

The term "cycloalkyl" as employed herein by itself or as part of another group refers to cycloalkyl groups containing 3 to 9 carbon atoms. Typical examples are cyclopropyl, cyclobutyl, cyclopentyl, cyclohexyl, cycloheptyl, cyclooctyl and cyclononyl.

The terms "alkoxy" refers to any of the above alkyl groups linked to an oxygen atom.

The term "halogen" or "halo" as employed herein by itself or as part of another group refers to chlorine, bromine, fluorine or iodine with chlorine being preferred.

The term "monoalkylamine" as employed herein by itself or as part of another group refers to an amino group which is substituted with one alkyl group having from 1 to 6 carbon atoms.

The term "dialkylamine" as employed herein by itself or as part of another group refers to an amino group which is substituted with two alkyl groups, each having from 1 to 6 carbon atoms The term "hydroxyalkyl" as employed herein refers to any of the above alkyl groups substituted by one or more hydroxyl moieties.

The term "carboxyalkyl" as employed herein refers to any of the above alkyl groups substituted by one or more carboxylic acid moieties.

The compounds of the present invention defined by Formulae I–V in which Z is —$OSO_2R^1$ or Z is —$OCH_2R^1$ may be prepared by standard techniques 5 as outlined in Schemes Ia and Ib.

Scheme Ia illustrates the preparation of compounds of the present invention where Z-$R^1$ is —$OSO_2$—$R^1$.

Scheme Ia

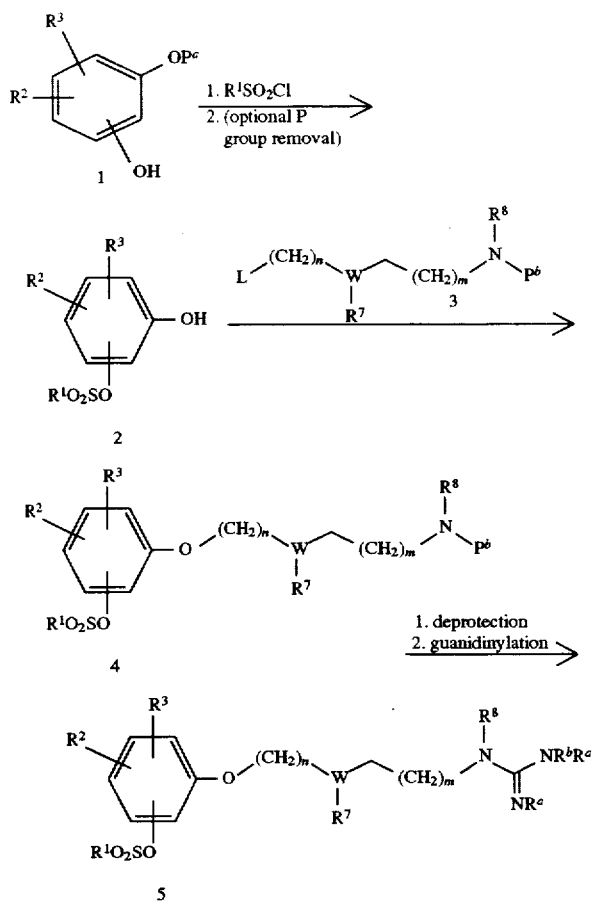

$R^1$–$R^3$, $R^7$–$R^8$, $R^a$, $R^b$, $R^c$, n, and are as defined above; $P^a$ is a hydroxyl protecting group or hydrogen, and $P^b$ is an amino protecting group.

Phenols 1 (where P is H) are converted to monosulfonates 2 by treatment with appropriate sulfonyl chlorides. Preferred conditions include treating phenol 1 with a sulfonyl chloride in a biphasic system composed of either and an aqueous phase saturated with NaHCO$_3$. Alternatively, the reaction may be effected first by deprotonating 1 with a strong base, most preferably NaH, in a polar organic solvent, such as DMF or tetrahydrofuran, followed by treating the deprotonated phenol with the sulfonyl chloride. Still alternatively, phenol 1, in a typical organic solvent, such as methylene chloride, may be converted to 2 by treating the phenol with sulfonyl chloride in the presence of an amine base, such as N-methylmorpholine.

Phenols 1 may be monoprotected ($P^a$ is a protecting group) with a variety of protecting groups known in the art, such as esters and benzyl ethers (Greene, T. W. & Wuts, P. G. M., *Protective Groups in Organic Synthesis*, 2nd edition, John Wiley and Sons, Inc., New York (1991)). Deprotection of the hydroxyl groups is routinely accomplished using reaction conditions well-known in the art. For example, deprotection of benzyl ethers may be effected through catalytic hydrogenation using palladium on carbon as a catalyst in solvents such as ethanol or tetrahydrofuran. Deprotection of an acetate is accomplished by basic hydrolysis, most preferably with sodium hydroxide in aqueous tetrahydrofuran.

Phenols 2 are coupled to 3 (for L=OH) using a Mitsunobu coupling procedure (Mitsunobu, O., *Synthesis* 1 (1981)) to provide 4. Preferred coupling conditions include using a trialkylphosphine or triarylphosphine, such as triphenylphosphine, in a suitable solvent such as tetrahydrofuran or methylene chloride, and a dialkyl azodicarboxylate, such as diethyl azodicarboxylate. In some cases, it is advantageous to add an amine base such as N-methylmorpholine. The amine terminus of 3 is protected with a protecting group $P^b$ that is readily removed from 4. Amino-protecting groups are well known in the art (Greene, T. W. & Wuts, P. G. M., *Protective Groups in Organic Synthesis*, 2nd edition, John Wiley and Sons, Inc., New York (1991)). Deprotection of the amino group is effected by employing reaction conditions that are well known in the art. For example, the t-butoxycarbonyl (BOC) may be removed by exposure to strongly acidic medium, such as hydrogen chloride, in a suitable solvent, such as dioxane, or a mixed trifluoroacetic acid/methylene chloride solvent system. Benzyloxycarbonyl (CBz) groups may be removed be hydrogen using palladium on carbon as a catalyst in solvents such as ethanol or tetrahydrofuran. The resulting amine is then converted to guanidine 5 using standard reagents such as aminoiminomethanesulfonic acid (Miller, A. E. & Bischoff, J. J., *Synthesis*, 777 (1986)) or 1H-pyrazole-1-carboxamidine hydrochloride (Bernatowicz, M. S. et al., *J. Org. Chem.* 57(8):2497 (1992)).

Scheme Ib illustrates the preparation of compounds of the present invention where Z-$R^1$ is —O—CH$_2$—$R^1$.

Scheme Ib

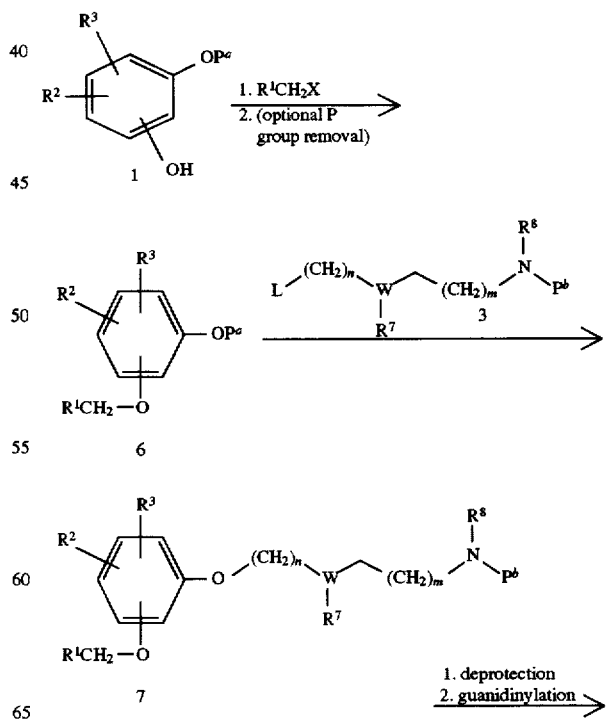

17

-continued
Scheme Ib

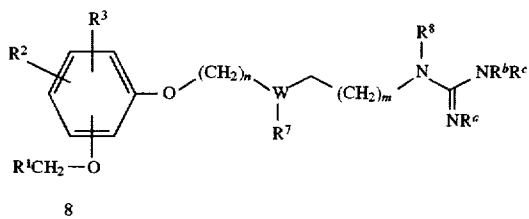

8

$R^1$–$R^3$, $R^7$–$R^8$, $R^a$, $R^b$, $R^c$, n, m, $P^a$ and $P^b$ are as defined above.

Aryl ethers 8 are synthesized in a fashion analogous to synthesis of 5. Phenol 1 (P is H) is converted to derivative 6 by treating 1 with a strong base, preferably NaH, in a suitable solvent such as DMF, followed by addition of a reactive alkyl or benzyl compound 4 (where X is a reactive functional group such as iodide, chloride, bromide or alkylsulfonate). Alternatively, the Mitsunobu Reaction may be used with an appropriate $R^1CH_2X(X=OH)$ using the reaction conditions described above. The use of suitable alcohol protecting groups ($P^a$), such as esters, to suppress over-alkylation, is well known in the art (Greene, T. W. & Wuts, P. G. M., *Protective Groups in Organic Synthysis*, 2nd edition, John Wiley and Sons, Inc., New York (1991)). The protecting group may then be removed using well-known techniques, for example by hydrolysis with aqueous NaOH, when an ester protecting group is employed. Phenol 6 is then converted to 8 using the conditions described for formation of 5.

Scheme II depicts synthetic routes to additional compounds of the present invention.

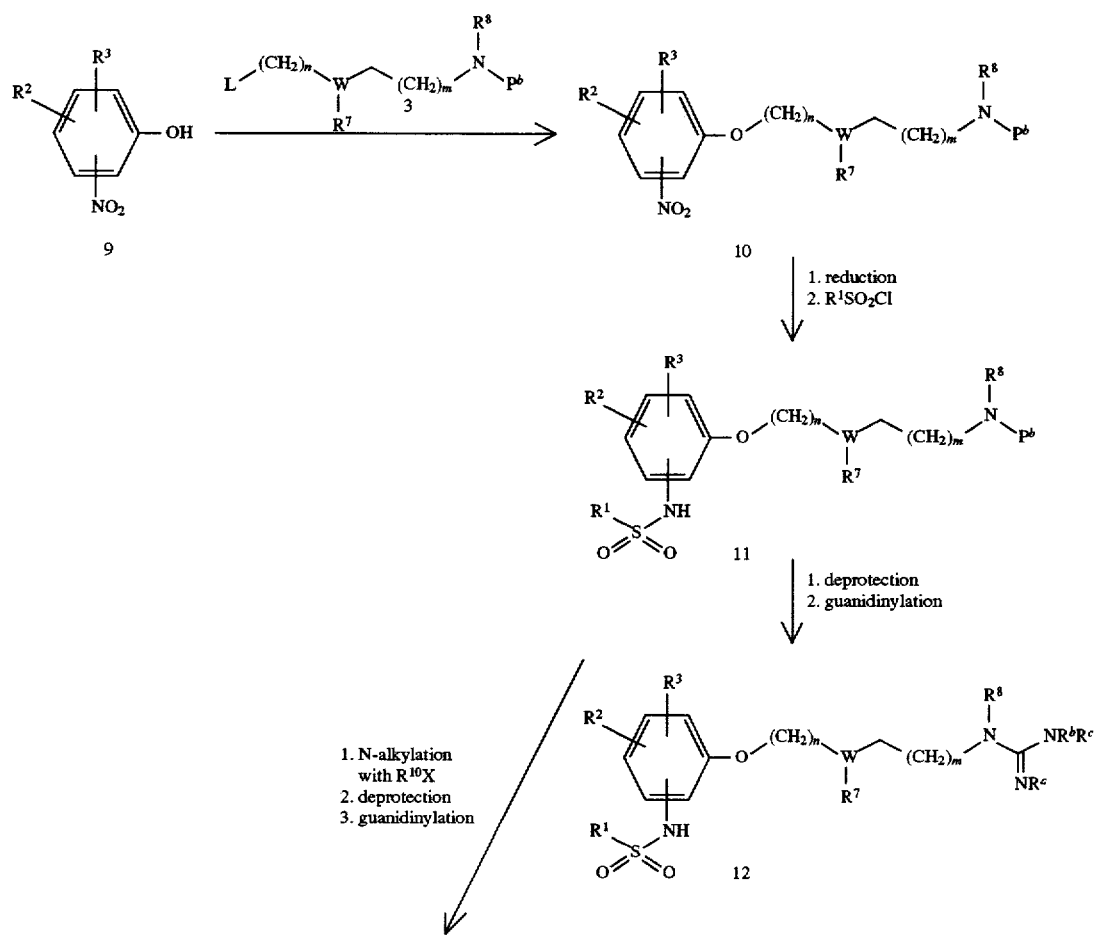

-continued
Scheme II

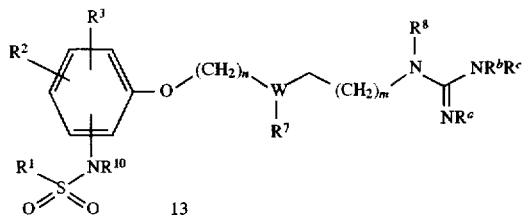

$R^1$–$R^3$, $R^7$–$R^8$, $R^{10}$, $R^a$, $R^b$, $R^c$, n, m, $P^a$ and $P^b$ are as defined above.

According to Scheme II, a nitrophenol 9 may be coupled to compound 3 by standard techniques. Preferably, the reaction is effected by the Mitsunobu reaction (where L is OH). Alternatively, 9 may be treated with a base, such as NaH, in a suitable solvent such as DMF or THF, followed by addition of 3 (where L is a reactive group, such as Cl, Br, I or alkylsulfonate). The nitro group is thereafter reduced, for example, by catalytic reduction using palladium on carbon in a suitable solvent such as ethanol or tetrahydrofuran. The resulting product in then treated with an appropriate sulfonyl chloride ($R^1SO_2Cl$) to provide 11. Removal of the amine protecting group $P^b$ is accomplished by techniques known in the art. For example, the t-butoxycarbonyl (BOC) is removed by exposure to a strongly acidic medium, such as hydrogen chloride in a suitable solvent such as dioxane or trifluoroacetic acid in methylene chloride. Benzyloxycarbonyl (CBz) groups are removed by catalytic hydrogen using palladium on carbon as a catalyst in solvents such as ethanol or tetrahydrofuran.

The resulting amine is then converted to guanidine 13 using standard reagents such as aminoiminomethanesulfonic acid (Miller, A. E. & Bischoff, J. J., Synthesis, 777(1986)) or 1H-pyrazole-1-carboxamidine hydrochloride (Bernatowicz, M. S. et al., J Org Chem. 57(8):2497 (1992)). Alternatively, bis-(tert-butoxycarbonyl)/guanylpyrazole (Michael S. Bernatowicz, M. S. et al., Tetrahedron Lett. 34(2):3389 (1993)) may be used, which, after deprotection with an acidic medium, such as HCl or trifluoroacetic acid, provides 13. N-Substituted sulfonamide derivative 12 is obtained by alkylation of 11 employing a suitable alkylating agent ($R^{10}X$) in the presence of a base, most preferably $Cs_2CO_3$ using a polar solvent such as DMF. Deprotection and guanidinylation are then executed in a manner similar to the conversion of 11 to 13.

Additionally, compounds of the present invention may be prepared by Scheme III.

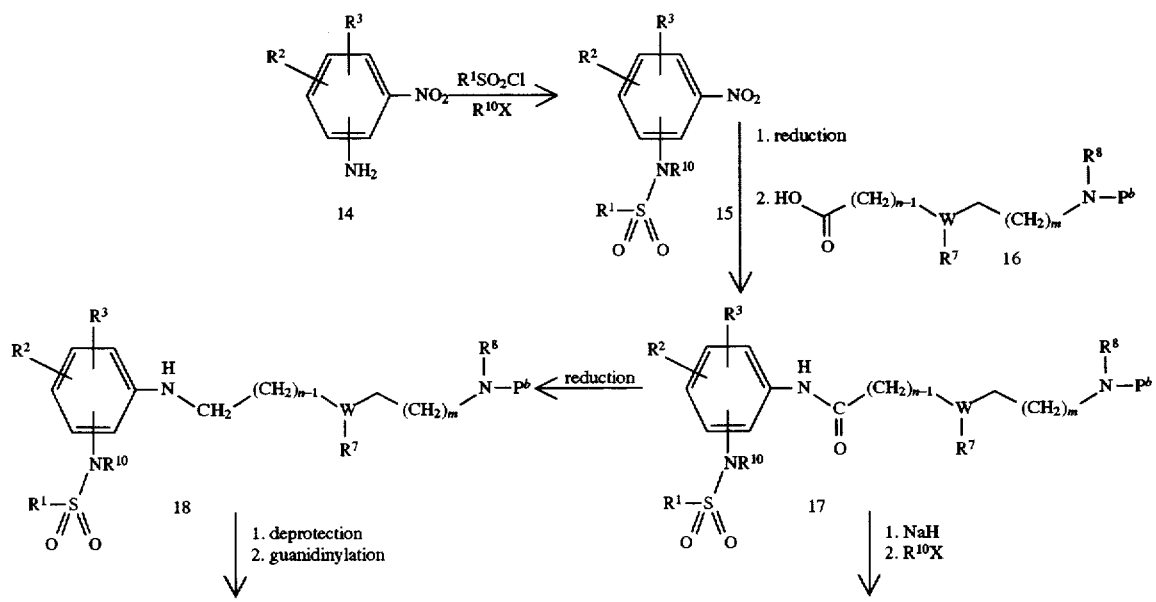

Scheme III

Scheme III (continued)

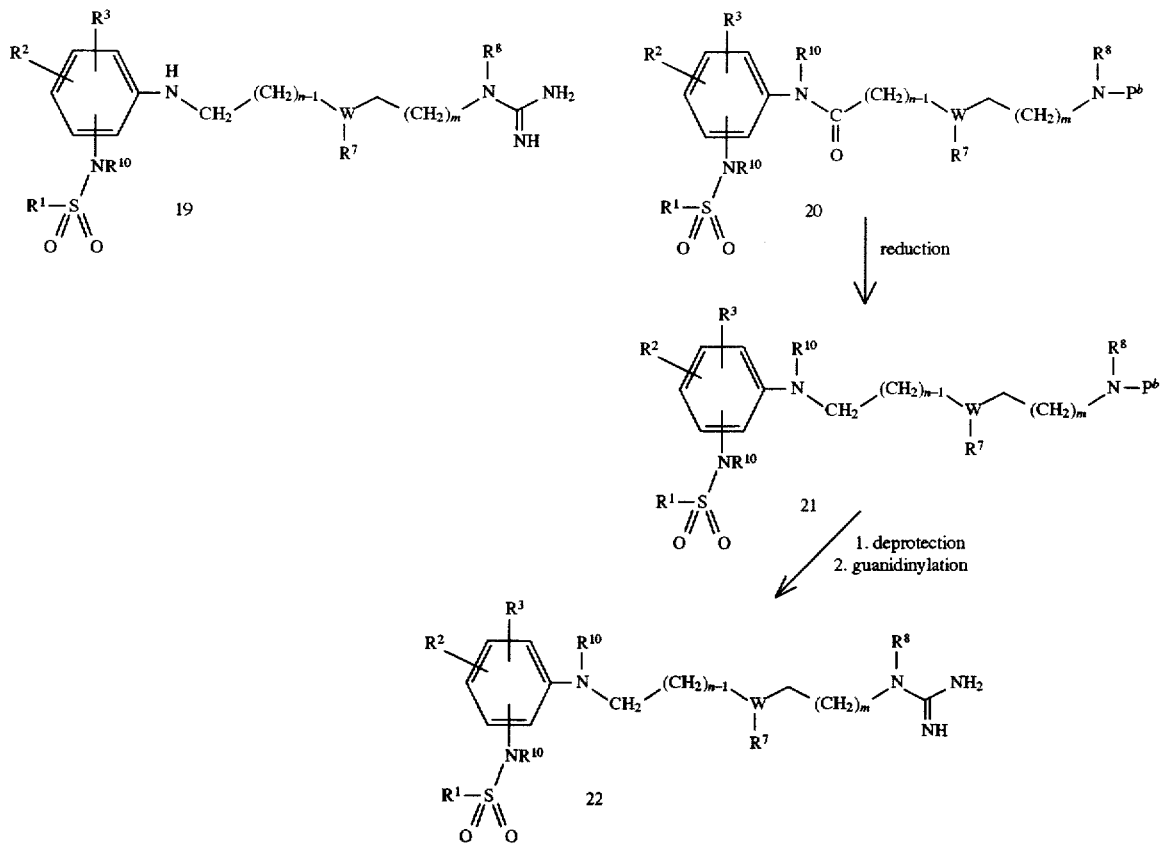

$R^1$-$R^3$, $R^7$, $R^8$, $R^{10}$, $R^a$, $R^b$, $R^c$, n, m and $P^b$ are each as defined above.

According to Scheme III, nitroaniline 14 is converted to a sulfonamide by treatment with an appropriate sulfonyl chloride $R^1SO_2Cl$ in the presence of a weak base, such as N-methylmorpholine. The resulting sulfonamide nitrogen is alkylated with a suitable alkylating agent ($R^{10}X$) in the presence of a base, preferably an alkali metal carbonate such as $Cs_2CO_3$ or $K_2CO_3$, using a polar solvent, such as DMF, to provide intermediate 15. After reduction of the nitro group, the resulting aniline is coupled to a carboxylic acid, 16, to provide amide 17. Amide coupling may be performed using any of a number of common peptide coupling reagents. Preferably, one of 1,3-dicyclohexylcarbodiimide or Castro's reagent (BOP) are employed (B. Castro et al., *Tetrahedron Lett.*:1219 (1975)). Alternatively, 17 may be formed by coupling the aniline with the corresponding acid chloride of acid 16 in the presence of an acid scavenger, such as N-methylmorpholine. Amide 17 is converted to amine 18 by reduction of the amide functionality with an appropriate hydride reagent, preferably borane-THF complex or chlorotrimethylsilane and lithium borohydride. This reaction occurs in a suitable polar solvent, such as THF. Removal of the amine protecting group $P^b$ and formation of the guanidine as described in Scheme II provides the desired compound 19. Alternatively the amide nitrogen may be alkylated using a strong base, such as sodium hydride, in a suitable polar solvent such as DMF, followed by treatment with an alkylating agent ($R^{10}X$) to afford intermediate 20. Reduction of the amide, as executed in the formation of 18, to give 21 followed by deprotection and guanidinylation as previously described provides the analogous compound 22.

Additionally, compounds of the present invention may be prepared by Scheme IV.

Scheme IV

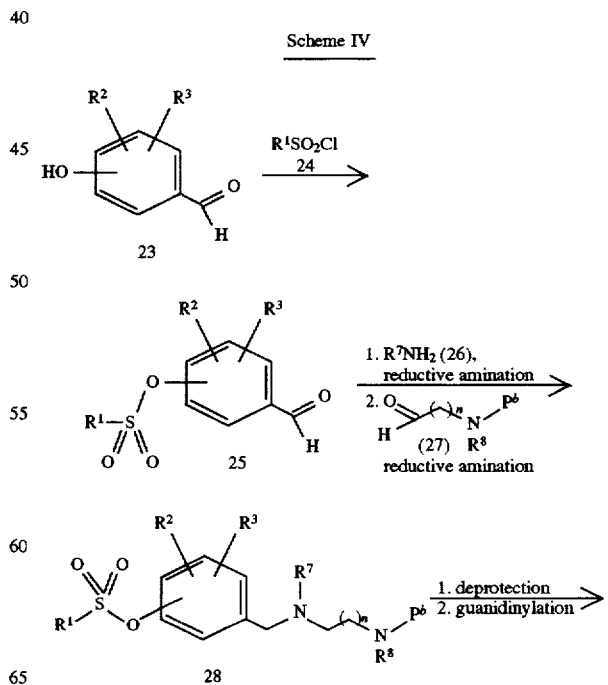

-continued
Scheme IV

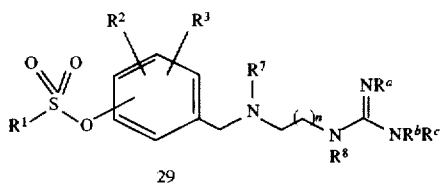

29

$R^1$-$R^3$, $R^7$, $R^8$, $R^a$, $R^b$, $R^c$, n, m and $P^b$ are each as defined above.

Compounds 25 are obtained by treating phenols 23 with an appropriate sulfonyl chloride 24 under standard conditions. Preferred conditions include treating phenol 23 with 24 in the presence of diisopropylethylamine in methylene chloride. Compound 25 is converted to 28 using a set of sequential reductive aminations, first with amine 26, the product of which is coupled to 27, where $P^b$ and $R^8$ are defined previously. The preferred reducing agent is tetramethylammonium triacetoxyborohydride. Alternatively, sodium triacetoxyborohydride, or sodium cyanoborohydride may be used. Still alternatively, reductive amination may be carried out first by forming an imine (Schiff's base) between amine and the carbonyl component using a catalytic amount of acid such as p-toluenesulfonic acid, followed by reduction with sodium borohydride. Still alternatively, the imine may be reduced using catalytic hydrogenation using a catalyst such as palladium on carbon in standard solvents such as ethanol. Conversions of 28 to 29 are accomplished using the conditions defined in Scheme Ia.

It is to be understood that in each of the above-mentioned schemes, an additional substituent, $R^4$, may be present on the phenyl ring of the starting material.

For medicinal use, the pharmaceutically acceptable acid addition salts, those salts in which the anion does not contribute significantly to toxicity or pharmacological activity of the organic cation, are preferred. The acid addition salts are obtained either by reaction of an organic base of Formulae I-V with an organic or inorganic acid, preferably by contact in solution, or by any of the standard methods detailed in the literature available to any practitioner skilled in the art. Examples of useful organic acids are carboxylic acids such as maleic acid, acetic acid, tartaric acid, propionic acid, fumaric acid, isethionic acid, succinic acid, cyclamic acid, pivalic acid and the like; useful inorganic acids are hydrohalide acids such as HCl, HBr, HI; sulfuric acid; phosphoric acid and the like. Preferred acids for forming acid addition salts include HCl and acetic acid.

The compounds of the present invention represent a novel class of potent inhibitors of metallo, acid, thiol and serine proteases. Examples of the serine proteases inhibited by compounds within the scope of the invention include leukocyte neutrophil elastase, a proteolytic enzyme implicated in the pathogenesis of emphysema; chymotrypsin and trypsin, digestive enzymes; pancreatic elastase, and cathepsin G, a chymotrypsin-like protease also associated with leukocytes; thrombin and factor Xa, proteolytic enzymes in the blood coagulation pathway. Inhibition of thermolysin, a metalloprotease, and pepsin, an acid protease, are also contemplated uses of compounds of the present invention.

An end use application of the compounds that inhibit chymotrypsin and trypsin is in the treatment of pancreatitis. For their end-use application, the potency and other biochemical parameters of the enzyme-inhibiting characteristics of the compounds of the present invention is readily ascertained by standard biochemical techniques well-known in the art. Actual dose ranges for their specific end-use application will, of course, depend upon the nature and severity of the disease state of the patient or animal to be treated, as determined by the attending diagnostician. It is expected that a useful dose range will be about 0.01 to 10 mg per kg per day for an effective therapeutic effect.

Compounds of the present invention that are distinguished by their ability to inhibit either factor Xa or thrombin may be employed for a number of therapeutic purposes. As factor Xa or thrombin inhibitors, compounds of the present invention inhibit thrombin production. Therefore, these compounds are useful for the treatment or prophylaxis of states characterized by abnormal venous or arterial thrombosis involving either thrombin production or action. These states include, but are not limited to, deep vein thrombosis; disseminated intravascular coagulopathy which occurs during septic shock, viral infections and cancer; myocardial infarction; stroke; coronary artery bypass; hip replacement; and thrombus formation resulting from either thrombolytic therapy or percutaneous transluminal coronary angioplasty (PCTA). The compounds of the present invention may also be used as an anticoagulant in extracorporeal blood circuits.

By virtue of the effects of both factor Xa and thrombin on a host of cell types, such as smooth muscle cells, endothelial cells and neutrophils, the compounds of the present invention find additional use in the treatment or prophylaxis of adult respiratory distress syndrome; inflammatory responses, such as edema; reperfusion damage; atherosclerosis; and restenosis following an injury such as balloon angioplasty, atherectomy, and arterial stent placement.

The compounds of the present invention may be useful in treating neoplasia and metastasis as well as neurodegenerative diseases, such as Alzheimer's disease and Parkinson's disease.

When employed as thrombin or factor Xa inhibitors, the compounds of the present invention may be administered in an effective amount within the dosage range of about 0.1 to about 500 mg/kg, preferably between 0.1 to 10 mg/kg body weight, on a regimen in single or 2-4 divided daily doses.

When employed as inhibitors of thrombin, the compounds of the present invention may be used in combination with thrombolytic agents such as tissue plasminogen activator, streptokinase, and urokinase. Additionally, the compounds of the present invention may be used in combination with other antithrombotic or anticoagulant drugs such as, but: not limited to, fibrinogen antagonists and thromboxane receptor antagonists.

Human leucocyte elastase is released by polymorphonuclear leukocytes at sites of inflammation and thus is a contributing cause for a number of disease states. Thus, compounds of the present invention are expected to have an anti-inflammatory effect useful in the treatment of gout, rheumatoid arthritis and other inflammatory diseases, and in the treatment of emphysema. Cathepsin G has also been implicated in the disease states of arthritis, gout and emphysema, and in addition, glomerulonephritis and lung infestations caused by infections in the lung. In their end-use application the enzyme inhibitory properties of the compounds of Formulae I-V is readily ascertained by standard biochemical techniques that are well-known in the art.

The neutrophil elastase inhibitory properties, of compounds within the scope of the present invention are determined by the following method. Neutrophil elastase is prepared by the procedure described by Baugh et al., *Biochemistry* 15: 836 (1979). Enzyme assays are conducted substantially according to the procedure disclosed by Nakajima et al., *J Biol. Chem.* 254: 4027 (1979), in assay mixtures containing 0.10M Hepes (N-2-hydroxyethylpiperazine-N'-

2-ethanesulfonic acid) buffer, pH 7.5; 0.5M NaCl; 10% dimethylsulfoxide; and $1.50 \times 10^{-4}$M MeOSuc-Ala-Ala-Pro-Val-p-nitroanilide as substrate. Inhibitors are evaluated by comparing enzymatic activity measured in the presence and absence of inhibitor.

The Cathepsin G inhibitory properties of compounds within the scope of the present invention are determined by the following method. A preparation of partially purified human Cathepsin G is obtained by the procedure of Baugh et al., *Biochemistry* 15: 836 (1979). Leukocyte granules are a major source for the preparation of leukocyte elastase and cathepsin G (chymotrypsin-like activity). Leukocytes are lysed and granules are isolated. The leukocyte granules are extracted with 0.20M sodium acetate, pH 4.0, and extracts are dialyzed against 0.05M Tris buffer, pH 8.0 containing 0.05M NaCl overnight at 4° C. A protein fraction precipitates during dialysis and is isolated by centrifugation. This fraction contains most of the chymotrypsin-like activity of leukocyte granules. Specific substrates are prepared for each enzyme, namely MeOSuc-Ala-Ala-Pro-Val-p-nitroanilide and Suc-Ala-Ala-Pro-Phe-p-nitroanilide. The latter is not hydrolyzed by leukocyte elastase. Enzyme preparations are assayed in 2.00 mL of 0.10M Hepes buffer, pH 7.5, containing 0.50M NaCl, 10% dimethylsulfoxide and 0.0020M Suc-Ala-Ala-Pro-Phe-p-nitroanilide as a substrate. Hydrolysis of the p-nitroanilide substrate is monitored at 405 nm and at 25°.

Useful dose range for the application of compounds of the present invention as neutrophil elastase inhibitors and as Cathepsin G inhibitors will of course depend upon the nature and severity of the disease state, as determined by the attending diagnostician, with the range of 0.01 to 10 mg/kg of body weight, per day, being useful for the aforementioned diseases states.

Compounds of the present invention that inhibit urokinase or plasminogen activator are potentially useful in treating excessive cell growth disease state. As such the compounds of the present invention may also be useful in the treatment of benign prostatic hypertrophy and prostatic carcinoma, the treatment of psoriasis, and in their use as abortifacients. For their end-use application, the potency and other biochemical parameters of the enzyme inhibiting characteristics of the compounds of the present invention are readily ascertained by standard biochemical techniques well-known in the art. Actual dose ranges for their specific end-use application will, of course, depend upon the nature and severity of the disease state of the patient or animal to be treated as determined by the attending diagnostician. It is to be expected that the general end-use application dose range will be about 0.01 to 10 mg per kg per day for an effective therapeutic effect.

Additional uses for compounds of the present invention include analysis of commercial reagent enzymes for active site concentration. For example, chymotrypsin is supplied as a standard reagent for use in clinical quantitation of chymotrypsin activity in pancreatic juices and feces. Such assays are diagnostic for gastrointestinal and pancreatic disorders. Pancreatic elastase is also supplied commercially as a reagent for quantitation of $\alpha_1$-antitrypsin in plasma. Plasma $\alpha_1$-antitrypsin increases in concentration during the course of several inflammatory diseases, and $\alpha_1$-antitrypsin deficiencies are associated with increased incidence of lung disease. Compounds of the present invention can be used to enhance the accuracy and reproducibility of this assay by titrametric standardization of the commercial elastase supplied as a reagent. See, U.S. Pat. No. 4,499,082.

Protease activity in certain protein extracts during purification of particular proteins is a recurring problem which can complicate and compromise the results of protein isolation procedures. Certain proteases present in such extracts can be inhibited during purification steps by compounds of the present invention, which bind tightly to various proteolytic enzymes.

The pharmaceutical compositions of the invention can be administered to any animal that can experience the beneficial effect, of the compounds of the invention. Foremost among such animals are humans, although the invention is not intended to be so limited.

The pharmaceutical compositions of the present invention can be administered by any means that achieve their intended purpose. For example, administration can be by parenteral, subcutaneous, intravenous, intramuscular, intraperitoneal, transdermal, buccal, or ocular routes. Alternatively, or concurrently, administration can be by the oral route. The dosage administered will be dependent upon the age, health, and weight of the recipient, kind of concurrent treatment, if any, frequency of treatment, and the nature of the effect desired.

In addition to the pharmacologically active compounds, the new pharmaceutical preparations can contain suitable pharmaceutically acceptable carriers comprising excipients and auxiliaries that facilitate processing of the active compounds into preparations that can be used pharmaceutically.

The pharmaceutical preparations of the present invention are manufactured in a manner that is, itself, known, for example, by means of conventional mixing, granulating, dragee-making, dissolving, or lyophilizing processes. Thus, pharmaceutical preparations for oral use can be obtained by combining the active compounds with solid excipients, optionally grinding the resulting mixture and processing the mixture of granules, after adding suitable auxiliaries, if desired or necessary, to obtain tablets or dragee cores.

Suitable excipients are, in particular, fillers such as saccharides, for example, lactose or sucrose, mannitol or sorbitol, cellulose preparations and/or calcium phosphates, for example, tricalcium phosphate or calcium hydrogen phosphate, as well as binders, such as, starch paste, using, for example, maize starch, wheat starch, rice starch, potato starch, gelatin, tragacanth, methyl cellulose, hydroxypropylmethylcellulose, sodium carboxymethylcellulose, and/or polyvinyl pyrrolidone. If desired, disintegrating agents can be added, such as, the above-mentioned starches and also carboxymethyl-starch, cross-linked polyvinyl pyrrolidone, agar, or alginic acid or a salt thereof, such as, sodium alginate. Auxiliaries are, above all, flow-regulating agents and lubricants, for example, silica, talc, stearic acid or salts thereof, such as, magnesium stearate or calcium stearate, and/or polyethylene glycol. Dragee cores are provided with suitable coatings that, if desired, are resistant to gastric juices. For this purpose, concentrated saccharide solutions can be used, which may optionally contain gum arabic, talc, polyvinyl pyrrolidone, polyethylene glycol, and/or titanium dioxide, lacquer solutions and suitable organic solvents or solvent mixtures. In order to produce coatings resistant to gastric juices, solutions of suitable cellulose preparations, such as, acetylcellulose phthalate or hydroxypropylmethyl-cellulose phthalate, are used. Dye stuffs or pigments can be added to the tablets or dragee coatings, for example, for identification or in order to characterize combinations of active compound doses.

Other pharmaceutical preparations which can be used orally include push-fit capsules made of gelatin, as well as soft, sealed capsules made of gelatin and a plasticizer, such as, glycerol or sorbitol. The push-fit capsules can contain the active compounds in the form of granules that may be mixed with fillers such as lactose, binders such as starches, and/or lubricants such as talc or magnesium stearate and, optionally, stabilizers. In soft capsules, the active compounds are preferably dissolved or suspended in suitable liquids, such as, fatty oils or liquid paraffin. In addition, stabilizers may be added.

Suitable formulations for parenteral administration include aqueous solutions of the active compounds in water-soluble form, for example, water-soluble salts, alkaline solutions and cyclodextrin inclusion complexes. Especially preferred alkaline salts are ammonium salts prepared, for example, with Tris, choline hydroxide, Bis-Tris propane, N-methylglucamine, or arginine. One or more modified or unmodified cyclodextrins can be employed to stabilize and increase the water solubility of compounds of the present invention. Useful cyclodextrins for this purpose are disclosed in U.S. Pat. Nos. 4,727,064, 4,764,604, and 5,024,998.

In addition, suspensions of the active compounds as appropriate oily injection suspensions can be administered. Suitable lipophilic solvents or vehicles include fatty oils, for example, sesame oil, or synthetic fatty acid esters, for example, ethyl oleate or triglycerides or polyethylene glycol-400 (the compounds are soluble in PEG-400). Aqueous injection suspensions can contain substances that increase the viscosity of the suspension, for example, sodium carboxymethyl cellulose, sorbitol, and/or dextran. Optionally, the suspension may also contain stabilizers.

The following examples are illustrative, but not limiting, of the method and compositions of the present invention. Other suitable modifications and adaptations of the variety of conditions and parameters normally encountered and obvious to those skilled in the art are within the spirit and scope of the invention.

EXAMPLE 1 a) 3-Benzyloxyphenyl acetate

Resorcinol monoacetate (6.10 g, 40 mmol) in DMF (10 mL) was added dropwise to a mixture of NaH (95%, 0.92 g, 40 mmol) in DMF (50 mL). The reaction mixture was stirred at room temperature for 10 min. Benzyl bromide (6.85 g, 40 mmol) in DMF (10 mL) was added dropwise and stirring was continued at room temperature for 2 h. The reaction was quenched carefully with water (100 mL) and then extracted with ethyl acetate (3×100 mL). The organic phase was washed with brine (2×50 mL), dried over $Na_2SO_4$, and concentrated in vacuo. The residue was then purified by flash column chromatography (1:1 hexane:methylene chloride) to give the title compound as a white solid (5.30 g, 55%). $^1$H-NMR (300 MHz, $CDCl_3$) δ 2.28 (s, 3H), 5.03 (s, 2H), 6.72 (m, 2H), 6.85 (dd, 1H), 7.27 (t, 1H), 7.41 (m, 5H).

b) 3-Benzyloxyphenol

3-Benzyloxyphenyl acetate (4.84 g, 20 mmol), as prepared in the preceding step, in tetrahydrofuran (50 mL) was treated with 1N NaOH (30 mL) for 3 h at room temperature. The mixture was acidified with 1N HCl and extracted into ethyl acetate (3×100 ML). The organic phase was washed with brine (2×50 mL), dried over $Na_2SO_4$, and concentrated in vacuo. The residue was then purified by flash column chromatography (methylene chloride) to give the title compound as a colorless liquid (3.80 g, 96%). $^1$H-NMR (300 MHz, $CDCl_3$) δ 5.01 (s, 2H), 5.09 (s, 1fH), 6.47 (m, 2H), 6.56 (dd, 1H), 7.11 (t, 1H), 7.39 (m, 5H).

c) 2-Chlorobenzenesulfonic acid 3-benzyloxyphenyl ester

To a solution of 3-benzyloxyphenol (2.97 g, 15 mmol), as prepared in the preceding step, in methylene chlorine (50 mL) at 0° C., was added N,N-diisopropylethylamine (2 mL) and 2-chlorobenzenesulfonyl chloride (3.27 g, 15.5 mmol). The reaction mixture was stirred at 0° C. for 2 h and at room temperature for 2 h. The reaction mixture was diluted with methylene chloride (200 mL), washed sequentially with saturated $NaHCO_3$ (2×50 mL) and brine (2×50 mL), dried over $Na_2SO_4$, and concentrated in vacuo. The residue was purified by flash column chromatography (1:1 hexane:methylene chloride) to give the title compound as a colorless liquid (5.35 g, 95%). $^1$H-NMR (300 MHz, $CDCl_3$) δ 4.97 (s, 2H), 6.71 (dd, 1H), 6.78 (t, 1H), 6.85 (dd, 1H), 7.17 (t, 1H), 7.37 (m, 5H) 7.58 (m, 2H), 7.91 (dd, 1H).

d) 2-Chlorobenzenesulfonicacid 3-hydrioxyphenyltester

A mixture of 2-chlorobenzenesulfonic acid 3-benzyloxyphenyl ester (3.75 g, 10 mmol), as prepared in the preceding step, and 10% palladium on carbon (350 mg) in tetrahydrofuran (80 mL) was hydrogenated (balloon) for 3 h. The catalyst was filtered through diatomaceous earth and washed with tetrahydrofuran. The combined tetrahydrofuran solutions were evaporated in vacuo. The residue was then purified by flash column chromatography (methylene chloride) to give the title compound as a colorless oil (2.75 g, 95%). $^1$H-NMR (300 MHz, $CDCl_3$) δ 6.68 (m, 3H), 7.12 (t, 1H), 7.37 (t, 1H), 7.60 (m, 2H), 7.94 (dd, 1H).

e) N-(tert-butoxycarbonyl)isonipecotic acid

Isonipecotic acid (3.90 g, 30 mmol), $NaHCO_3$ (5.05 g, 60 mmol) were dissolved in 1:1 1,4-dioxane:water (100 mL). Di-tert-butyl dicarbonate (6.55 g, 30 mmol) was added and the reaction mixture was stirred at room temperature overnight. The solvent was evaporated in vacuo. The residue was acidified to pH=6 using 10% citric acid and extracted into ethyl acetate (3×100 mL). The organic phase was then washed with brine (2×50 mL), dried over $Na_2SO_4$, and concentrated in vacuo to give the title compound as a white solid (6.25 g, 91%). $^1$H-NMR (300 MHz, $CDCl_3$) δ 1.43 (s, 9H), 1.63 (m, 2H), 1.88 (dd, 2H), 2.45 (m, 1H), 2.83 (t, 2H), 4.00 (d, 2H).

f) N-(tert-Butoxycarbonyl)-4-piperidinemethanol

N-(tert-butoxycarbonyl)-isonipecotic acid (5.73 g, 25 mmol), as prepared in the preceding step, was dissolved in tetrahydrofuran (50 mL) and cooled to 0° C. (ice-bath). Borane-tetrahydrofuran complex (1M, 25 mL, 25 mmol) was added slowly over 30 min. The reaction mixture was stirred at 0° C. overnight and then warmed up to room temperature for 6 h. Water (10 mL) was added slowly and then $K_2CO_3$ (5 g in 50 mL water) was added. The reaction mixture was extracted into ethyl acetate (3×50 mL). The organic phase was washed with saturated $NaHCO_3$ (2×50 mL), brine (2×50 mL), dried over $Na_2SO_4$, and concentrated in vacuo. The residue was then purified by flash column chromatography (1:1 hexane:ethyl acetate) to give the title compound as white crystals (4.55 g, 84%). 1H-NMR (300 MHz, $CDCl_3$) δ 1.13 (m, 2H), 1.42 (s, 9H), 1.67 (m, 4H), 2.67 (t, 2H), 3.46 (d, 2H), 4.09 (d, 2H).

g) N-(tert-butoxycarbonyl)-4-piperidineethyl methanesulfonate

To a solution of N-(tert-butoxycarbonyl)-4-piperidinemethanol (3.23 g, 15 mmol), as prepared in the preceding step, and triethylamine (2 mL) in methylene chloride (100 mL) at 0° C. was added slowly methanesulfonyl chloride (1.72 g, 15 mmol). The reaction mixture was stirred at 0° C. for 1 hour and then at room temperature for 2 h. The reaction mixture was diluted with methylene chloride (200 mL), washed sequentially with saturated $NaHCO_3$ (2×50 mL) and brine (2×50 mL), dried over $Na_2SO_4$, and concentrated in vacuo. The residue was purified by flash column chromatography (1:1 hexane:ethyl acetate) to give the title compound as a white solid (4.08 g, 93% yield). ¹H-NMR (300 MHz, CDCl₃) δ 1.24 (m, 2H), 1.46 (s, 9H), 1.75 (d, 2H), 1.92 (m, 1H), 2.71 (t, 2H), 3.02 (s, 3H), 4.07 (d, 2H), 4.13 (m, 2H).

h) 2-Chlorobenzenesulfonic acid 3-[[N-(tert-butoxycarbonyl)piperidin-4-yl]methoxy]phenyl ester To a solution of 2-chlorobenzenesulfonic acid 3-hydroxyphenyl ester (285 mg, 1.0 mmol), as prepared in step d, in DMF (5 mL) was added NaH (95%, 26 mg, 1.1 mmol). The reaction was stirred under nitrogen for 10 min. N-(tert-Butoxycarbonyl)-4-piperidinemethanol methanesulfonate (293 mg, 1.0 mmol), as prepared in the preceding step, was added and the reaction mixture was stirred at 50° C. under nitrogen for 3 h. The reaction mixture was then partitioned between water (50 mL) and ethyl acetate (150 mL). The organic phase was washed sequentially with saturated NaHCO₃ (2×50 mL) and brine (2×50 mL), dried over Na₂SO₄, and concentrated in vacuo. The residue was purified by flash column chromatography (2:1 hexane:ethyl acetate) to give the title compound as a colorless syrup (325 mg, 69%). ¹H-NMR (300 MHz, CDCl₃) δ 1.26 (m, 2H), 1.47 (s, 9H), 1.78 (d, 2H), 1.91 (m, 1H), 2.74 (t, 2H), 3.72 (d, 2H), 4.13 (m, 2H), 6.69 (m, 2H), 6.76 (dd, 1H), 7.16 (m, 1H), 7.37 (t, 1H), 7.62 (m, 2H), 7.95 (dd, 1H).

i) 2-Chlorobenzenesulfonic acid 3-[(piperidin-4-yl)methoxy]phenyl ester

2-Chlorobenzenesulfonic acid 3 -[[N-(tert-butoxycarbonyl)piperidin-4-yl]-methoxy]phenyl ester (565 mg, 1.2 mmol), as prepared in the preceding step, was treated with 30 mL of 4N HCl in 1,4-dioxan and stirred at room temperature for 2 h. After removing the solvent in vacuo, the residue was purified by flash column chromatography (5% methanol in methylene chloride to 5% methanol in methylene chloride saturated with NH₃) to give the title compound as a white foam (360 mg, 79%). ¹H-NMR (300 MHz, CDCl₃) δ 1.50 (m, 2H), 1.91 (m, 3H), 2.77 (t, 2H), 3.33 (d, 2H), 3.73 (d, 2H), 4.44 (bs, 1H), 6.69 (m, 2H), 6.77 (dd, 1H), 7.16 (t, 1H), 7.37 (t, 1H), 7.62 (m, 2H), 7.95 (dd, 1H). Mass spectrum (MALDI-TOF, sinapinic acid matrix) calcd. for C₁₈H₂₀NO₄SCl: 382.1 (M+H), 404.1 (M+Na). Found: 382.1, 404.5.

j) 2-Chlorobenzenesulfonic acid 3-[[1-(aminoiminomethyl)piperidin-4-yl]methoxy]phenyl ester A solution of 2-chlorobenzenesulfonic acid 3-[(piperidin-4-yl)methoxy]phenyl ester (191 mg, 0.5 mmol), as prepared in the preceding step, in DMF (10 mL) containing triethylamine (0.2 mL) and aminoiminomethanesulfonic acid (124 mg, 1.0 mmol) was stirred at room temperature overnight. The DMF was concentrated in vacuo and the residue was purified by flash column chromatography (90:10 methylene chloride:methanol saturated with NH₃) to give the title compound as a white foam (105 mg, 49%). ¹H-NMR (300 MHz, CDCl₃/DMSO)-d₆) δ 1.38 (m, 2H), 1.88 (d, 2H), 2.08 (m, 1H), 3.00 (t, 2H), 3.79 (d, 2H), 4.05 (dd, 2H), 6.61 (dd, 1H) 6.77 (t, 1H), 6.79 (dd, 1H), 7.20 (t, 1H), 7.37 (bs, 3H), 7.50 (m, 1H), 7.92 (d, 2H). Mass spectrum (MALDI-TOF, sinapinic acid matrix) calcd. for C₁₉H₂₂N₃O₄SCl: 424.1(M+H), 446.1 (M+Na). Found: 424.3, 446.6

EXAMPLE 2 a) N-(tert-Butoxycarbonyl)-3-piperidinemethanol

To a solution of 3-piperidinemethanol (4.60 g, 40 mmol) and triethylamine (6 mL) in 1,4-dioxane (100 mL) was added slowly di-tert-butyl dicarbonate (8.72 g, 40 mmol). After stirring at room temperature for 2 h, the solvent was then removed in vacuo and the residue was purified by flash column chromatography (2:1 hexane:ethyl acetate) to give the title compound as a white solid (7.81 g, 91%). ¹H-NMR (300 MHz, CDCl₃) δ 1.25–1.39 (m, 2H), 1.46 (s, 9H), 1.60–1.81 (m, 3H), 1.94 (bs, 1H), 2.98–3.08 (m, 2H), 3.51 (d, 2H), 3.66–3.77 (m, 2H).

b) N-(tert-Butoxycarbonyl)-3-piperidinemethanol methanesulfonate

To a solution of 14-(tert-butoxycarbonyl)-3-piperidinemethanol (3.23 g, 15 mmol), as prepared in the preceding step, and triethylamine (2 mL) in methylene chloride (100 mL) at 0° C. was added methanesulfonyl chloride (1.72 g, 15 mmol). After stirring at 0° C. for 1 hour, and then at room temperature for 2 h, the reaction mixture was diluted with methylene chloride (200 mL), washed sequentially with saturated NaHCO₃ (2×50 mL) and brine (2×50 mL), dried over Na₂SO₄, and concentrated in vacuo. The residue was purified by flash column chromatography (1:1 hexane:ethyl acetate) to give the title compound as a white solid (4.15 g, 94%). ¹H-NMR (300 MHz, CDCl₃) δ 1.29–1.38 (m, 2H), 1.46 (s, 1H), 1.64–1.98 (m, 3H), 2.80–2.97 (m, 2H), 3.03 (s, 3H), 3.79–3.93 (m, 2H), 4.10 (m, 2H).

c) 2-Chlorobenzenesulfonic acid 3-[[N-(tert-butoxycarbonyl)piperidin-3-yl]methoxy]phenyl ester To a solution of 2-chlorobenzenesulfonic acid 3-hydroxyphenyl ester (570 mg, 2.0 mmol), as prepared in step d of Example 1, in DMF (8 mL) was added NaH (95%, 53 mg, 2.2 mmol). The reaction mixture was stirred under nitrogen for 10 min. N-(tert-Butoxycarbonyl)-3-piperidinemethanol methanesulfonate (586 mg, 2.0 mmol), as prepared in step b, was added and the reaction mixture was stirred at 40° C. under nitrogen overnight. The reaction mixture was diluted with ethyl acetate (150 mL), washed sequentially with saturated NaHCO₃ (2×50 mL) and brine (2×50 mL), dried over Na₂SO₄, and concentrated in vacuo. The residue was purified by flash column chromatography (2:1 hexane:ethyl acetate) to give the title compound as a colorless syrup (510 mg, 54%). 1H-NMR (300 MHz, CDCl₃) δ 1.32 (m, 1H), 1.45 (s, 9H), 1.65–1.98 (m, 4H), 2.88 (m, 2H), 3.73 (m, 2H), 3.79 (d, 2H), 6.69 (m, 2H), 7.13 (t, 1H), 7.37 (t, 1H), 7.61 (m, 2H), 7.94 (d, 1H).

d) 2-Chlorobenzenesulfonic acid 3-[(piperidin-3-yl) methoxy]phenyl ester

2-Chlorobenzenesulfonic acid 3-[[N-(tert-butoxycarbonyl)piperidin-3-yl]-methoxy]phenyl ester (482 mg, 1.0 mmol), as prepared in the preceding step, was treated with 30 mL of 4N HCl in 1,4-dioxane and the reaction mixture was stirred at room temperature for 2 h. The solvent was removed in vacuo and the residue was purified by flash column chromatography (5% methanol in methylene chloride to 5% methanol in methylene chloride saturated with NH₃) to give the title compound as a white foam (315 mg, 82%). 1H-NMR (300 MHz, CDCl₃) δ 1.46 (t, 1H), 1.94 (m, 3H), 2.45 (bs, 1H), 2.79 (q, 2H), 3.51 (dd, 2H), 3.75 (t, 1H), 3.83 (t, 1H), 4.63 (bs, 1H), 6.69 (m, 2H), 6.74 (dd, 1H), 7.16 (t, 1H), 7.39 (t, 1H), 7.62 (m, 2H), 7.95 (dd, 1H). Mass spectrum (MALDI-TOF, sinapinic acid matrix) calcd. for C₁₈H₂₀NO₄SCl: 382.1 (M+H). Found: 382.3.

e) 2-Chlorobenzenesulfonic acid 3-[[1-(aminoiminomethyl)piperidin-3-yl]methoxy]-phenyl ester A solution of 2-chlorobenzenesulfonic acid 3-[(piperidin-3-yl)methoxyphenyl ester (191 mg, 0.5 mmol), as prepared in the preceding step, in DMF (10 mL) containing triethylamine (0.2 mL) and aminoiminomethanesulfonic acid (124 mg, 1.0 mmol) was stirred at room temperature overnight. The DMF was removed in vacuo and the residue was purified by flash column chromatography (90:10 methylene chloride:methanol saturated with NH₃) to give the title compound as a white foam (75 mg, 35%). 1H-NMR (300 MHz, DMSO-d₆) δ 1.42 (m, 2H), 1.70–1.98 (m, 3H), 2.96

(m, 2H), 3.82 (m, 4H), 6.62 (dd, 1H), 6.72 (t, 1H), 6.93 (dd, 1H), 7.29 (t, 1H), 7.39 (bs, 3H), 7.58 (dt, 1H), 7.87 (m, 3H). Mass spectrum (MALDI-TOF, sinapinic acid matrix) calcd. for $C_{19}H_{22}N_3O_4SCl$:442.1 (M+H). Found: 424.5.

EXAMPLE 3 a) 3-Benzyloxy-5-methylphenol

Orcinol monohydrate (7.10 g, 50 mmol) in DMF (20 mL) was added dropwise to NaH (95%, 2.4 g, 100 mmol) in DMF (60 mL). The reaction mixture was stirred at room temperature for 20 min. Benzyl bromide (8.55 g, 50 mmol) in DMF (20 mL was then added dropwise and the reaction mixture was stirred at room temperature for 2 h. Water (100 mL) was added slowly followed by extraction with ethyl acetate (3×100 mL). The organic phase was washed with brine (2×50 mL), dried over $Na_2SO_4$, and concentrated in vacuo. The residue was then purified by flash column chromatography (3:1 hexane:ethyl acetate) to give the title compound as a yellow oil (3.15 g, 31%). 1H-NMR (300 MHz, $CDCl_3$) 2.26 (s, 3H), 4.99 (s, 2H), 5.25 (s, 1H), 6.26 (s, 1H), 6.29 (t, 1H), 6.40 (s, 1H), 7.39 (m, 5H).

b) 2-Chlorobenzenesulfonic acid3-benzyloxy-5-methylphenylester. A solution of 3-benzyloxy-5-methylphenol (3.0 g, 15 mmol), as prepared in the preceding step, in methylene chloride (50 mL) at 0° C. was treated with N,N-diisopropylethylamine (2 mL) and 2-chlorobenzenesulfonyl chloride (3.27 g, 15.5 mmol). The reaction mixture was stirred at 0° C. for 2 h and at room temperature for 2 h. The reaction mixture was diluted with methylene chloride (200 mL), washed sequentially with saturated $NaHCO_3$ (2×50 mL) and brine (2×50 mL), dried over $Na_2SO_4$, and concentrated in vacuo. The residue was purified by flash column chromatography (1:1 hexane:methylene chloride) to give the title compound as a colorless liquid (5.10 g, 88%). $^1$H-NMR (300 MHz, $CDCl_3$) δ 2.24 (s, 3H), 4.93 (s, 2H), 6.55 (t, 1H), 6.57 (d, 1H), 6.68 (s, 1H), 7.36 (m, 6H), 7.58 (m, 2H), 7.94 (dd, 1H).

c) 2-Chlorobenzenesulfonic acid 3-hydroxy-5-methylphenyl ester

A mixture of 2-chlorobenzenesulfonic acid 3-benzyloxy-5-methylphenyl ester (4.66 g, 12 mmol), as prepared in the preceding step, and 10% palladium on carbon (500 mg) in tetrahydrofuran (80 mL) was hydrogenated (balloon) for 3 h. The catalyst was removed by filtration through diatomaceous earth (tetrahydrofuran washes) and the filtrate was concentrated in vacuo. The residue was purified by flash column chromatography (methylene chloride) to give the title compound as a pale-yellow solid (3.20 g, 89%. $^1$H-NMR (300 MHz, $CDCl_3$) δ 2.22 (s, 3H), 5.24 (s, 1H), 6.44 (t, 1H), 6.53 (d, 2H), 7.38 (dt, 1H), 7.60 (m, 2H), 7.96 (dd, 1H).

d) 2-Chlorobenzenesulfonic acid 3-[[N-(tert-butoxycarbonyl)piperidin-4-yl]methoxy]-5-methylphenyl ester A solution of 2-chlorobenzenesulfonic acid 3-hydroxy-5-methylphenyl ester (600 mg, 2.0 mmol), as prepared in the preceding step, N-(tert-butoxycarbonyl)-4-piperidinemethanol, as prepared in step f of Example 1, (430 mg, 2.0 mmol) and triphenylphosphine (525 mg, 2.0 mmol) in tetrahydrofuran (15 mL) at 0° C. was treated with diethyl azodicarboxylate (349 mg, 2.0 mmol). The reaction mixture was stirred at 0° C. for 2 h and at room temperature for 3 h. The reaction mixture was partitioned between ethyl acetate (200 mL) and water (50 mL). The organic extract was washed sequentially with saturated $NaHCO_3$ (2×50 mL) and brine (2×50 mL), dried over $Na_2SO_4$, and concentrated in vacuo. The residue was purified by flash column chromatography (2:1 ethyl acetate:hexane) to give the title compound as a colorless syrup (895 mg, 90%). $^1$H-NMR (300 MHz, $CDCl_3$) δ 1.24 (m, 2H), 1.47 (s, 9H), 1.80 (d, 2H), 1.89 (m, 1H), 2.24 (s, 3H), 2.72 (t, 2H), 3.68 (d, 2H), 4.13 (m, 2H), 6.47 (t, 1H), 6.52 (d, 1H), 6.58 (d, 1H), 7.38 (t, 1H), 7.61 (m, 2H), 7.97 (dd, 1H).

e) 2-Chlorobenzenesulfonic acid 3-[piperidin-4-yl)methyloxy]-5-methylphenyl ester 2-Chlorobenzenesulfonic acid 3-[[N-(tert-butoxycarbonyl)-piperidin-4-yl]methoxy]-5-methylphenyl ester (745 mg, 1.5 mmol), as prepared in the preceding step, was treated with 20 mL of 4N HCl in 1,4-dioxane and stirred at room temperature for 2 h. After removal of solvent in vacuo, the residue was purified by flash column chromatography (10% methanol in methane chloride saturated with NH3) to give the title compound as a colorless syrup (570 mg, 95%). $^1$H-NMR (300 MHz, $CDCl_3$) δ 1.45 (m, 1H), 1.94 (m, 3H), 2.23 (s, 3H), 2.45 (m, 1H), 2.80 (t, 2H), 3.51 (m, 2H), 3.76 (m, 2H), 6.46 (d, 1H), 6.55 (d, 2H), 7.40 (t, 1H), 7.62 (m, 2H), 7.97 (dd, 1H). Mass spectrum (MALDI-TOF, sinapinic acid matrix) calcd. for $C_{19}H_{22}NO_4SCl$: 396.1 (M+H). Found: 396.4 f) 2-Chlorobenzenesulfonic acid, 3-[[1-(aminoiminomethyl)piperidin-4-yl]methoxy]-5-methylphenyl ester A solution of 2-chlorobenzenesulfonic acid 3-[(piperidin-4-yl)methoxy]-5-methylphenyl ester (396 mg, 1.0 mmol), as prepared in the preceding step, in DMF (10 mL), N,N-diisopropylethylamine (0.5 mL) and aminoiminomethanesulfonic acid (248 mg, 2.0 mmol) was stirred at room temperature overnight. The DMF was removed in vacuo and the residue was purified by flash column chromatography (90:10 methylene chloride:methanol saturated with $NH_3$) to give the title compound as a white foam (159 mg, 36%). $^1$H-NMR (300 MHz, $CDCl_3$) δ 1.45 (m, 2H), 1.92 (m, 3H), 2.21 (s, 3H), 3.07 (t, 2H), 3.69 (d, 2H), 4.09 (d, 2H), 6.46 (d, 1H), 6.49 (s, 1H), 6.56 (s, 1H), 7.28 (s, 3H), 7.39 (t, 1H), 7.62 (m, 2H), 7.95 (dd, IH). Mass spectrum (MALDI-TOF, sinapinic acid matrix) calcd. for $C_{20}H_{24}N_3O_4SCl$: 438.1 (M+H), 460.1 (M+Na). Found: 438.3, 460.1.

EXAMPLE 4 a) 2-Chlorobenzenesulfonic acid 3-[[N-(tert-butoxycarbonyl)piperidin-3-yl]methoxy]-5-methylphenyl ester A solution of 2-chlorobenzenesulfonic acid 3-hydroxy-5-methylphenyl ester (600 mg, 2.0 mmol), as prepared in step c of Example 3, N-(tert-butoxycarbonyl)-3-piperidinemethanol (430 mg, 2.0 mmol), as prepared in step a of Example 2, and triphenylphosphine (525 mg, 2.0 mmol) in tetrahydrofuran (15 mL) at 0° C. was treated with diethyl azodicarboxylate (349 mg, 2.0 mmol). The reaction mixture stirred at 0° C. for 2 h and at room temperature for 3 h. Water (50 mL) was added and the reaction mixture was extracted into ethyl acetate (3×50 mL). The organic extract was washed sequentially with saturated $NaHCO_3$ (2×50 mL) and brine (2×50 mL), dried over $Na_2SO_4$, and concentrated in vacuo The residue was purified by flash column chromatography (2:1 ethyl acetate:hexane) to give the title compound as a colorless syrup (875 mg, 88%). $^1$H-NMR (300 MHz, $CDCl_3$) δ 1.28 (m, 1H), 1.45 (s, 9H), 1.64–1.96 (m, 4H), 2.23 (s, 3H), 2.87 (m, 2H), 3.69 (m, 2H), 3.90 (d, 2H), 6.46 (s, 1H), 6.52 (s, 1H), 6.58 (s, 1H), 7.40 (t, 1H), 7.62 (m, 2H), 7.96 (d, 1H).

b) 2-Chlorobenzenesulfonic acid 3-[(piperidin-3-yl)methoxy]-5-methylphenyl ester 2-Chlorobenzenesulfonic acid 3-[[N-(tert-butoxycarbonyl)piperidin-3-yl]methoxy]-5-methylphenyl ester (745 mg, 1.5 mmol), as prepared in the preceding step, was treated with 20 mL of 4N HCl in 1,4-dioxane at room temperature for 2 h. The solvent was removed in vacuo and the residue was purified by flash column chromatography (10% methanol in methylene chloride saturated with NH$_3$) to give the title compound as a colorless syrup (565 mg, 94%). $^1$H-NMR (300 MHz, CDCl$_3$) δ 1.45 (t, 1H), 1.94 (m, 3H), 2.23 (s, 3H), 2.45 (bs, 1H), 2.77 (t, 2H), 3.50 (dd, 2H), 3.76 (m, 2H), 6.46 (d, 1H), 6.55 (d, 2H), 7.40 (dd, 1H), 7.62 (m, 2H), 7.96 (dd, 1H). Mass spectrum (MALDI-TOF, sinapinic acid matrix) calcd. for C$_{19}$H$_{22}$NO$_4$SCl: 396.1 (M+H), 418.1 (M+Na). Found: 395.8, 418.2.

c) 2-chlorobenzenesulfonic acid 3-[[1-(aminoiminomethyl)piperidin-3-yl]methoxy-5-methylphenyl ester A solution of 2-chlorobenzenesulfonic acid 3-[(piperidin-3-yl)methoxy]-5-methylphenyl ester (396 mg, 1.0 mmol), as prepared in the preceding step, in DMF (10 mL) containing N,N-diisopropylethylamine (0.5 mL) and aminoiminomethanesulfonic acid (248 mg, 2.0 mmol) was stirred at room temperature overnight. The DMF was removed in vacuo and the residue was purified by flash column chromatography (90:10 methylene chloride:methanol saturated with NH$_3$) to give the title compound as a white foam (159 mg, 36%). $^1$H-NMR (300 MHz, CDCl$_3$) δ 1.45–1.92 (m, 4H), 2.11 (m, 1H), 2.23 (s, 3H), 3.07 (m, 2H), 3.81 (d, 2H), 3.92 (m, 2H), 6.50 (s, 2H), 6.61 (s, 1H), 7.24 (bs, 3H), 7.40 (m, 1H), 7.63 (m, 2H), 7.95 (dd, 1H). Mass spectrum (MALDI-TOF, sinapinic acid matrix) calcd. for C$_{20}$H$_{24}$N$_3$O$_4$SCl: 438.1 (M+H), 460.1 (M+Na). Found: 438.5, 460.5.

EXAMPLE 5 a) N-(tert-Butoxycarbonyl)-1-(2-hydroxyethyl)piperazine

To a solution of 1-(2-hydroxyethyl)piperazine (5.20 g, 40 mmol) and triethylamine (6 mL) in 1,4-dioxane (100 mL) was added slowly di-tert-butyl dicarbonate (8.72 g, 40 mmol). The reaction mixture was stirred at room temperature for 2 h. The solvent was removed in vacuo and the residue was purified by flash column chromatography (ethyl acetate to 2% methanol in ethyl acetate) to give the title compound as a colorless oil (8.32 g, 90%). $^1$ H-NMR (300 MHz, CDCl$_3$) δ 1.46 (s, 9H), 2.46 (t, 4H), 2.55 (t, 2H), 2.75 (bs, 1H), 3.44 (t, 4H), 3.63 (t, 2H).

b) 2-Chlorobenzenesulfonic acid 3-[2-[N-(tert-butoxycarbonyl)piperazin-4-yl]ethoxy]phenyl ester To a solution of 2-chlorobenzenesulfonic acid 3-hydroxyphenyl ester (570 mg, 2.0 mmol), as prepared in step d of Example 1, N-(tert-butoxycarbonyl)-1-(2-hydroxyethyl)piperazine (507 mg, 2.2 mmol), as prepared in the preceding step, and triphenylphosphine (525 mg, 2.0 mmol) in tetrahydrofuran (15 mL) at 0° C. was added diethyl azodicarboxylate (349 mg, 2.0 mmol). After stirring at 0° C. for 2 h and at room temperature for 3 h, water (50 mL) was added. The reaction mixture was extracted into ethyl acetate (3×50 mL) and washed sequentially with saturated NaHCO$_3$ (2×50 mL) and brine (2×50 mL), dried over Na$_2$SO$_4$, and concentrated in vacuo. The residue was purified by flash column chromatography (1:1 ethyl acetate:hexane) to give the title compound as a white solid (875 mg, 85%). $^1$H-NMR (300 MHz, CDCl$_3$) δ 1.47 (s, 9H), 2.49 (t, 4H), 2.77 (t, 2H), 3.45 (t, 4H), 4.02 (t, 2H), 6.72 (m, 2H), 6.78 (dd, 1H), 7.16 (t, 1H), 7.37 (dt, 1H), 7.61 (m, 2H), 7.95 (dd, 1H).

c) 2-Chlorobenzenesulfonic acid 3-[2-(piperazin-1-yl)ethoxy]phenyl ester

2-Chlorobenzenesulfonic acid 3-[2-[N-(tert-butoxycarbonyl)piperazin-4-yl]ethoxy]phenyl ester (994 mg, 2.0 mmol), as prepared in the preceding step, was treated with 4N HCl (40 mL in 1,4-dioxane) and stirred at room temperature for 2 h. After concentrating in vacuo, the residue was purified by flash column chromatography (10% methanol in methylene chloride saturated with NH$_3$) to give the title compound as a white foam (705 mg, 88%). $^1$H-NMR (300 MHz, CDCl$_3$) δ 2.00 (bs, 1H), 2.54 (t, 4H), 2.76 (t, 2H), 2.93 (t, 4H), 4.02 (t, 2H), 6.72 (m, 2H), 6.78 (dd, 1H), 7.16 (t, 1H), 7.37 (dt, 1H), 7.61 (m, 2H), 7.95 (dd, 1H). Mass spectrum MALDI-TOF, sinapinic acid matrix) calcd. for C$_{18}$H$_{21}$N$_2$O$_4$SCl: 397.1 (M+H). Found: 397.6.

d) 2-Chlorobenzenesulfonic acid 3-[2-[1-(aminoiminomethyl)piperazin-4-yl]ethoxy]phenyl ester diacetic acid salt A solution of 2-chlorobenzenesulfonic acid 3-[(piperazin-4-yl)ethoxy]phenyl ester (397 mg, 1.0 mmol), as prepared in the preceding step, N,N-diisopropylethylamine (0.5 mL) and aminoiminomethanesulfonic acid (248 mg, 2.0 mmol) in DMF (10 mL) was stirred at room temperature overnight. The DMF was removed in vacuo and residue was purified by flash column chromatography (85:15:2 methylene chloride:methanol:acetic acid) to give the title compound as a white solid (290 mg, 52%). $^1$H-NMR (300 MHz, CDCl$_3$/CD$_3$OD) δ 2.01 (bs, 6H), 2.64 (t, 4H), 2.84 (t, 2H), 3.45 (t, 4H), 4.07 (t, 2H), 6.67 (dd, 1H), 6.77 (t, 1H), 6.83 (dd, 1H), 7.19 (t, 1H), 7.41 (dt, 1H), 7.65 (t, 2H), 7.95 (dd, 1H). Mass spectrum (MALDI-TOF, sinapinic acid matrix) calcd. for C$_{19}$H$_{23}$N$_4$O$_4$SCl: 439.1(M+H), 461.1 (M+Na). Found: 438.8, 460.8.

EXAMPLE 6 a) 2-Chlorobenzenesulfonic acid 3-[2-[N-(tert-butoxycarbonyl)piperazin-4-yl]ethoxy]-5-methylphenyl ester A solution of 2-chlorobenzenesulfonic acid 3-hydroxy-5-methylphenyl ester (600 mg, 2.0 mmol), as prepared in step c of Example 3, N-(tert-butoxycarbonyl)-1-(2-hydroxyethyl)piperazine (461 mg, 2.0 mmol), as prepared in step a of Example 5, and triphenylphosphine (525 mg, 2.0 mmol) in tetrahydrofuran (15 mL) at 0 ° C. was treated with diethyl azodicarboxylate (349 mg, 2.0 mmol). The reaction mixture was stirred at 0° C. for 2 h and at room temperature for 3 h. Water (50 mL), was added. The reaction mixture was extracted into ethyl acetate (3×50 mL), washed sequentially with saturated NaHCO$_3$ (2×50 mL) and brine (2×50 mL), dried over Na$_2$SO$_4$, and concentrated in vacuo. The residue was purified by flash column chromatography (1:2 ethyl acetate:hexane) to give the title compound as a white solid (885 mg, 85%). $^1$H-NMF, (300 MHz, CDCl$_3$) δ 1.47 (s, 9H), 2.23 (s, 3H), 2.48 (t, 4H), 2.75 (t, 2H), 3.44 (t, 4H), 3.99 (t, 2H), 6.50 (t, 1H), 6.54 (s, 1H), 6.60 (s, 1H), 7.37 (dt, 1H), 7.61 (m, 2H), 7.95 (dd, 1H).

b) 2-Chlorobenzenesulfonic acid 3-[2-(piperazin-4-yl)ethoxy]-5-methylphenyl ester 2-Chlorobenzenesulfonic acid 3-[[N-(tert-butoxycarbonyl)-piperazin-4-yl]ethoxy]-5-methylphenyl ester (1.02 g, 2.0 mmol), as prepared in the preceding step, was treated with 40 mL of 4N HCl in 1,4-dioxane at room temperature for 2 h. The solvent was removed in vacuo and the residue was purified by flash column chromatography (10% methanol in methylene chloride saturated with NH3) to give the title compound as a pale-yellow liquid (695 mg, 84%). $^1$H-NMR (300 MHz, CDCl$_3$): δ 1.92 (bs, 2H), 2.24 (s, 3H), 2.53 (d, 3 H), 2.73 (t, 2H), 2.92 (t, 4H), 3.98 (t, 2H), 6.50 (t, 1H), 6.54 (t, 1H), 6.61 (t, 1H) 7.38 (dt, 1H), 7.62 (m, 2H), 7.97 (dd, 1H).

c) 2-Chlorobenzenesulfonic acid 3-[2-[1-(aminoiminomethyl)piperazin-4-yl]ethoxy]-5-methylphenyl ester diacetic acid salt A solution of 2-chlorobenzenesulfonic acid 3-[2-(piperazin-4-yl)ethoxy]-5-methylphenyl ester (411 mg, 1.0 mmol), as prepared in the preceding step, in DMF (10 mL)

containing N,N-diisopropylethylamine (0.5 mL) and aminoiminomethanesulfonic acid (248 mg, 2.0 mmol) was stirred at room temperature overnight. The DMF was removed in vacuo and the residue was purified by flash column chromatography (85:15:2 methylene chloride:methanol:acetic acid) to give the title compound as a white solid (295 mg, 51%). $^1$H-NMR (300 MHz, CDCl$_3$) δ 1.95 (s, 6H), 2.23 (s, 3H), 2.61 (t, 4H), 2.78 (t, 2H), 3.48 (t, 4H), 3.99 (t, 2H), 6.52 (s, 2H), 6.59 (s, 1H), 7.39 (dt, 1H), 7.62 (m, 2H), 7.96 (dd, 1H). Mass spectrum (MALDI-TOF, sinapinic acid matrix) calcd. for C$_{20}$H$_{25}$N$_4$O$_4$SCl: 453.1(M+H), 475.1 (M+Na). Found: 452.7, 474.9.

EXAMPLE 7 a) 2-Chlorobenzenesulfonic acid 3-hydroxy-5-carbomethoxyphenyl ester

2-Chlorobenzenesulfonyl chloride (2.49 g, 0.018 mol) was added dropwise to a rapidly stirred mixture of methyl 3,5-dihydroxybenzoate in saturated sodium bicarbonate (20 mL) and diethyl ether (20 mL) and allowed to stir at ambient temperature. After 2 days, 1.25 g of 2-chlorobenzenesulfonyl chloride was added and stirred for an additional 1 day. The reaction mixture was diluted with methylene chloride and separated. The aqueous layer was extracted with methylene chloride. The combined methylene chloride extracts were washed with brine and water, dried, and evaporated to an oil. The oil was triturated with hexanes (4 times) before placing the residual oil on a silica gel column and eluted first with methylene chloride, then 10% ethyl acetate/methylene chloride. The appropriate fractions were evaporated to give 1.35 g of solid.

b) 2-Chlorobenzenesulfonic acid 3-[[1-N-(tert-butoxycarbonyl)piperidin-4-yl]methoxy]-5-carbomethoxyphenyl ester A solution of triphenylphosphine (0.249 g, 0.95 mol) in tetrahydrofuran (20 mL) was treated with diethyl azodicarboxylate (0.131 mL, 0.83 mol) and allowed to stir at ambient temperature for 15 min. before the addition of 2-chlorobenzenesulfonic acid 3-hydroxy-5-carbomethoxyphenyl ester (0.25 g, 0.73 mol), as prepared in the preceding step, in tetrahydrofuran (5 mL) and N-tert-butoxycarbonyl-4-piperidinemethanol (0.165 g, 0.77 mol), as prepared in step f of Example 1. The reaction mixture was allowed to stir at ambient temperature overnight. The solvent was evaporated and treated with ether/hexane to produce a crystalline material, which was separated by filtration. The filtrate was evaporated to an oil, placed on a silica gel column, and eluted with 20% ethyl acetate/hexane. The appropriate fractions were evaporated to give 0.14 g of material. 1H-NMR (CDCl$_3$; 300 MHz): δ 1.25 (m, 3H), 1.47 (s, 9H), 1.78 (m, 2H), 2.74 (t, 2H), 3.77 (d, 2H), 3.88 (s, 3H), 4.12 (m, 2H), 6.90 (t, 1H), 7.38 (m, 3H), 7.62 (m, 2H), 7.97 (m, 1H).

c) 2- Chlorobenzenesulfonic acid 3-[[1-(aminoiminomethyl) piperidin-4-yl]methoxy]-5-carbomethoxyphenyl ester 2-Chlorobenzenesulfonic acid 3 -[[1-N-(tert-butoxycarbonyl)piperidin-4-yl]methoxy]-5-carbomethoxyphenyl ester (0.14 g, 0.26 mmol), as prepared in the preceding step, was treated with 2.5 mL of 25% trifluoroacetic acid in methylene chloride at ambient temperature for 15 min. The solvent was evaporated, the residue was azeotroped with acetonitrile (2 times), and placed under high vacuum. The residue was dissolved in methanol (3 mL) and treated with 1H-pyrazole-1-carboxamidine hydrochloride (0.057 g, 0.39 mmol) and N,N-diisopropylethylamine (0.136 mL, 0.78 mmol). The reaction mixture was stirred at ambient temperature overnight. An additional portion of 1H-pyrazole-1-carboxamidine hydrochloride (10 mg) was added to the reaction mixture and then was stirred for 6 h. The solvent was evaporated to dryness. The residue was triturated with hexane and ether. The residue was dissolved in acetonitrile and diluted with diethylether to produce a crystalline crop, which was collected by filtration to give 25.3 mg of solid. $^1$H-NMR (CDCl$_3$; 300 MHz): δ 1.44–1.55 (m, 2H), 1.95–2.1 (m, 3H ), 3.11 (t, 2H ), 3.81 (d, 2H), 3.87 (s, 3H), 4.07 (d, 2H), 6.90 (t, 1H), 7.38 (m, 5H), 7.64 (m, 2H), 7.96 (m, 1H). Mass spectrum MADLDI-TOF) calcd. for C$_{21}$H$_{24}$N$_3$O$_6$SCl: 482.1 (M+H). Found 483.5.

EXAMPLE 8 a) 3-(2-Chlorobenzyloxy)-5-methylphenol

To 1.31 g (9.22 [mmol) of Orcinol monohydrate in 20 mL anhydrous DMF under a nitrogen atmosphere was add ed 220 mg (9.17 mmol) of NaH (100%). After 5 min, 1.3 mL (100 mmol) of 2-chlorobenzyl bromide was added. The reaction mixture was stirred for 2 h and then quenched with 1N HCl. The reaction mixture was extracted into ethyl acetate (200 mL). The organic phase was washed with H$_2$O (4×100 mL), dried (MgSO$_4$), and concentrated in vacuo. Purification by flash chromatography (ether/hexane (50:50 to 100:0) gave 656 mg of the title compound as a hardened oil. $^1$H-NMR (300 MHz, CDCl$_3$) δ 7.54 (dd, 1H, J=3, 7 Hz), 7.39 (dd, 1H, J=3, 7 Hz), 7.2 –7.3 (m, 2H), 6.41 (s, 1H), 6.29–6:30 (m, 2H), 5.29 (s, 2H), and 2.28 (s, 3H).

b) 3-(2-Chlorobenzyloxy)-5-|1-N-(tert-butoxycarbonyl) piperidin-4-yl]toluene

To 177 mg (0.823 mmol) of N-tert-butoxycarbonyl-4-piperidinemethanol, as prepared in step f of Example 1, 195 mg (0.785 mmol) of 3-(2-chlorobenzyloxy)-5-methylphenol, as prepared in the preceding step, 262 mg (1.02 mmol) of triphenylphosphine, and 250 μL (2.27 mmol) of N-methylmorpholine in 3 mL of tetrahydrofuran was added 140 μL (0.892 mmol) of diethyl azodicarboxylate. The reaction mixture was stirred overnight, quenched with saturated NaCl (50 mL), and extracted into ethyl acetate (50 mL). The organic extract was dried (MgSO$_4$), and the product was partially purified by flash chromatography (ethyl acetate/hexane (1:4)), to give 230 mg of impure title compound (contaminated with 3-(2-chlorobenzyloxy)-5-methylphenol). This material was used as is in the next reaction.

c) 3-(2-Chlorobenzyloxy)-5-[[piperidin-4-yl]methoxy] toluene

A solution of 230 mg of impure 3-(2-chlorobenzyloxy)-5-[1-N-(tert-butoxycarbonyl)piperidiny-4-yl]toluene, prepared in the preceding step, in methylene chloride (1 mL) was added 2 mL of 4N HCl/dioxane solution. After 3 h, the reaction mixture was quenched with excess 1N NaOH, extracted into ether (100 mL), dried (MgSO$_4$), and then purified by flash chromatography (ether/methylene chloride/ methanol/NH$_4$OH (50:4:3:5:2) then methylene chloride/ methanol/NH$_4$OH (85:10:5)) to give 153 mg of the title compound as an oil. $^1$H-NMR (300 MHz, CDCl$_3$) δ 7.56 (dd, 1H, J=3, 7 Hz), 7.39 (dd, 1H, J=3, 7 Hz), 7.2–7.3 (m, 2H), 6.42 (s, 1H), 6.36 (s, 2H), (5.12 (s, 2H), 3.76 (d, 2 H), 3.12 (dt, 2H), 2.64 (dt, 2H, J=2.5, 12 Hz), 1.7–2.0 (m, 3H). Mass spectrum (MALDI-TOF; gentisic acid matrix) calcd. for C$_{20}$H$_{24}$ClNO$_2$: 346.2 (M+H). Found: 346.8.

d) 3-(2-Chlorobenzyloxy)-5-[[(1-aminoiminomethyl) piperidin-4-yl]methoxy|toluene acetic acid salt A solution of 132 mg of 3-(2-chlorobenzyloxy)-5-[[piperidiny-4-yl]methoxy]toluene prepared in the preceding step, 2 mL of DMF, 300 μL (2.1 mmol) of N,N-diisopropylethylamine, and 124 mg (0.846 mmol) of 1H-pyrazole-1-carboxamidine hydrochloride was stirred for 2 days at ambient temperature. The reaction mixture was quenched with 1N NaOH, extracted into methylene chloride, dried (K$_2$CO$_3$), and concentrated in vacuo. Purification by chromatography over a 10 g Water's Associates 10 g silica Sep-Pak cartridge using elutions of methylene chloride/methanol/acetic acid (89:9.8:1.2 to 78:19.6:2.4) gave 101 mg of the title compound as a colorless solid after removal of solvent. $^1$H-NMR (300 MHz, CD$_3$OD) δ 7.73–7.56 (m, 1H), 7.40–7.45 (m, 1H), 7.30–7.35 (m, 3H), 6.43 (s, 1H), 6.37 (s, 1H), 6.34 (t, 1H, J=5.12 (s, 2H)), 3.93 (d, 2H), 3.84 (d, 2H), 3.12 (dt, 2H, J=2.5, 13 Hz), 2.0–2.25 (m, 2H), 1.9 (s, 3H), 1.25–1.55 (m, 2H). Mass spectrum (MALDI-TOF; gentisic acid matrix) calcd. for C$_{21}$H$_{26}$N$_3$ClO$_3$: 388.2 (M+H). Found: 387.6.

EXAMPLE 9

The following compound was synthesized using a process analogous to Example 8:

3-(2-Chlorobenzyloxy)-1-[[(1-aminoiminomethyl) piperidin-4-yl]methoxy]benzene acetic acid salt $^1$H-NMR (300 MHz, DMSO-d$_6$) δ 7.45 (dd, 1H), 7.22–7.32 (m, 3H), 6.89–7.20 (m, 4 H), 3.88 (d, 2H), 2.97 (t, 2H), 1.7–2.5 (m, 1H), 1.23–1.31 (m, 2H). Mass spectrum (MALDI-TOF; α-cyano-4-hydroxycinnamic acid matrix) calcd. for C$_{20}$H$_{24}$ClN$_3$O$_2$: 374.2 (M+H). Found: 374.0.

EXAMPLE 10 a) 2-[(4-(tert-butoxycarbonylamino)butyloxy]-4-methylnitrobenzene

To 252 mg (1.33 mmol) 4-(tert-butoxycarbonylamino) butanol, 407 mg (2.66 mmol) of 4-methyl-2-nitrophenol and 383 mg (1.46 mmol) of triphenylphosphine in 1.0 mL of anhydrous tetrahydrofuran under nitrogen was added 336 mL (1.46 mmol) of diethyl azodicarboxylate. After stirring for 1 h, the mixture was concentrated to a yellow syrup. Chromatography on a Waters Associates 10 g silica Sep-Pak SPE column eluting with 10-12% ethyl acetate-hexane afforded 422 mg (98%) of the title compound as a colorless oil. $^1$H-NMR (300 MHz, CDCl$_3$) δ 7.64 (d, 1H, J=2.0 Hz), 7.30 (dd, 1H, J=8.5, 2.2 Hz), 6.95 (d, 1H, J=8.5 Hz), 4.64 (br s, 1H), 4.09 (t, 2H, J=6.1 Hz), 3.19 (q, 2H, J=6.5 Hz), 2.34 (s, 3H), 1.86 (m, 2H), 1.69 (m, 2H), 1.44 (s, 9H). Mass spectrum (MALDI-TOF, gentisic acid matrix) calcd. for C$_{16}$H$_{24}$N$_2$O$_5$: 347.2 (M+H). Found: 347.3.

b) 2-[(4-(tert-butoxycarbonylamino)butyloxy]-4-methylaniline

To a solution of 390 mg (1.20 mmol) of 2-[(4-(tert-butoxycarbonylamino)butyloxy]-4-methylnitrobenzene in 1.5 mL of tetrahydrofuran was added 39 mg of 10% palladium on carbon and the mixture stirred under a balloon of hydrogen for 20 h. The mixture was filtered (diatomaceous earth) washing with 3 mL of tetrahydrofuran and concentrated to 339 mg (96%) of the title compound as a colorless oil. $^1$H-NMR (300 MHz, CDCl$_3$) δ 6.66 (d, 1H, J=8.0 Hz), 6.55 (dd, 1H, J=2.0 Hz), 6.49 (d, 1H, J=8.0 Hz), 4.59 (br s, 1H), 3.98 (t, 2H, J=6.3 Hz), 3.19 (q, 2H, J=6.6 Hz), 2.21 (s, 3H), 1.82 (m, 2H), 1.67 (m, 2H), 1.57 (br s, 2H), 1.44 (s, 9H). Mass spectrum (MALDI-TOF, gentisic acid matrix) calcd. for C$_{16}$H$_{26}$N$_2$O$_3$: 317.2 (M+Na). Found: 317.2.

c) N-[2-[4-(tert-butoxycarbonylamino)butyloxy]-4-methylphenyl]benzenesulfonamide To 216 mg ( 0.734 mmol) of 2-[(4-(tert-butoxycarbonylamino)butyloxy]-4-methylaniline and 101 mL (0.918 mmol) of 4-methylmorpholine in 3.0 mL of dichloromethane was added 143 mL (0.807 mmol) of benzenesulfonyl chloride. The solution was stirred for 45 min, diluted with 30 mL of dichloromethane and washed with 10% citric acid (2×30 mL), saturated NaHCO$_3$ (2×30 mL) and brine (30 mL). The solution was dried (Na$_2$SO$_4$) and concentrated to 342 mg of a faintly amber solid. Chromatography on a Waters Associates 10 g silica Sep-Pak SPE column eluting with dichloromethane followed by 4% ethyl acetate-dichloromethane afforded 282 mg (88%) of the title compound as a white crystalline solid. $^1$H-NMR (300 MHz, CDCl$_3$) δ 7.72 (m, 2H), 7.50 (m, 1H), 7.40 (m, 3H), 6.94 (s, 1H), 6.83 (dd, 1H, J=8.3, 2.1 Hz), 6.59 (d, 1H, J=8.3 Hz), 4.54 (br s, 1H), 3.70 (t, 2H, J=6.3 Hz), 3.19 (q, 2H, J=6.5 Hz), 2.27 (s, 3H), 1.62 (m, 2H), 1.48 (m, 2H), 1.46 (s, 9H). Mass spectrum (MALDI-TOF, gentisic acid matrix) calcd. for C$_{22}$H$_{30}$N$_2$O$_5$S: 457.2 (M+Na). Found: 457.7.

d) N-methyl-N-[2-[4-(tert-butoxycarbonylamino)butyloxy]-4-methylphenyl]benzenesulfonamide To a solution of 176 mg (0.405 mmol) of N-[2-[4-(tert-butoxycarbonylamino)butyloxy]-4-methylphenyl] benzenesulfonamide in 1.5 mL of anhydrous DMF was added 78.4 mg (0.567 mmol) of powdered anhydrous potassium carbonate and 28 mL (0.446 mmol) of iodomethane. After stirring for 18 h, the mixture was partitioned between 20 mL of ethyl acetate and 20 mL of water. The organic layer was washed with water (2×15 mL), brine (15 mL), dried (Na$_2$SO$_4$) and concentrated to give 180 mg (99%) of the title compound as a colorless syrup. $^1$H-NMR (300 MHz, CDCl$_3$) δ 7.70 (m, 2H), 7.56 (m, 1H), 7.46 (m, 2H), 7.14 (d, 1H, J=2.2 Hz), 7.05 (dd, 1H, J=8.4, 2.2 Hz), 6.68 (d, 1H, J=8.4), 4.53 (br s, 1H), 3.61 (t, 2H, J=6.0 Hz), 3.19 (s, 3H), 3.06 (q, 2H, J=6.3 Hz), 2.28 (s, 3H), 1.46 (s, 9H), 1.30–1.41 (m, 4H). Mass spectrum (MALDI-TOF, gentisic acid matrix) calcd. for C$_{23}$H$_{32}$N$_2$O$_5$S: 349.2 (M-BOC+2H). Found: 349.8.

e) N-methyl-N-[2-[(4-aminoiminomethylamino)butyloxy]-4-methylphenyl]benzenesulfonamide, acetic acid salt To a solution of 173 mg (0.386 mmol) of N-methyl-N-[2-[4-(tert-butoxycarbonylamino)butyloxy]-4-methylphenyl]benzenesulfonamide in 3.0 mL of anhydrous dichloromethane was added 0.75 mL of trifluoroacetic acid. After stirring for 20 min, the solution was concentrated and placed under vacuum (0.1 torr/1 h) to afford 220 mg of a colorless oil. 208 mg of this residue in 2.0 mL of anhydrous DMF was treated with 113 mg (0.772 mmol) of 1H-pyrazole-1-carboxamide hydrochloride and 202 mL (1.16 mmol) of N,N-diisopropylethylamine and the mixture stirred for 15 h. Water (25 mL) was added and the mixture extracted with ethyl acetate (10 mL). 1M potassium carbonate (10 mL) was added and the mixture again extracted with ethyl acetate (2×15 mL). The combined extracts were washed with 1M potassium carbonate (15 mL), brine (15 mL), dried (Na$_2$SO$_4$) and concentrated to 214 mg of a colorless resin. Chromatography on a Waters Associates 10 g silica Sep-Pak SPE column eluting with a gradient of 1:10:90 to 2:20:80 of acetic acid:methanol:dichloromethane to afford 95 mg of nearly pure title compound as a colorless resin and 148 mg of the title compound contaminated with 1H-pyrazole-1-carboxamide. The purer material was crystallized by addition of a solution of the residue in 0.8 mL of acetic acid-methanol (1:1) to 25 mL of ether. After 2.5 days, the solid was collected to afford 51.9 mg (30%) of the title compound as white crystals. $^1$H-NMR (300 MHz, CD$_3$OD/DMSO-d$_6$, 3:1) δ 7.66 (m, 3 H), 7.55 (m, 2H), 7.11 (dd, 1H, J=8.4, 2.0 Hz), 6.96 (d, 1H, J=2.0 Hz), 6.86 (d, 1H, J=8.4 Hz), 3.73 (t, 2H, J=6.0 Hz), 3.17 (s, 3H), 3.15 (t, 2H, J=7.0 Hz), 2.24 (s, 3H), 1.88 (s, 3H+xs HOAc), 1.39–1.88 (m, 4H). Mass spectrum (MALDI-TOF, gentisic acid matrix) calcd. for C$_{19}$H$_{26}$N$_4$O$_3$S: 391.2 (M+H). Found: 391.1.

EXAMPLE 11 a) N-(3-nitrophenyl)benzenesulfonamide

To 6.17 g (44.7 mmol) of 3-nitroaniline and 8.41 mL (48.2 mmol) of N,N-diisopropylethylamine in 150 mL of anhydrous ether was added 5.14 mL (40.2 mmol) of benzenesulfonyl chloride. The mixture was heated to reflux under nitrogen with stirring for 16 h, cooled and the resulting two-phase mixture scratched to crystallize the insoluble oil. After decanting the ether layer, the derived solid was dissolved in 300 mL of dichloromethane and the solution washed with 2N HCl (3×200 mL), saturated NaHCO$_3$ (200 mL), brine (200 mL), dried (Na$_2$SO$_4$) and concentrated to give 9.62 g (86%) of the title compound as a light tan solid. $^1$H-NMR (300 MHz, CDCl$_3$) δ 7.96 (m, 2H), 7.86 (m, 2H), 7.41–7.63 (m, 5H), 7.30 (br s, 1H). Mass spectrum (MALDI-TOF, gentisic acid matrix) calcd. for C$_{12}$H$_{10}$N$_2$O$_4$S: 301.0 (M+Na). Found: 301.1.

b) N-benzyl-N-(3-nitrophenyl)benzenesulfonamide

To 6.00 g (21.6 mmol) of N-(3-nitrophenyl)benzenesulfonamide in 15 mL of anhydrous N,N-dimethylformamide at under nitrogen was added 4.48 g (32.4 mmol) of powdered anhydrous potassium carbonate and 2.83 mL (23.8 mmol) of benzyl bromide. After stirring for 3.5 h, the mixture was partitioned between 200 mL of ethyl acetate and 250 mL of water. The aqueous layer was extracted with 50 mL of ethyl acetate and the combined organic phases washed with 1M K$_2$CO$_3$ (2×100 mL). 50 mL of hexane was added to the organic phase which was then washed with water (3×150 mL), brine (100 mL), dried (Na$_2$SO$_4$) and concentrated to give 8.2 g of a crystalline yellow solid. Recrystallization from ethyl acetatehexane afforded 7.45 g (94%) of the title compound is cream-colored crystals. $^1$H-NMR (300 MHz, CDCl$_3$) δ 8.06 (d, 1H, J=7.4 Hz), 7.76 (s, 1H), 7.64–7.67 (m, 3H), 7.51–7.56 (m, 2H), 7.38–7.46 (m, 2H), 7.21 (s, 5H), 4.77 (s, 2H). Mass spectrum (MALDI-TOF, gentisic acid matrix) calcd. for C$_{19}$H$_{16}$N$_2$O$_4$S: 369.1 (M+H), 391.1 (M+Na), 407.0 (M+K). Found: 368.8, 391.3, 407.4.

c) N-benzyl-N-(3-aminophenyl)benzenesulfonamide

To 3.01 g (8.17 mmol) of N-benzyl-N-(3-nitrophenyl)benzenesulfonamide in 60 mL of methanol-tetrahydrofuran (1:1) was added 200 mg of 10% palladium on carbon. After stirring the mixture under a balloon of hydrogen for 1.7 h, an additional 200 mg of 10% palladium on carbon was added and stirring was continued for another 2.5 h. Filtration (diatomaceous earth) and concentration afforded a dark green resin which was dissolved in 40 mL of ethyl acetal:e:hexane (1:1), refiltered (diatomaceous earth) and concentrated to afford 2.9 g of a yellow solid. Recrystallization from ethyl acetate:ether afforded 2.21 g (80%) of the title compound as a light orange crystalline powder. $^1$H-NMR (300 MHz, CDCl$_3$) δ 7.68–7.71 (m, 2H), 7.56–7.62 (m, 1H), 7.46–7.51 (m, 2H), 7.18–7.2 (m, 5H), 6.97 (t, 1H, J=8.0 Hz), 6.58 (dd, 1H, J=8.0, 1.6 Hz), 6.47 (t, 1H, J=2.1 Hz), 6.32 (dd, 1H, J=8.0, 1.3 Hz), 4.70 (s, 1H). Mass spectrum (MALDI-TOF, gentisic acid matrix) calcd. for C$_{19}$H$_{18}$N$_2$O$_2$S: 339.1 (M+H), 361.1 (M+Na). Found: 339.5, 361.5.

d) N-benzyl-N-[[3-(1-tert-butoxycarbonylpiperidin-4-yl)carbonylamino]phenyl]benzenesulfonamide To 149 mg (0.650 mmol) of 1-tert-butoxycarbonylisonipecotic acid, as prepared in step e of Example 1, and 287 mg (0.650 mmol) of Castro's Reagent (benzotriazol-1-yloxytris-(dimethylaminophosphonium hexafluorophosphate, BOP) in 1.5 mL of anhydrous DMF was added 155 µL (0.887 mmol) of N,N-diisopropylethylamine and the mixture stirred under nitrogen for 5 min. A solution of 200 mg (0.591 mmol) of N-benzyl-N-(3-aminophenyl)benzenesulfonamide in 0.5 mL of DMF was added. After stirring for 16 h, 10 mL of saturated NaHCO$_3$ was added. The mixture was partitioned between 25 mL each of ethyl acetate and water. The organic layer was washed with 10% citric acid (2×20 mL), brine (20 mL) and dried (Na$_2$SO$_4$). Concentration afforded 360 mg of a yellow resin which was chromatographed on a Waters Associates 10 g silica Sep-Pak SPE column. Elution with a gradient of 5–10% ethyl acetate:dichloromethane afforded 268 mg (82%) of the title compound as a white foam. $^1$H-NMR (300 MHz, CDCl$_3$) δ 7.56–7.66 (m, 4H), 7.47 (m, 2H), 7.09–7.22 (m, 8H), 6.60 (br d, 1H, J=8.0 Hz), 4.70 (s, 2H), 4.14 (br s, 2H), 2.74 (br t, 2H, J=12 Hz), 2.24–2.34 (m, 1H), 1.84 (br s, 1H), 1.81 (br s, 1H), 1.69 (td, 2H, J=12.2, 4.1 Hz), 1.44 (s, 9H),.. Mass spectrum (MALDI-TOF, gentisic acid matrix) calcd. for C$_{30}$H$_{35}$N$_3$O$_5$S: 450.6 (M-BOC+2H). Found: 450.3.

e) N-benzyl-N-[[3-(1-tert-butoxycarbonyl)piperidin-4-ylmethylamino]phenyl]benzenesulfonamide To 293 µL (0.585 mmol) of 2M lithium borohydride in tetrahydrofuran was added 1.0 mL of tetrahydrofuran followed by 148 µL (1.17mmol) of chlorotrimethylsilane. After stirring for 4 min, 107 mg (0.195 mmol) of N-benzyl-N-[[3-(1-tert-butoxycarbonyl)piperidin-4-ylcarbonylamino]phenyl] benzenesulfonamide in 2.0 mL of DMF was added and the mixture heated at 50° C. under nitrogen for 20 h. After quenching the reaction with 0.16 mL of MeOH, 1.0 mL of 2N NaOH was added, the mixture stirred for 10 min and then extracted with ethyl acetate (2×10 mL). The combined extracts were washed with brine, dried (Na$_2$SO$_4$) and concentrated to 108 mg of a pale yellow resin. Chromatography on a Waters Associates 5 g silica Sep-Pak SPE column eluting with 5% ethyl acetate/dichloromethane afforded 93 mg (89%) of the title compound as a colorless resin. $^1$H-NMR (300 MHz, CDCl$_3$) δ 7.70–7.74 (m, 2H), 7.59 (m, 1H), 7.48 (m, 2H), 7.22 (m,5H), 6.95 (t, 1H, J=8.0 Hz), 6.40 (dd, 1H, J=8.1, 2.2 Hz), 6.25 (t, 1H, J=2.1 Hz), 6.17 (dd, 1H), J=7.2, 1.8 Hz), 4.70 (s, 2H), 4.11 (br s, 2H), 3.66 (br s, 1H), 2.85 (br s, 2H), 2.66 (t, 2H, J=13.3 Hz), 1.65 (d, 2H, J=13.3 Hz), 1.47 (s, 9H), 1.09(m, 2H). Mass spectrum (MALDI-TOF, gentisic acid matrix) calcd. for C$_{30}$H$_{37}$N$_3$O$_4$S: 435.6 (M-tert-butoxycarbonyl+H). Found: 435.6.

f) N-benzyl-N-[[3-(1-aminoiminomethyl)-piperidin-4-ylmethylamino]phenyl]benzenesulfonamide To 89.0 mg (0.166 mmol) of N-benzyl-N-[[3 -(1-tert-butoxycarbonyl)piperidin-4-ylmethylamino]phenyl] benzenesulfonamide in 3.0 mL of anhydrous dichloromethane was added 0.75 mL of trifluoroacetic acid. After stirring for 15 min, the solution was concentrated and placed under vacuum (0.1 torr/1 h) to afford 89 mg of a colorless resin. This residue in 1.5 mL of anhydrous DMF was treated with 48.7 mg (0.332 mmol) of 1H-pyrazole-1-carboxamide hydrochloride and 87 mL (0.498 mmol) of N,N-diisopropyl/ ethylamine and the mixture stirred for 21 h. An additional 24 mg (0.166 mmol) of 1H-pyrazole-1-carboxamide hydrochloride and 58 mL (0.332 mmol) of N,N-diisopropyl/ ethylamine and the mixture stirred for 6 h. Finally, an additional 37 mg (0.249 mmol) of 1H-pyrazole-1-carboxamide hydrochloride and 87 mL (0.498 mmol) of N,N-diisopropylethylamine and the mixture stirred for 48 h. After concentration to a syrup, 5 mL of 0.1N NaOH and 30 mL of ethyl acetate were added to the mixture. The solid formed was filtered off, washed with 5 mL of ethyl acetate and placed under vacuum (0.1 torr/1h) to afford 62.2 mg (78%) of the title compound as a white powder. $^1$H-NMR (300 MHz, CD$_3$OD) δ 7.66–7.72 (m, 3H), 7.53–7.65 (m, 2H), 7.16–7.24 (m, 5H), 6.90 (t, 1H, J=8.1 Hz), 6.46 (dd, 1H, J=8.1, 2.0 Hz), 6.22 (t, 1H, J=2.1 Hz), 6.13 (dd, 1H, J=7.6, 1.6 Hz), 4.73 (s, 2H), 3.02 (t, 2H, J=13.5 Hz), 2.85 (d, 2H, J=6.3 Hz), 1.77 (m, 3H), 1.23 (m, 2H). Mass spectrum (MALDI-TOF, gentisic acid matrix) calcd. for $C_{26}H_{31}N_5O_2S$: 478.2 (M+H). Found: 478.4.

EXAMPLE 12 a) 2-Chlorobenzenesulfonic acid 3-hydroxy-4-benzylphenyl ester

At 0° C. to a solution of 708 mg (3.54 mmol) of 4-benzylresorcinol in 20 mL of methylene chloride at 0° C. was added 410 µL (3.72 mmol) of N-methylmorpholine followed by 740 mg (3.51 mmol) of 2-chlorobenzenesulfonyl chloride. The reaction mixture was warmed to ambient temperature and stirred for 30 min. An additional 400 µL of N-methylmorpholine was added and the reaction mixture was stirred for another 60 min. The reaction mixture was quenched with 1N HCl, extracted into ether, washed with saturated $NaHCO_3$, dried ($MgSO_4$), and purified by flash chromatography (methylene chloride) to give 336.5 mg (25%) of the title compound as a colorless oil. $^1$H-NMR (300 MHz, $CDCl_3$) δ 7.95 (dd, 1H, J=1, 8 Hz), 7.55–7.63 (m, 2H), 7.34–7.40 (m, 1H), 7.1–7.3 (m, 5H), 6.98 (d, 1H), 6.61–6.65 (m, 2H), 4.95 (s, 1H), and 3.91 (s, 2H). Mass spectrum (MALDI-TOF; gentisic acid matrix) calcd. for $C_{19}H_{15}ClO_4S$: 375.0 (M+H), 397.0 (M+Na). Found: 373.6, 396.7.

b) 2-Chlorobenzenesulfonic acid 3-[[1-N-(tert-butoxycarbonyl)piperidin-4-yl]methoxy]-4-benzylphenyl ester To 294 mg (0.787 mmol) of 2-chlorobenzenesulfonic acid 3-hydroxy-4-benzylphenyl ester, as prepared in the preceding step, in tetrahydrofuran (5 mL) containing 236 µL (1.10 mmol) of N-tert-butoxycarbonyl-4-piperidinemethanol, as prepared in step f of Example 1, 300 µL (2.72 mmol) of N-methylmorpholine, and 309 mg (1.18 mmol) of triphenylphosphine was added 185 µL (1.18 mmol) of diethyl azodicarboxylate. The reaction mixture was stirred at ambient temperature for 1 h, quenched with saturated $NaHCO_3$, and extracted into ether. The organic phase was dried ($MgSO_4$) and concentrated in vacuo. Purification by flash chromatography (ethyl acetate/hexane (1:2)) gave 382 mg of the title compound as a colorless foam. $^1$H-NMR (300 MHz, $CDCl_3$) δ 7.95 (dd, 1H, J=1.5, 8 Hz), 7.55–7.64 (m, 2H), 7.35–7.40 (m, 1H), 7.08–7.26 (m, 5H), 6.93 (d, 2H, J=8 Hz), 6.65 (d, 2 Hz), 6.53 (dd, 1H, J=2, 8 Hz), 3.87 (s, 2H), 3.67 (d, 2H, 6 Hz), 2.69 (t, 2H, J=13 Hz), and 1.47 (s, 9H). Mass spectrum (MALDI-TOF; gentisic acid matrix) calcd. for $C_{30}H_{34}ClNO_6S$: 594.2 (M+Na). Found: 594.0, 472.0 (M - (tert-butoxycarbonyl)+H).

c) 2-Chlorobenzenesulfonic acid 3-[[piperidin-4-yl]methoxy]-4-benzylphenyl ester A solution of 380 mg (0.666 mmol) of 2-chlorobenzenesulfonic acid 3-[[1-N-(tert-butoxycarbonyl)piperidin-4-yl]methoxy]-4-benzylphenyl ester, as prepared in the preceding step, in 5 mL of methylene chloride was added 3 mL of 4N HCl in dioxane. The reaction mixture was stirred at ambient temperature for 1 h, carefully quenched with with saturated $NaHCO_3$, dried ($K_2CO_3$), and concentrated to give 381 mg of crude title compound as an oil which was used as is in the next step. $^1$H-NMR (300 MHz, $CDCl_3$) δ 7.96 (d, 1H), 7.54–7.63 (m, 2H), 7.34–7.40 (m, 1H), 7.08–7.24 (m, 4H), 6.91 (d, 1H, J=8 Hz), 6.66 (d, 1H, J=2 Hz), 6.54 (dd, 1H, J=2, 8 Hz), 3.88 (s, 2H), 3.66 (d, 2H, J=5 Hz), 3.10 (d, 2H, J=12 Hz), 2.62 (t, 2H, J=10 Hz), 1.1–1.2 (m, 4H). Mass spectrum (MALDI-TOF; gentisic acid matrix) calcd. for $C_{25}H_{26}ClNO_4S$: 472.1 (M+H). Found: 472.6.

d) 2-Chlorobenzenesulfonic acid 3-[[1-aminoiminomethyl)piperidin-4-yl]methoxy]-4-benzylphenyl ester acetic acid salt A mixture of 271 mg (0.576 mmol) of 2-chlorobenzenesulfonic acid 3-[[piperidin-4-yl]methoxy]-4-benzylphenyl ester as prepared in the preceding step, in 2 mL of DMF, 500 µL (4.54 mmol) of N,N-diisopropylethylamine, and 196 mg (1.34 mmol) of 1H-pyrazole-1-carboxamidine hydrochloride was stirred at ambient temperature for 2 days. The reaction mixture was quenched with 1N NaOH, extracted into methylene chloride, dried ($K_2CO_3$), and concentrated. The product was purified by flash chromatography (methylene chloride/methanol/acetic acid (93:6.5:0.5 to 78:19.6:3.4)) to give an oil. Crystallization from a mixture of methylene chloride, methanol and ether gave 146 mg of the title compound. $^1$H-NMR (300 MHz, $CD_3OD$) δ 7.92 (dd, 1H), 7.67–7.78 (m, 2H), 7.44–7.50 (m, 1H), 7.03–7.50 (m, 6H), 6.69 (d, 1H J=1 Hz), 6.57 (dd, 1H, J=3, 8Hz), 3.71 (d, 2H, J=4.5 Hz), 3.03 (t, 2H), 1.94–2.00 (m, 2H), 1.89 (s, 3 H), 1.70 (d, 2H), 2.12–1.34 (m, 2H). Mass spectrum (MALDI-TOF; gentisic acid matrix) calcd. for $C_{26}H_{28}ClN_3O_4S$: 514.2 (M+H), 536.1 (M+Na). Found: 514.4, 536.0.

EXAMPLE 13 a) 2-Chlorobenzenesulfonic acid 3-[[3-N-(tert-butoxycarbonyl)amino]propoxy]-5-methylphenyl ester A solution of 2-chlorobenzenesulfonic acid 3-hydroxy-5-methylphenyl ester (450 mg, 1.5 mmol), as prepared in step c of Example 3, N-(tert-butoxycarbonyl)-3-aminopropanol (263 mg, 1.5 mmol) and triphenylphosphine (400 mg, 1.5 mmol) in tetrahydrofuran (10 mL) at 0° C. was treated with diethyl azodicarboxylate (263 mg, 1.5 mmol). The reaction mixture was stirred at 0° C. for 2 h and at room temperature for 3 h. Water (50 mL) was added and the reaction mixture was extracted with ethyl acetate (3×50 mL). The organic extract was washed sequentially with saturated $NaHCO_3$ (2×50 mL) and brine (2×50 mL), dried over $Na_2SO_4$, and concentrated in vacuo. The residue was purified by flash column chromatography (1:2 ethyl acetate:hexane) to give the title compound as a colorless liquid (595 mg, 87%). 1H-NMR (300 MHz, $CDCl_3/CD_3OD$) δ 1.44 (s, 9H), 1.91 (t, 2H), 2.24 (s, 3H), 3.24 (q, 2H), 3.90 (t, 2H), 6.47 (d, 1H), 6.53 (s, 1H), 6.61 (d, 1H), 7.41 (m, 1H), 7.65 (m, 2H), 7.95 (dd, 1H).

b) 2-Chlorobenzenesulfonic acid 3-[[3-(aminoiminomethyl)amino]propoxy]-5-methylphenyl ester acetic acid salt:

2-Chlorobenzenesulfonic acid 3-[[3-(N-tert-butoxycarbonyl) amino]propoxy]-5-methylphenyl ester (456 mg, 1.0 mmol), as prepared in the preceding step, was treated with 10 mL of 4N HCl in 1,4-dioxane and stirred at room temperature for 2 h. The solvent was removed in vacuo and the residue was concentrated from methylene chloride several times to give the amine salt. This was dissolved in DMF (10 mL) and treated with N,N-diisopropylethylamine (1.0 mL) and aminoiminomethanesulfonic acid (248 mg, 2.0 mmol). The reaction mixture was stirred at room temperature overnight. The solvent was removed in vacuo. The residue was dissolved in methylene chloride (200 mL), washed with 10% $K_2CO_3$ (3×50 mL), dried over $K_2CO_3$, and concentrated in vacuo. The residue was purified by flash column chromatography (88:10:2 methylene chloride:methanol:acetic acid) to give the title compound as a colorless foam (370 mg, 80%). $^1$H-NMR (300 MHz, DMSO-$d_6$): δ 1.86 (t, 2H), 1.91 (s, 3H), 2.21 (s, 3H), 3.23 (q, 2H), 3.93 (t, 2H), 6.45 (d, 1H), 6.50 (s, 1H), 6.76 (s, 1H), 7.30 (bs, 4H), 7.59 (t, 1H), 7.87 (m, 2H), 7.95 (dd, 1H). Mass spectrum (MALDI-TOF, sinapinic acid matrix) calcd. for $C_{17}H_{20}N_3O_4SCl$: 398.1 (M+H), 420.1 (M+Na), 436.0 (M+K). Found: 397.9, 419.8, 435.8.

EXAMPLE 14 a) 2-Chlorobenzenesulfonic acid 3-[[4-(N-tert-butoxycarbonyl)amino]butoxy]-5-methylphenyl ester A solution of 2-chlorobenzenesulfonic acid 3-hydroxy-5-methylphenyl ester (450 mg, 1.5 mmol), as prepared in step c of Example 3, N-(tert-butoxycarbonyl)-4-aminobutanol (284 mg, 1.5 mmol), and triphenylphosphine (400 mg, 1.5 mmol) in tetrahydrofuran (10 mL) at 0° C. was treated with diethyl azodicarboxylate (263 mg, 1.5 mmol). The reaction was stirred at 0° C. for 2 h and at room temperature for 3 h. Water (50 mL) was added and the reaction mixture was extracted with ethyl acetate (3×50 mL). The organic phase was washed sequentially with saturated $NaHCO_3$ (2×50 mL) and brine (2×50 mL), dried over $Na_2SO_4$, and concentrated in vacuo. The residue was purified by flash column chromatography (1:2 ethyl acetate:hexane) to give the title compound as a colorless liquid (615 mg, 87%). $^1$H-NMR (300 MHz, $CDCl_3$): δ 1.45 (s, 9H), 1.62 (m, 2H), 1.73 (m, 2H), 2.24 (s, 3H), 3.13 (t, 2H), 3.86 (t, 2H), 6.45 (s, 1H), 6.51 (d, 1H), 6.60 (s, 1H), 7.41 (t, 1H), 7.65 (m, 2H), 7.95 (dd, 1H).

b) 2-Chlorobenzenesulfonic acid 3-[[4-(aminoiminomethyl)amino]butoxy]-5-methylphenyl ester acetic acid salt 2-Chlorobenzenesulfonic acid 3-[[4-(N-tert-butoxycarbonyl)amino]butoxy]-5-methylphenyl ester (470 mg, 1.0 mmol), as prepared in the preceding step, was treated with 10 mL of 4N HCl in 1,4-dioxane and stirred at room temperature for 2 h. The solvent was concentrated in vacuo and concentrated from methylene chloride several times to give the amine salt. This was dissolved in DMF (10 mL) and treated with N,N-diisopropylethylamine (1.0 mL) and aminoiminomethanesulfonic acid (248 mg, 2.0 mmol). The reaction mixture was stirred at room temperature overnight. The DMF was evaporated in vacuo. The residue was dissolved in methylene chloride (200 mL), washed with 10% $K_2CO_3$ (2×50 mL), dried over $K_2CO_3$, and concentrated in vacuo. The residue was purified by flash column chromatography (88:10:2 methylene chloride:methanol:acetic acid) to give the title compound as a colorless foam (368 mg, 78%). $^1$H-NMR (300 MHz, $CDCl_3/CD_3OD$) δ 1.78 (m, 4H), 1.99 (bs, 3H), 2.24 (s, 3H), 3.18 (t, 2H), 3.90 (t, 2H), 6.49 (d, 2H), 6.61 (s, 1H), 7.44 (t, 1H), 7.67 (m, 2H), 7.95 (dd, 1H). spectrum (MALDI-TOF, sinapinic acid matrix) calcd. for $C_{18}H_{22}N_3O_4SCl$: 412.1 (M+H), 434.1 (M+Na). Found: 412.4, 434.4.

EXAMPLE 15 a) 1-Naphthalenesulfonic acid 3-benzyloxy-5-methylphenyl ester

A solution of 3-benzyloxy-5-methylphenol (600 mg, 3.0 mmol), as prepared in step a of Example 3, in methylene chloride (15 mL) at 0° C. was treated with N,N-diisopropylethylamine (0.5 mL) and 1-naphthalenesulfonyl chloride (670 mg, 3.0 mmol). The reaction mixture was stirred at 0° C. for 2 h and at room temperature for 2 h. The reaction mixture was diluted with methylene chloride (200 mL) and water (50 mL). The organic extract was washed sequentially with saturated $NaHCO_3$ (2×50 mL) and brine (2×50 mL), dried over $Na_2SO_4$, and concentrated in vacuo. The residue was purified by flash column chromatography (1:1 hexane:methylene chloride) to give the title compound as a colorless liquid (1.05 g, 87%). $^1$H-NMR (300 MHz, $CDCl_3$) δ 2.16 (s, 3H), 4.73 (s, 2H), 6.23 (t, 1H), 6.37 (dd, 1H), 6.61 (dd, 1H), 7.28 (m, 5H), 7.48 (t, 1H), 7.67 (t, 1H), 7.77 (t, 1H), 7.97 (t, 1H), 8.12 (dt, 2H), 8.19 (dd, 1H).

b) 1-Naphthalenesulfonic acid 3-hydroxy-5-methylphenyl ester

A mixture of 1-naphthalenesulfonic acid 3-benzyloxy-5-methylphenyl ester (1.0 g, 2.47 mmol), as prepared in the preceding step, and 10% palladium on carbon (200 mg) in ethanol (20 mL) was hydrogenated (balloon) overnight. The catalyst was removed by filtration through diatomaceous earth (methanol washes) and the filtrate was evaporated in vacuo to give the title compound as a colorless syrup (705 mg, 91%). $^1$H-NMR (300 MHz, $CDCl_3$) δ 2.11 (s, 3H), 4.20 (bs, 1H), 6.16 (t, 1H), 6.47 (t, 1H), 7.51 (t, 1H), 7.69 (t, 1H), 7.79 (t, 1H), 7.81 (d, 1H), 8.11 (dt, 2H), 8.77 (dd, 1H).

c) 1-Naphthalenesulfonic acid 3-hydroxy-5-methylphenyl ester

A solution of 1-naphthalenesulfonic acid 3-hydroxy-5-methylphenyl ester (315 mg, 1.0 mmol), as prepared in the preceding step, N-(tert-butoxycarbonyl)-4-piperidinemethanol (215 mg, 1.0 mmol), as prepared in step f of Example 1, and triphenylphosphine (263 mg, 1.0 mmol) in tetrahydrofuran (10 mL) at 0° C. was treated with diethyl azodicarboxylate (175 mg, 1.0 mmol). The reaction mixture was stirred at 0° C. for 2 h and at room temperature for 3 h. Water (50 mL) was added. The reaction mixture was extracted into ethyl acetate (3×50 mL), washed sequentially with saturated $NaHCO_3$ (2×50 mL) and brine (2×50 mL), dried over $Na_2SO_4$, and concentrated in vacuo. The residue was purified by flash column chromatography (1:3 ethyl acetate:hexane) to give the title compound as a colorless liquid (285 mg, 56%). $^1$H-NMR (300 MHz,$CDCl_3$) δ 1.16 (m, 2H), 1.47 (s, 9H), 1.70 (m, 2H), 1.78 (m, 1H), 2.15 (s, 3H), 2.70 (t, 2H), 3.48 (d, 2H), 4.11 (m, 2H), 6.16 (d, 1H), 6.32 (s, 1H), 6.51 (s, 1H), 7.49 (t, 1H), 7.68 (t, 1H), 7.79 (t, 1H), 7.80 (d, 1H), 8.14 (d, 2H), 8.81 (d, 1H).

d) 1-Naphthalenesulfonic acid 3-[[1-(aminoiminomethyl)piperidin-4-yl]methoxy]-5-methylphenyl ester acetic acid salt 1-Naphthalenesulfonic acid 3-[[N-(tert-butoxycarbonyl)piperidin-4-yl]methoxy]-5-methylphenyl ester (256 mg, 0.5 mmol), as prepared in the preceding step, was treated with 10 mL of 4N HCl in 1,4-dioxaneat room temperature for 2 h. The solvent was removed in vacuo and the residue concentrated from methylene chloride several times to give the amine salt. This was then dissolved in DMF (10 mL) and treated with N,N-diisopropylethylamine (0.5 mL) and aminoiminomethanesulfonic acid (124 mg, 1.0 mmol). The reaction mixture was stirred at room temperature overnight. The DMF was removed in vacuo. The residue was partitioned between methylene chloride (200 mL) and 10% $K_2CO_3$ (50 mL). The organic phase was washed with 10% $K_2CO_3$ (2×50 mL), dried over $K_2CO_3$, and concentrated in vacuo. The residue was purified by flash column chromatography (88:10:2 methylene chloride:methanol:acetic acid) to give the title compound as a colorless foam (142 mg, 58%). $^1$H-NMR (300 MHz, $CDCl_3$) δ 1.25 (m, 2H), 1.84 (m, 3H), 2.05 (bs, 3H), 2.12 (s, 3H), 3.03 (t, 2H), 3.52 (d, 2H), 4.03 (d, 2H), 6.19 (s, 1H), 6.27 (s, 1H), 6.49 (s, 1H), 7.43 (bs, 4H), 7.49 (t, 1H), 7.67 (t, 1H), 7.78 (1H), 7.80 (d, 1H), 8.14 (t, 2H), 8.78 (d, 1H). Mass spectrum (MALDI-TOF, sinapinic acid matrix) calcd. for $C_{24}H_{27}N_3O_4S$: 454.2 (M+H), 476.2 (M+Na). Found: 454.9, 476.9.

EXAMPLE 16 a) 3-Trifluoromethylbenzenesulfonic acid 3-benzyloxy-5-methylphenyl ester

A solution of 3-benzyloxy-5-methylphenol (400 mg, 2.0 mmol), as prepared in step a of Example 3, in methylene chloride (10 mL) at 0° C. was treated with N,N-diisopropylethylamine (0.4 mL) and 3-trifluoromethylbenzenesulfonyl chloride (489 mg, 2.0 mmol). The reaction mixture was stirred at 0° C. for 2 h and at room temperature for 2 h. The reaction mixture was diluted with methylene chloride (200 ml,) and water (50 mL). The organic extract was washed sequentially with saturated $NaHCO_3$ (2×50 mL) and brine (2×50 mL), dried over $Na_2SO_4$, and concentrated in vacuo. The residue was purified by flash column chromatography (1:1 hexane:methylene chloride) to give the title compound as a colorless liquid (710 mg, 85%). $^1$H-NMR (300 MHz, $CDCl_3$) δ 2.25 (s, 3H), 4.94 (s, 2H), 6.41 (s, 2H), 6.72 (s, 1H), 7.37 (m, 5H), 7.68 (t, 1H), 7.91 (d, 1H), 8.03 (d, 1H), 8.09 (s, 1H).

b) 3-Trifluoromethylbenzenesulfonic acid 3-hydroxy-5-methylphenyl ester

A mixture of 3-trifluoromethylbenzenesulfonic acid 3-benzyloxy-5-methylphenyl ester (633 mg, 1.5 mmol), as prepared in the preceding step, and 10% palladium on carbon (100 mg) in ethanol (20 mL) was hydrogenated (balloon) for 3 h. The catalyst was removed by filtration through diatomaceous earth (methanol washes) and the filtrate was evaporated in vacuo to give the title compound as a colorless syrup (485 mg, 97%). $^1$H-NMR (300 MHz, $CDCl_3$/$CD_3OD$) δ 2.20 (s, 3H), 6.26 (s, 1H), 6.30 (t, 1H), 6.57 (s, 1H), 7.74 (t, 1H), 7.96 (d, 1H), 8.05 (d, 1H), 8.09 (s, 1H).

c) 3-Trifluoromethylbenzenesulfonic acid 3-[[N-(tert-butoxycarbony)piperidin-4-yl]methoxy]-5-methylphenyl ester

A solution of 3-trifluoromethylbenzenesulfonic acid 3-hydroxy-5-methylphenyl ester (332 mg, 1.0 mmol), as prepared in the preceding step, N-(tert-butoxycarbonyl)-4-piperidinemethanol (215 mg, 1.0 mmol), as prepared in step f of Example 1, and triphenylphosphine (263 mg, 1.0 mmol) in tetrahydrofuran (10 mL at 0° C. was treated with diethyl azodicarboxylate (175 mg, 1.0 mmol). The reaction mixture was stirred at 0° C. for 2 h and at room temperature for 3 h. Water (50 mL) was added. The reaction mixture was extracted into ethyl acetate (3×50 mL), washed sequentially with saturated $NaHCO_3$ (2×50 mL), dried over $Na_2SO_4$, and concentrated in vacuo. The residue was purified by flash column chromatography (1:2 ethyl acetate:hexane) to give the title compound as a colorless liquid (375 mg, 70%). $^1$H-NMR (300 MHz, $CDCl_3$) δ 1.26 (m, 2H), 1.47 (s, 9H), 1.77 (m, 2H), 1.89 (m, 1H), 2.24 (s, 3H), 2.73 (t, 2H), 3.67 (d, 2H), 4.13 (m, 2H), 6.34 (d, 1H), 6.36 (s, 1H), 6.62 (s, 1H), 7.72 (t, 1H), 7.94 (d, 1H), 8.09 (d, 2H).

d) 3-Trifluoromethylbenzenesulfonic acid 3-[[1-(aminoiminomethyl)piperidin-4-yl]-methoxy]-5-methylphenyl ester acetic acid salt

3-Trifluoromethylbenzenesulfonic acid 3-[[N-(tert-butoxycarbonyl) piperidin-4-yl]methoxy]-5-methylphenyl ester (265 mg, 0.5 mmol), as prepared in the preceding step, was treated with 10 mL of 4N HCl in 1,4-dioxane at room temperature for 2 h. The solvent was removed in vacuo and the residue was concentrated from methylene chloride several times to give the amine salt. The amine salt was dissolved in DMF (10 mL) and treated with triethylamine (0.5 mL) and aminoiminomethanesulfonic acid (124 mg, 1.0 mmol). The reaction mixture was stirred at room temperature overnight. The DMF was removed in vacuo. The residue was dissolved in methylene chloride (200 mL). The organic phase was washed with 10% $K_2CO_3$ (2×50 mL), dried over $K_2CO_3$, and concentrated in vacuo. The residue was purified by flash column chromatography (88:10:2 methylene chloride:methanol:acetic acid) to give the title compound as a colorless foam (123 mg,47%). 1H-HMR (300 MHz, $CDCl_3$) δ 1.44 (m, 2H), 1.79 (s, 3H), 1.94 (m, 2H), 2.09 (m, 1H), 2.22 (s, 3H), 3.10 (t, 2H), 3.71 (d, 2H), 4.08 (d, 2H), 6.33 (s, 1H), 6.37 (s, 1H), 6.60 (s, 1H), 7.28 (bs, 4H), 7.35 (t, 1H), 7.95 (d, 1H), 8.07 (d, 1H). Mass spectrum (MALDI-TOF, sinapinic acid matrix) calcd. for $C_{21}H_{24}N_3O_4SF_3$: 472.2 (M+H), 494.1 (M+Na). Found: 472.6, 494.7.

EXAMPLE 17 a) Benzenesulfonic acid 3-benzyloxy-5-methylphenyl ester

A solution of 3-benzyloxy-5-methylphenol (400 mg, 2.0 mmol), as prepared in step a of Example 3, in methylene chloride (10 mL) at 0° C. was treated with N,N-diisopropylethylamine (0.4 mL) and benzenesulfonyl chloride (354 mg, 2.0 mmol). The reaction mixture was stirred at 0° C. for 2 h and at room temperature for 2 h. The reaction mixture was diluted with methylene chloride (200 mL) and water (50 mL). The organic extract was washed sequentially with saturated $NaHCO_3$ (2×50 mL) and brine (2×50 mL), dried over $Na_2SO_4$, and concentrated in vacuo. The residue was purified by flash column chromatography (1:1 hexane:methylene chloride) to give the title compound as a colorless liquid (675 mg, 95%). $^1$H-NMR(300 MHz, $CDCl_3$) δ 2.24 (s, 3H), 4.91 (s, 2H), 6.40 (t, 1H), 6.43 (s, 1H), 6.68 (s, 1H), 7.36 (m, 5H), 7.52 (t, 2H), 7.64 (d, 1H), 7.83 (t, 2H).

b) Benzenesulfonic acid 3-hydroxy-5-methylphenyl ester

A mixture of benzenesulfonic acid 3-benzyloxy-5-methylphenyl ester (532 mg, 1.5 mmol), as prepared in the preceding step, and 10% palladium on carbon (200 mg) in ethanol (20 mL) was hydrogenated (balloon) overnight. The catalyst was removed by filtering over diatomaceous earth and the filtrate was evaporated in vacuo to give the title compound as a colorless syrup (390 mg, 98%). $^1$H-NMR (300 MHz, $CDCl_3$/$CD_3OD$) δ 2.19 (s, 3H), 6.27 (s, 1H), 6.54 (s, 1H), 6.66 (s 1H), 7.43 (m, 1H), 7.55 (t, 1H), 7.70 (t, 1H), 7.85 (m, 2H).

c) Benzenesulfonic acid 3-[[N-(tert-butoxycarbonyl) piperidin-4-yl]methoxy]-5-methylphenyl ester

To a solution of benzenesulfonic acid 3-hydroxy-5-methylphenyl ester (528 mg, 2.0 mmol), as prepared in the preceding step, N-(tert-butoxycarbonyl)-4-piperidinemethanol (430 mg, 2.0 mmol), as prepared in step f of Example 1, and triphenylphosphine (525 mg, 2.0 mmol) in tetrahydrofuran (20 mL) at 0° C. was added diethyl azodicarboxylate (349 mg, 2.0 mmol). The reaction mixture was stirred at 0° C. for 2 h and at room temperature for 3 h. The reaction mixture was diluted with methylene chloride (200 mL) and water (50 mL). The organic extract was washed sequentially with saturated $NaHCO_3$ (2×50 mL) and brine (2×50 mL), dried over $Na_2SO_4$, and concentrated in vacuo. The residue was purified by flash column chromatography (1:2 ethyl acetate:hexane) to give the title compound as a colorless liquid (781 mg, 84%). $^1$H-NMR (300 MHz, $CDCl_3$) δ 1.24 (m, 2H), 1.47 (s, 9H), 1.76 (m, 2H), 1.88 (m, 1H), 2.24 (s, 3H), 2.73 (t, 2H), 3.66 (d, 2H), 4.12 (m, 2H), 6.32 (s, 1H), 6.58 (s, 1H), 7.54 (t, 2H), 7.67 (t, 1H), 7.86 (d, 2H).

d) Benzenesulfonic acid 3-[[1-(aminoiminomethyl) piperidin-4-yl]methoxy]-5-methylphenyl ester acetic acid salt

Benzenesulfonic acid 3-[[N-(tert-butoxycarbonyl) piperidin-4-yl]methoxy]-5-methylphenyl ester (462 mg, 1.0 mmol), as prepared in the preceding step, was treated with 15 mL of 4N HCl in 1,4-dioxane and stirred at room temperature for 2 h. The solvent was evaporated in vacuo and concentrated from methylene chloride several times to give the amine salt. This was dissolved in DMF (10 mL) and then treated with triethylamine (1.0 mL) and aminoiminomethanesulfonic acid (248 mg, 2.0 mmol). The reaction mixture was stirred at room temperature overnight. The DMF was evaporated in vacuo. The residue was dissolved in methylene chloride (200 mL), washed with 10% $K_2CO_3$ (3×50 mL), dried over $K_2CO_3$ and concentrated in vacuo. The residue was purified by flash column chromatography (88:10:2 methylene chloride:methanol:acetic acid) and crystallized from acetonitrile-ethyl ether to give the title compound as white crystals (185 mg, 40%). $^1$H-NMR (300 MHz, $CD_3OD$) δ 1.41 (m, 2H), 1.89 (s, 3H), 1.92 (m, 2H), 2.08 (m, 1H), 2.20 (s, 3H), 3.12 (dt, 2H), 3.75 (d, 2H), 3.91 (d, 2H), 6.35 (d, 2H), 6.67 (s, 1H), 7.61 (t, 2H), 7.75 (t, 1H), 7.83 (d, 2H). Mass spectrum (MALDI-TOF, sinapinic acid matrix) calcd. for $C_{20}H_{25}N_3O_4S$: 404.2 (M+H). Found: 404.5.

EXAMPLE 18 a) 3-Chlorobenzenesulfonic acid 3-hydroxy-5-methylphenyl ester:

Orcinol monohydrate (1.42 g, 10 mmol) and 3-chlorobenzenesulfonyl chloride (2.43 g, 11 mmol) were vigorously stirred in a mixture of saturated $NaHCO_3$ (30 mL) and ethyl ether (30 mL) at room temperature for 2 days. The reaction mixture was partitioned between ethyl acetate (200 mL) and water (50 mL). The organic extract was washed sequentially with brine (2×50 mL), dried over $Na_2SO_4$, and concentrated in vacuo. The residue was purified by flash column chromatography (2% ethyl acetate in methylene chloride) to give the title compound as a pale-yellow liquid (2.08 g, 69%). $^1$H-NMR (300 MHz, $CDCl_3$) δ 2.24 (s, 3H), 5.32 (s, 1H), 6.33 (t, 1H ), 6.140 (s, 1H), 6.57 (s, 1H), 7.48 (t, 1H), 7.65 (dt, 1H), 7.72 (dt, 1H), 7.86 (t, 1H).

b) 3-Chlorobenzenesulfonic acid 3-[[N-(tert-butoxycarbonyl)piperidin-4-yl]methoxy]-5-methylphenyl ester:

A solution of 3-chlorobenzenesulfonic acid 3-hydroxy-5-methylphenol (600 mg, 2.0 mmol), as prepared in the preceding step, N-(tert-butoxycarbonyl)-4-piperidinemethanol (430 mg, 2.0 mmol), as prepared in step f of Example 1, and triphenylphosphine (525 mg, 2.0 mmol) in tetrahydrofuran (20 mL) at 0° C. was treated with diethyl azodicarboxylate (349 mg, 2.0 mmol). The reaction mixture was stirred at 0° C. for 2 h and at room temperature for 3 h. The reaction mixture was partitioned between ethyl acetate (200 mL) and water (50 mL). The organic extract was washed sequentially with saturated $NaHCO_3$ (2×50 mL,) and brine (2×50 mL), dried over $Na_2SO_4$, and concentrated in vacuo. The residue was purified by flash column chromatography (1:3 ethyl acetate:hexane) to give the title compound as a colorless liquid (800 mg, 8 1%). $^1$H-NMR (300 MHz, $CDCl_3$) δ 1.24 (m, 2H), 1.47 (s, 9H), 1.75 (m, 2H), 1.90 (m, 1H), 2.25 (s, 3H), 2.73 (t, 2H), 3.68 (d, 2H), 4.13 (m, 2H), 6.34 (t, 1H), 6.39 (s, 1H), 6.61 (s, 1H), 7.49 (t, 1H), 7.63 (d, 1H), 7.75 (d, 1H), 7.86 (t, 1H).

c) 3-Chlorobenzenesulfonic acid 3-[[1-(aminoiminomethyl)-piperidin-4-yl]methoxy]-5-methylphenyl ester acetic acid salt:

3-Chlorobenzenesulfonic acid 3 -[[N-(tert-butoxycarbony)piperidin-4-yl]methoxy]-5-methylphenyl ester (496 mg, 1.0 mmol), as prepared in the preceding step, was treated with 15 mL of 4 N HCl in 1,4-dioxane and stirred at room temperature for 2 h. The solvent was evaporated in vacuo and concentrated from methylene chloride several times to give the amine salt. This was dissolved in DMF (10 mL) and treated with triethylamine (1.0 mL) and aminoiminomethanesulfonic acid (248 mg, 2.0 mmol). The reaction mixture was stirred at room temperature overnight. The DMF was removed in vacuo. The residue was dissolved in methylene chloride (200 mL), washed with 10% $K_2CO_3$ (3×50 mL), dried over $K_2CO_3$, and concentrated in vacuo. The residue was purified by flash column chromatography (88:10:2 methylene chloride:methanol:acetic acid) and crystallized from acetonitrile/ethyl ether to give product the title compound as white crystals (305 mg, 61%). $^1$H-NMR (300 MHz, $CD_3OD$) δ 8 1.41 (m, 2H), 1.89 (s, 3H), 1.93 (m, 2H), 2.09 (m, 1H), 2.23 (s, 3H), 3.12 (dt, 2H), 3.77 (d, 2H), 3.92 (d, 2H), 6.38 (d, 2H), 6.70 (s, 1H), 7.61 (t, 1H), 7.77 (t, 1H), 7.80 (s, 1H). Mass spectrum (MALDI-TOF, sinapinic acid matrix) calcd. for $C_2H_{24}N_3O_4SCl$:438.1 (M+H). Found: 438.9.

The following additional compounds (Examples 19–35) were synthesized by a process analogous to that employed in Example 18:

EXAMPLE 19

3-Methoxybenzenesulfonic acid 3-[[1-(aminoiminomethyl)piperidin-4-yl]methoxy]-5- methylphenyl ester hydrochloride:

1H-NMR (300 MHz, DMSO-$d_6$) δ 1.17–1.28 (m.2H), 1.74–1.79 (m, 2H), 1.98 (m, 1H), 2.21 (s, 3H), 302 (br t, 2H), 3.75 (d, 2H), 3.84–3.88 (m, 5H), 6.39 (br s, 1H), 6.47 (br s, 1H), 6.74 (br s, 1H), and 7.37–7.62 (m, 4H). Mass spectrum (MALDI-TOF, α-cyano-4-hydroxycinnamic acid matrix) calcd. for $C_{21}H_{27}N_3O_5S$: 434.2 (M+H). Found: 434.7.

EXAMPLE 20

3-[(Carboxy)methoxy]benzenesulfonic acid 3-[[1-(aminoiminomethyl)piperidin-4- yl]methoxy]-5-methylphenyl ester:

$^1$H-NMR (300 MHz, $CDCl_3$/TFA) δ 1.37–1.52 (m, 2H), 1.96–2.10 (m, 3H), 2.25 (s, 3H), 3.14 (br t, 2H), 3.75–3.86 (m, 4H), 4.79 (s, 2H), 6.36 (br s, 1H), 6.40 (br s, 1 H), 6.62 (br s, 1H), and 7.28–7.56 (m, 4H). Mass spectrum (MALDI-TOF, α-cyano-4-hydroxycinnamic acid matrix) calcd. for $C_{22}H_{27}N_3O_7S$: 478.2 (M+H), 500.1 (M +Na). Found: 478.1, 500. 1.

Example 21

3-Hydroxybenzenesulfonic acid 3-[[1-(aminoiminomethyl)piperidin-4-yl]methoxy]-5-methylphenyl ester hydrochloride:

1H-NMR (300 MHz, DMSO-$d_6$) δ 1.20–1.29 (m, 2H), 1.77 (br d, 2H), 1.99 (s, 1H), 2.22 (s, 3H), 3.02 (t,2H), 3.76 (d, 2H), 3.87 (m, 2H), 6.35 (br s, 1H), 6.44 (br s, 1H), 6.74 (br s, 1H), and 7.17–7.51 (m, 4H). Mass spectrum (MALDI-TOF, α-cyano-4-hydroxycinnamic acid matrix) calcd. for $C_{20}H_{25}N_3O_5S$: 420.2 (M+H), 442.1 (M+Na). Found: 420.2, 442.1.

EXAMPLE 22

3-(2 '-Hydroxyethoxy) benzenesulfonic acid 3-[[1-(aminoiminomethyl)piperidin-4-yl]methoxyl]-5-methylphenyl ester hydrochloride:

$^1$H-NMR (300 MHz, DMSO-$d_6$) δ 1.20–1.28 (m, 2H), 1.77 (br d, 2H), 1.98 (m, 1H), 2.21 (s,3H), 3.02 (t, 2H), 3.69–3.88 (m, 6H), 4.07 (t, 2H), 4.94 (t, 1H), 6.40 (br s, 1H), 6.47 (br s, 1H), 6.74 (br s, 1H), and 7.30–7.61 (m, 4H). Mass spectrum (MALDI-TOF, gentisic acid matrix) calcd. for $C_{22}H_{29}N_3O_6S$: 464.2 (M+H). Found: 464.4.

EXAMPLE 23

3-(2',3'-Dihydroxypropoxy)benzenesulfonic acid 3-[[1 (aminoiminomethyl)piperidin-4-yl]methoxy]-5-methylphenyl ester hydrochloride:

¹H-NMR (300 MHz, DMSO-d₆) δ 1.25–1.42 (m, 2H), 1.83–2.07 (m, 3H), 2.23 (s, 3H), 2.8–3.1 (m, 2H), 3.26 (br d, 1H), 3.47 (d, 2H), 3.74–3.98 (m, 5–6H), 6.38 (br t, 1H), 6.47 (br s, 1H), 6.73 (br s, 1H), and 7.33–7.60 (m, 4H). Mass spectrum (MALDI-TOF, α-cyano-4-hydroxycinnamic acid matrix) calcd. for $C_{23}H_{31}N_3O_7S$: 494.2 (M+H). Found: 494.1.

EXAMPLE 24

2-Chlorobenzenesulfonic acid 3-[[1-(aminoiminomethyl)piperidin-4-yl]methoxy]-5-chlorophenyl ester hydrochloride:

¹H-NMR (300 MHz, DMSO-d₆) δ 1.24 (m, 2H), 1.75 (d, J=11.3 Hz, 2H), 1.99 (m, 1H), 3.01 (t, J=12 Hz, 2H), 3.86 (m, 4H), 6.65 (t, J=2.2 Hz, 1H), 6.74 (t, J=2.1 Hz, 1H), 7.07 (t, J=2.1 Hz, 1H), 7.47 (br s, 3H), 7.61 (t, J=7.4 Hz, 1H), 7.89 (m, 2H), 7.99 (d, J=15.6 Hz, 1H). Mass spectrum (MALDI-TOF, sinapinic acid matrix) calcd. for $C_{19}H_{21}Cl_2N_3O_4S$: 458.1 (M+H); Found: 457.9.

EXAMPLE 25

3-Nitrobenzenesulfonic acid 3-[[1-(aminoiminomethyl)piperidin-4-yl]methoxy]-5-methylphenyl ester hydrochloride:

¹H-NMR (300 MHz, DMSO-d₆) δ 1.24 (m, 2H), 1.76 (d, J=12.5 Hz, 2H), 1.99 (m, 1H), 2.22 (s, 3H), 3.01 (t, J=12.1 Hz,2H),3.76(d, J=7.0 Hz,2H),3.88(d, J=13.2 Hz,2H),6.49(s, 1H), 6.52 (s, 1H), 6.77 (s, 1H), 7.45 (br s, 3H), 7.98 (t, J=8.0 Hz, 1H), 8.30 (d, J=8.0 Hz, 1H), 8.50 (s, 1H), 8.65 (d, J=8.1 Hz, 1H). Mass spectrum (MALDI-TOF, sinapinic acid matrix) calcd. for $C_{20}H_{24}N_4O_6S$: 449.1 (M+H), 471.1 (M+Na); Found: 449.2, 471.3.

EXAMPLE 26

3-Aminobenzenesulfonic acid 3-[[1-(aminoiminomethyl)piperidin-4-yl]methoxy]-5-methylphenyl ester hydrochloride:

¹H-NMR (300 MHz, DMSO-d₆) δ 1.25 (m, 2H), 1.76 (d, J=13.0 Hz, 2H), 1.98 (m, 1H), 2.22 (s, 3H), 3.01 (t, J=12.1 Hz, 2H), 3.75 (d, J=6.2 Hz, 2H), 3.88 (d, J=13.2 Hz, 2H), 5.79 s, 2H), 6.31 (s, 1H), 6.45 (s, 1H), 6.72 (s, 1H), 6.89 (s, 1H), 6.91 (s, 1H), (s, 1H), 7.27 (t, J=7.9 Hz, 1H), 7.45 (br s, 3). Mass spectrum (MALDI-TOF, sinapinic acid matrix) calcd. for $C_{20}H_{26}N_4O_4S$: 419.2 (M+H); Found: 419.6.

EXAMPLE 27

2-(Methoxycarbonyl)benzenesulfonic acid 3-[[1-(aminoiminomethyl)piperidin-4-yl]methoxy]-5-methylphenyl ester hydrochloride:

¹H-NMR (300 MHz, DMSO-d₆) δ 1.25 (m, 2H), 1.90 (d, J=12.5 Hz, 2H), 2.01 (m, 1H), 2.23 (s, 3H), 3.06 (t, J=12.5 Hz, 2H), 3.69 (d, J=7.6 Hz, 2H), 3.97 (s, 1H), 4.08 (d, J=12.0 Hz, 2H), 6.46 (s, 1H), 6.51 (s,1H), 6.58 (s, 1H), 7.30 (br s, 3H), 7.58 (m, 1H), 8.71 (d, J=7.4 Hz, 2H), 7.86 (d, J=7.7 Hz, 1H). Mass spectrum (MALDI-TOF, sinapinic acid matrix) calcd. for $C_{22}H_{27}N_3O_6S$: 462.2 (M+H), 484.2 (M+Na); Found: 462.2, 484.5.

EXAMPLE 28

4-Nitrobenzenesulfonic acid 3-[[1-(aminoiminomethyl)piperidin-4-yl]methoxy]-5-methylphenyl ester hydrochloride:

¹H-NMR (300 MHz, DMSO-d₆) δ 1.25 (m, 2H), 1.76 (d, J=13.0 Hz, 2H), 1.99 (m, 1H), 2.22 (s, 3H), 3.01 (t, J=12.2 Hz,2H),3.76(d, J=6.0 Hz,2H), 3.88 (d, J=13.0 Hz,2H),6.46 (s, 1H), 6.49 (s, 1H), 6.77 (s, 1H), 7.42 (br s, 3H), 8.18 (d, J=8.1 Hz, 2H), 8.46 (d, J=8.1 Hz, 2H). Mass spectrum (MALDI-TOF, sinapinic acid matrix) calcd. for $C_{20}H_{24}N_4O_6S$: 449.1 (M+H); Found: 448.9.

EXAMPLE 29

4-Aminobenzenesulfonic acid 3-[[-(aminoiminomethyl)piperidin-4-yl]methoxy]-5-methylphenyl ester hydrochloride:

¹H-NMR (300 MHz, DMSO-d₆) δ 1.25 (m, 2H), 1.77 (d, J=12.7 Hz, 2H), 1.98 (m, 1H), 2.21 (s, 3H), 3.01 (t, J=12.3 Hz, 2H), 3.74 (d, J=6.2 Hz, 2H), 3.88 (d, J=13.8 Hz, 2H), 6.28 (s, 1H), 6.41 (s, 3H), 6.61 (s, 1H), 6.64 (s, 1H), 6.69 (s, 1H), 7.41 (bs, 6 H). Mass spectrum (MALDI-TOF, sinapinic acid matrix) calcd. for $C_{20}H_{26}N_4O_4S$: 419.1 (M=H); Found: 419.1.

EXAMPLE 30

2-Nitrobenzenesulfonic acid 3-[[1-(aminoiminomethyl)piperidin-4-yl]methoxy]-5-methylphenyl ester hydrochloride:

¹H-NMR (300 MHz, DMSO-d₆) δ 1.25 (m, 2H), 1.77 (d, J=12.7 Hz, 2H), 2.00 (m, 1H), 2.23 (s, 3H), 3.01 (t, J=12.4 Hz, 2H), 3.79 (d, J=6.1 Hz, 2H), 3.89 (d, J=13.2 Hz, 2H), 6.51 (s, 1H), 6.55 (s, 1H), 6.80 (s, 1H), 7.48 (br s, 3H), 7.91 (t, J=7.6 Hz, 1H), 8.06 (m, 2H), 8.21 (d, J=7.4 Hz, 1H). Mass spectrum (MALDI-TOF, sinapinic acid matrix) calcd. for $C_{20}H_{24}N_4O_6S$: 449.1 (M+H); Found: 449.0.

EXAMPLE 31

2-Aminobenzenesulfonic acid 3-[[1-(aminoiminomethyl)piperidin-4-yl]methoxy]-5-methylphenyl ester hydrochloride:

¹H-NMR (300 MHz, DMSO-d₆) δ 1.23 (m, 2H), 1.76 (d, J=13.3 Hz, 2H), 1.98 (m, 1H), 2.20 (s, 3H), 3.01 (t, J=12.2 Hz, 2H), 3.73 (d, J=6.2 Hz, 2H), 3.87(d, J=13.5 Hz, 2H), 6.25(br s, 2H), 6.35 (s, 1H), 6.47 (s, 1H), 6.58 (t, J=7.5 Hz, 1H), 6.71 (s, 1H), 6.97 (d, J=8.0 Hz, 1H),7.34 (t, J=8.3 Hz, 1H), 7.40 (br s, 3). Mass spectrum (MALDI-TOF, sinapinic acid matrix) calcd. for $C_{20}H_{26}N_4O_4S$: 419.2 (M+H), 441.2 (M+Na); Found: 419.1, 441.2 .

EXAMPLE 32

2-Chloro-3-nitrobenzenesulfonic acid 3-[[1-(aminoiminomethyl)piperidin-4-yl]methoxy-5-methylphenyl ester hydrochloride:

¹H-NMR (300 MHz, DMSO-d₆) δ 1.25 (m, 2H), 1.77 (d, J=11.3 Hz, 2H), 2.00 (m, 1H), 2.23 (s, 3H), 3.02 (t, J=11.8 Hz, 2H), 3.77 (d, J=6.2 Hz, 2H), 3.87 (d, J=13.8 Hz, 2H), 6.48 (s, 1H), 6.56 (s, 1H), 6.78 (s, 1H), 7.35 (br s, 4H), 7.83 (t, J=8.1 Hz, 1H), 8.24 (d, J=8.0 Hz, 1H), 8.47 (d, J=8.2 Hz, 1H). Mass spectrum (MALDI-TOF, sinapinic acid matrix) calcd. for $C_{20}H_{23}ClN_4O_6S$: 483.1 (M+H); Found: 483.0.

EXAMPLE 33

3-Amino-2-chlorobenzenesulfonic acid 3-[[1-(aminoiminomethyl)piperidin-4-yl]methoxy]-5-methylphenyl ester dihydrochloride:

¹H-NMR (300 MHz, DMSO-d6) δ 1.24 (m, 2H), 1.76 (d, J=11.3 Hz, 2H), 1.99 (m, 1H), 2.21 (s, 3H), 3.01 (t, J=12.6 Hz, 2H), 3.76 (d =6.0 Hz, 2H), 3.86 (d, J=13.0 Hz, 2H), 6.40 (br s, 2H), 6.49 (s, 1H), 6.73 (s, 1H), 7.08 (m, 1H), 7.18 (m, 2H), 7.38 (br s, 4). Mass spectrum (MALDI-TOF, sinapinic acid matrix) calcd. for $C_{20}H_{25}ClN_4O_4S$: 453.1 (M+H); Found: 453.4.

EXAMPLE 34

2-Chlorobenzenesulfonic acid 5-[[1-(aminoiminomethyl)piperidin-4-yl]methoxy]-2-(ethoxycarbonyl)-3-methylphenyl ester hydrochloride:

¹H-NMR (300 MHz, DMSO-d₆) δ 1.14–1.28 (m, 5H), 1.74 (d, J=12.96 Hz, 2H), 1.91–1.99 (m, 1H), 2.29 (s, 3H), 3.00 (t, J=12.02 Hz, 2H), 3.78 (d, J=6.2 Hz, 2H), 3.88 (d,

J=13.6 Hz, 2H), 4.14 (q, J=7.1 Hz, 2H), 6.29 (d, J=2.3 Hz, 1H), 6.90 (d, J=2.1 Hz, 1H), 7.46 (broad s, 3H), 7.59–7.64 (m, 1H), 7.82–7.97 (m, 3H). Mass spectrum (MALDI-TOF, sinapinic acid matrix) calcd. for $C_{23}H_{28}N_3O_6ClS$: 510.1 (M+H). Found: 510.4.

EXAMPLE 35

2-Chlorobenzenesulfonic acid 1-[[1-(aminoiminomethyl) piperidin-4-yl]methylnaphthalene-3-yl ester acetic acid salt:

$^1$H-NMR (300 MHz, DMSO-$d_6$)δ 7.75–8.1 (m, 5H), 7.51–7.59 (m, 3H), 7.19 (d, 1H), 6.67 (d, 1H), 3.83 –3.93 (m, 24H), 3.00 (t, 2H), 2.14 (br, 1H),1.86 (d, 2H), 1.64 (s,3H), and 1.28 –1.39 (m, 2H). Mass spectrum (MALDI-TOF; α-cyano-4-hydroxycinnamic acid matrix) calcd. for $C_{18}H_{23}ClN_4O_3S$: 474.1 (M+H). Found: 473.8.

EXAMPLE 36 a) 2-Chlorobenzenesulfonicacid3-hydroxy-5-methoxyphenylester:

The compound was produced by the method of step a of Example 7 from 5-methoxyresorcinol to give 2.61 g (83% yield) of a crystalline solid after column chromatography. $^1$H-NMR (CDCl$_3$; 300 MHz): δ 3.67 (s, 3H), 5.73 (s, 1H), 6.25–6.29 (m, 3H), 7.35–7.43 (m, 1H), 7.55–7.63 (m, 2H), 7.97 (dd, 1H).

b) 2-Chlorobenzenesulfonic acid 3-[[1-N-(tert-5 butoxycarbonyl)piperidin-4-yl]methoxy]-5-methoxyphenyl ester:

The compound was produced by the method of step b of Example 7 using the compound of the preceding step to give 1.71 g (81% yield) of a crystalline solid after column chromatography. $^1$H-NMR (CDCl$_3$; 300 MHz): δ 1.15–1.30 (m, 2H), 1.46 (s, 9H), 1.71–2.0 (m, 3H), 2.72 (t, 2H), 3.68 (s and d, 5H), 4.1–4.24 (m, 2H), 6.24–6.3 (m, 3H), 7.36–7.42 (m, 1H), 7.55–7.64 (m, 2H), 7.97 (dd, 1H).

c) 2-Chlorobenzenesulfonic acid 3-[[1-(aminoiminomethyl) piperidin-4-yl]methoxy]-5-methoxyphenyl ester:

The compound of the preceding step (1.8 g, 3.52 mmol) was treated with 25 mL of 25% trifluoroacetic acid in methylene chloride at ambient temperature for 15 min. The solvent was evaporated, the residue was azeotroped with acetonitrile (3 times), and placed under high vacuum. The residue was dissolved in methanol (30 mL) and treated with 1H-pyrazole-1-carboxamidine hydrochloride (1.03 g, 7.04 mmol) and triethylamine (1.39 mL, 10.5 mmol). The reaction mixture was stirred at ambient temperature overnight. The solvent was evaporated to dryness. The residue was placed under high vacuum, then treated with ethyl acetate and water. Upon shaking, a crystalline precipitate was produced, which was collected by filtration, and dried under high vacuum to give white solid. $^1$H-NMR (DMSO-$d_6$; 300 MHz): δ 1.25 (t, 2H), 1.76 (d, 2H), 2.0 (m, 1H ), 3.03 (q, 2H), 3.65 (s, 3H), 3.77 (d, 2H), 3.86 (d, 2H), 6.16 (s, 1H), 6.25 (s, 1H), 6.47 (s, 1H), 7.35 (s,4H), 7.59 (t, 1H), 7.8–7.98 (m, 3H). Mass spectrum (MALDI-TOF) calcd. for $C_{20}H_{24}N_3O_5SCl$: 454.1 (M+H). Found 454.0.

EXAMPLE 37 a) 2-Chlorobenzenesulfonic acid 3-hydroxy-4-ethoxycarbonyl-5-methylphenyl ester:

Ethyl 2,4-dihydroxy-6-methylbenzoate (1 g, 5 mmol) was dissolved in anhydrous methylene chloride (5 mL) and cooled in an ice bath. To this solution was added 2-chlorobenzenesulfonyl chloride (1.1 g, 5.2 mmol) and N,N-diisopropylethylamine (0.89 mL, 5.1 mmol). The mixture was stirred for 3 h under a nitrogen atmosphere. The reaction mixture was diluted with methylene chloride and washed sequentially with 10% HCl, aqueous NaHCO$_3$ and brine, dried over anhydrous MgSO$_4$, and concentrated in vacuo to give a white solid. Recrystallization from cold hexane to give 1.67 g of a white solid (90%). $^1$-NMR (DMSO-$d_6$; 300 MHz): δ 1.25 (t, J=7.1 Hz, 3H), 2.15 (s, 3H), 4.25 (q, J =7.1 Hz, 2H), 6.49–6.52 (m, 2H), 7.57–7.63 (m, 1H), 7.57–7.63 (m, 2H), 7.81–7.99 (m, 1H), 10.41 (s, 1H).

b) 2-Chlorobenzenesulfonic acid 3-[[1-(tert-butoxycarbonyl)piperidin-4-yl]methoxy]-4-ethoxycarbonyl-5-methylphenyl ester:

A solution of 2-chlorobenzenesulfonic acid 3-hydroxy-4-ethoxycarbonyl-5-methylphenyl ester (830 mg, 2.2 mmol), as prepared in the preceding step, N-(tert-butoxycarbonyl)-4-piperidinemethanol (483 mg, 2.2 mmol), as prepared in step f of Example 1, and triphenylphosphine (589 mg, 2.2 mmol) in tetrahydrofuran (15 mL) at 0° C. was treated with diethyl azodicarboxylate (390 mg, 2.2 mmol). The reaction mixture was stirred at 0° C. for 2 h and at room temperature overnight. The solvent was removed under vacuum and the residue was purified by flash column chromatography (1:3 ethyl acetate:hexane) to give 1.1 g (86%) of the title compound as an oil. $^1$H-NMR. (CDCl$_3$; 300 MHz): δ 1.16–1.29 (m,2H), 1.34 (t, J=7.1 Hz, 3H), 1.46 (s, 9H), 1.69–1.74 (m,2H), 1.83–1.92 (m, 1H), 2.2 (s, 3H), 2.66–2.74 (m, 2H), 3.71 (d, J=6.2 Hz, 2H), 4.09–4.16 (m, 2H), 4.34 (q, J=7.1 Hz, 2H), 6.53–6.56 (m, 2H), 7.38–7.43 (m, 1H), 7.57–7.65 (m, 2H), 7.94–7.98 (m, 1H).

c) 2-Chlorobenzenesulfonic acid 3-[(piperidin-4-yl) methoxy]-4-ethoxycarbonyl-5-methylphenyl ester hydrochloride:

2-Chlorobenzenesulfonic acid 3-[[1-(tert-butoxycarbonyl)piperidin-4-yl]methoxy]-4-ethoxycarbonyl-5-methylphenyl ester (800 mg, 1.44 mmol), as prepared in the preceding step, was treated with 4N dioxane in HCl for 3 h at which time ether was added to the mixture in order to precipitate the HCl salt. The precipitated solid was collected by filtration and washed with ether. Drying under vacuum gave 653 mg (90%) of a white solid. $^1$H-NMR (CDCl$_3$/CD$_3$OD; 300 MHz): δ 1.35 (t, J=7.1 Hz, 3H), 1.60–1.72 (m, 2H) 2.02–2.06 (m, 3H), 2.2 (s, 3H), 2.89–2.98 (m, 2H), 3.45–3.49 (m, 2H), 3.79 (d, J=6.0 Hz, 2H), 4.36 (q, J=7.1 Hz, 2H), 6.56–6.59 (m, 2H), 7.37–7.49 (m, 1H), 7.63–7.69 (m, 2H), 7.96–7.99 (m, 1H). Mass spectrum (MALDI-TOF) calcd. for $C_{22}H_{26}NO_6ClS$: 468.1 (M+H). Found 468.2.

d) 2-Chlorobenzenesulfonic acid 3-[[1-(aminoiminomethyl) piperidin-4-yl]method-4-ethoxycarbonyl-5-methylphenyl ester hydrochloride:

2-Chlorobenzenesulfonic acid 3-[(piperidin-4-yl) methoxy]-4-ethoxycarbonyl-5-methylphenyl ester hydrochloride (0.18 mmol), as prepared in the preceding step, was dissolved in anhydrous DMF and treated with 1H-pyrazole-1-carboxamidine hydrochloride (57.5 mg, 0.39 mmol) and triethylamine (TEA) (135 µL 0.96 mmol). This mixture was stirred for 1 day at which time more 1H-pyrazole-1-carboxamidine hydrochloride (29 mg) and TEA (67 µL) were added and the mixture was stirred for another day. The solvent was evaporated and the residue was dissolved in methylene chloride and washed with ice water. The methylene chloride layer was separated, dried over MgSO$_4$ and evaporated to give an oil. This oil was crystallized from methanol/ether. The solid was separated and triturated 3 times with hot ether to give a white solid, 55 mg (60%). $^1$H-NMR (CDCl$_3$/CD$_3$OD; 300 MHz); δ 1.33–1.46 (m, 5H), 1.87–1.91 (m, 2H), 2.0–2.07 (m, 1H), 2.2 (s, 3H), 2.99–3.07 (m, 2H), 3.78 (d, J=6.0 Hz, 2H), 3.9–4.0 (m, 2H), 4.35 (q, J=7.1 Hz, 2H), 6.55–6.61 (m, 2H), 7.39–7.50 (m, 1H), 7.63–7.69 (m, 2H), 7.96–7.99 (m, 1H). Mass spectrum (MALDI-TOF) calcd. for $C_{23}H_{28}N_3O_6ClS$: 510.1 (M+H). Found 510. 1.

EXAMPLE 38 a) 1-Benzyloxy-3-[N(tert-butoxycarbonyl)piperidin-4-yl] methoxy-5-methylbenzene:

A solution of 3-benzyloxy-5-methylphenol (2.0 g, 10 mmol), as prepared in step a of Example 3, N-(tert-butoxycarbonyl)-4-piperidinemethanol (2.15 g, 10 mmol), as prepared in step f of Example 1, and triphenylphosphine (2.62 g, 10 mmol) in tetrahydrofuran (40 mL) at 0° C. was treated with diethyl azodicarboxylate (1.74 g, 10 mmol). The reaction mixture was stirred at 0° C. for 2 h and at room temperature for 3 h. The reaction mixture was partitioned between ethyl acetate (200 mL) and water (50 mL). The organic extract was washed sequentially with saturated $NaHCO_3$ (2×50 mL) and brine (2×50 mL), dried over $Na_2SO_4$, and concentrated in vacuo. The residue was purified by flash column chromatography (1:3 ethyl acetate:hexane) to give the title compound as a colorless liquid (1.95 g, 47%). $^1H$-NMR (300 MHz, $CDCl_3H$): δ 1.26 (m, 2H), 1.46 (s, 9H), 1.80 (d, 2H), 1.92 (m, 1H), 2.29 (s, 3H), 2.74 (t, 2H), 3.76 (d, 2H), 4.12 (m, 2H), 6.34 (s, 1H), 6.35 (s, 1H), 6.42 (s, 1H), 7.41 (m, 5H).

b) 3-[N-(tert-Butoxycarbonyl)piperidin-4-yl]methoxy-5-methylphenol:

1-Benzyloxy-3-[N-(tert-butoxycarbonyl)piperidin-4-yl] methoxy-5-methylbenzene (1.65 g, 4.0 mmol), as prepared in the preceding step, in ethanol (50 mL) containing 10% palladium on carbon (200 mg) was hydrogenated (balloon) for 3 h. The catalyst was removed by filtration through diatomaceous earth (methanol washes) and the filtrate was concentrated in vacuo to give the title compound as as white solid (1.18 g, 92%). $^1H$-NMR (300 MHz, $CDCl_3$): δ 1.25 (m, 2H), 1.47 (s, 9H), 1.80 (d, 2H), 1.93 (m, 1H), 2.26 (s, 3H), 2.75 (t, 2H), 3.74 (d, 2H), 4.13 (m, 2H), 5.57 (s, 1H), 6.22 (t, 1H), 6.27 (dd, 2H).

c) 2-Trifluoromethylbenzenesulfonic acid 3-[[N-(tert-butoxycarbonyl)piperidin-4-yl]methoxy]-5-methylphenyl ester:

A solution of 3-[N-(tert-butoxycarbonyl)piperidin-4-yl] methoxy-5-methylphenol (321 mg, 1.0 mmol), as prepared in the preceding step, in methylene chloride (15 mL) at 0° C. was treated with N,N-diisopropylethylamine (0.5 mL) and 2-trifluoromethylbenzenesulfonyl chloride (245 mg, 1.0 mmol). The reaction mixture was stirred at 0° C. for 3 h. Ethyl acetate (150 mL) was added and the reaction mixture was washed with saturated $NaHCO_3$ (2×50 mL) and brine (2×50 mL), dried over $Na_2SO_4$, and concentrated in vacuo. The residue was purified by flash column chromatography (methylene chloride) to give the title compound as a yellow liquid (490 mg, 92%). $^1H$-NMR (300 MHz, $CDCl_3$): δ 1.25 (m, 2H), 1.47 (s, 9H), 1.77 (m, 2H), 1.89 (m, 1H), 2.25 (s, 3H), 2.73 (t, 2H), 3.69 (d, 2H), 4.13 (m, 2H), 6.44 (t, 1H), 6.46 (s, 1H), 6.60 (s, 1H), 7.70 (t, 1H), 7.80 (t, 1H), 7.99 (d, 1H), 8.13 (d, 1H).

d) 2-Trifluoromethiylbenzenesulfonic acid 3-[[1-(aminoiminomethyl)piperidin-4-yl]methoxy]-5-methylphenyl ester acetic acid salt:

2-Trifluoromethylbenzenesulfonic acid 3-[[N-(tert-butoxycarbonyl) piperidin-4-yl]methoxy]-5-methylphenyl ester (370 mg, 0.7 mmol), as prepared in the preceding step, was treated with 10 mL of 4N HCl in 1,4-dioxane and stirred at room temperature for 2 h. The solvent was evaporated in vacuo and then concentrated from methylene chloride several times to give the amine salt. This was then dissolved in DMF (10 mL) and treated with triethylamine (0.4 mL) and aminoiminomethanesulfonic acid (186 mg, 1.5 mmol). The reaction mixture was stirred at room temperature overnight. The DMF was removed in vacuo and the residue was then dissolved in methylene chloride (200 mL), washed with 10% $K_2CO_3$ (3×50 mL), dried over $K_2CO_3$ and concentrated in vacuo. The residue was purified by flash column chromatography (88:10:2 methylene chloride:methanol:acetic acid) and crystallized from acetonitrile-ethyl ether to give the title compound as a white solid (270 mg, 72%). $^1H$-NMR (300 MHz, $CD_3OD$): δ 1.42 (m, 2H), 1.90 (s, 3H), 1.94 (m, 2H), 2.10 (m, 1H), 2.22 (s, 3H), 3.12 (dt, 2H), 3.79 (d, 2H), 3.85 (d, 2H), 6.39 (s, 1H), 6.43 (t, 1H), 6.70 (s, 1H), 7.81 (t, 1H), 7.94 (t, 1H), 8.09 (d, 2H). Mass spectrum (MALDI-TOF, sinapinic acid matrix) calcd. for $C_{21}H_{24}N_3O_4SF_3$: 472.2 (M+H$^+$), 494.1 (M+Na$^+$). Found: 472.7, 494.6.

EXAMPLE 39 a) 3-Methylbenzenesulfonic acid 3-[[N-(tert-butoxycarbonyl)piperidin-4-yl]methoxy]-5-methylphenyl ester:

A solution of3-[N-(tert-butoxycarbonyl)piperidin-4-yl] methoxy-5-methylphenol (321 mg, 1.0 mmol), as prepared in step b of Example 20, in methylene chloride (15 mL) at 0° C. was treated with N,N-diisopropylethylamine (0.5 mL) and 3-methylbenzenesulfonyl chloride (191 mg, 1.0 mmol). The reaction mixture was stirred at 0° C. for 3 h. The reaction mixture was extracted with ethyl acetate (3×50 mL), washed sequentially with saturated $NaHCO_3$ (2×50 mL) and brine (2×50 mL), dried over $Na_2SO_4$, and concentrated in vacuo. The residue was purified by flash column chromatography (methylene chloride) to give the title compound as a yellow oil (425 mg, 89%). $^1H$-NMR (300 MHz, $CDCl_3$): δ 1.24 (m, 2H), 1.47 (s, 9H), 1.76 (m, 2H), 1.89 (m, 1H), 2.24 (s, 3H), 2.43 (t, 3H), 2.73 (t, 2H), 3.66 (d, 2H), 4.13 (m, 2H), 6.33 (t, 1H), 6.38 (s, 1H), 6.59 (s, 1H), 7.44 (dt, 2H), 7.65 (dd, 2H).

b) 3-Methylbenzenesulfonic acid 3-[[1-(aminoiminomethyl)piperidin-4-yl]methoxy]-5-methylphenyl ester acetic acid salt:

3-Methylbenzenesulfonic acid 3-[[N-(tert-butoxycarbonyl)piperidin-4-yl]methoxy]-5-methylphenyl ester (380 mg, 0.8 mmol), as prepared in the preceding step, was treated with 10 mL of 4N HCl in 1 ,4-dioxane and stirred at room temperature for 2 h. The solvent was evaporated in vacuo and concentrated from methylene chloride several times to give the amine salt. This was then dissolved in DMF (10 mL) and treated with triethylamine (0.5 mL) and aminoiminomethanesulfonic acid (200 mg, 1.6 mmol). The reaction mixture was stirred at room temperature overnight. The DMF was removed in vacuo. The residue was dissolved in methylene chloride (200 mL), washed with 10% $K_2CO_3$ (3×50 mL), dried over $K_2CO_3$ and concentrated in vacuo. The residue was purified by flash column chromatography (88:10:2 methylene chloride:methanol:acetic acid) and crystallized from acetonitrile/ethyl ether to give the title compound as a white solid (295 mg, 76%). $^1H$-NMR (300 MHz, $CD_3OD$): δ 1.41 (m, 2H), 1.89 (s, 3H), 1.92 (m, 2H), 2.08 (m, 1H), 2.21 (s, 3H), 2.42 (s, 3H), 3.12 (dt, 2H), 3.76 (d, 2H), 3.92 (d, 2H), 6.35 (d, 2H), 6.67 (s,3H), 7.48 (t, 1H), 7.60 (m, 3H). Mass spectrum (MALDI-TOF, sinapinic acid matrix) calcd. for $C_{21}H_{27}N_3O_4S$: 418.2 (M+H), 440.2 (M+Na). Found: 418.4, 440.6.

EXAMPLE 40 a) 3,5-Dibenzyloxybenzaldehyde:

To a solution of 2.39 g (17.3 mmol) of 3,5-dihydroxybenzaldehyde in 10 mL of DMF at 0° C. under a nitrogen atmosphere was added slowly 831 mg (34.6 mmol)

of NaH (100%). After hydrogen evolution had ceased, 5.4 mL (37 mmol) of benzyl bromide was added. The ice bath was removed and the reaction mixture was stirred to room temperature for 1 h. The reaction mixture was quenched and acidified with aqueous HCl, extracted into ether, and washed with 1N NaOH followed by a washing with 1N HCl. The organic extract was dried (MgSO$_4$) and the product was purified by flash chromatography (20 to 30% ether/hexane) to give 3.28 g (60% yield) of the title compound as a colorless solid. $^1$H-NMR (300 MHz, CDC$_3$) δ 9.90 (s, 1H), 7.3–7.5 (m, 10H), 7.11 (d, 2H, J=2 Hz), 6.87 (t,1H, J=2 Hz), and 5.09 (s, 4H).

b) 5-Vinylresorcinol dibenzylether:

To 2.3 g (6.43 mmol) of methyltriphenylphosphonium bromide in 15 mL of anhydrous DMSO at ambient temperature was added 160 mg (6.7 mmol) of NaH. The reaction mixture was stirred for 40 min. To the resulting yellow suspension was added 1.8 g (5.84 mmol) of 3,5-dibenzyloxybenzaldehyde, as prepared in the preceding step. Tetrahydrofuran (5 mL) was added to the reaction mixture. After 10 min, a colorless suspension resulted. The reaction was stirred for 30 min, quenched with 5% aqueous citric acid, extracted into ethyl acetate/tetrahydrofuran, washed with 4×50 mL H$_2$O, dried (MgSO$_4$), and concentrated in vacuo. The product was purified by flash chromatography (methylene chloride/hexane (1:4 to 1:3H)) to give 1.65 g (81% yield) of the title compound. $^1$H-NMR (300 MHz, CDCl$_3$H) δ 6 7.2–7.45 (m, 10H), 6.67 (d, 1H, J=2 Hz), 6.63 (dd, 1H, J=11, 17 Hz), 6.54 (t, 1H), J=2 Hz), 5.70 (d, 1H, J=11 Hz), 5.24 (d, 1H, J=17 Hz), 5.04 (s, 4H). Mass spectrum (MALDI-TOF; gentisic acid matrix) calcd. for C$_{22}$H$_{20}$O$_2$:317.2 (M+H), 339.1 (M+Na). Found: 317.6, 339.0.

c) 5-Ethylresorcinol

A mixture of 1.07 g (3.39 mmol) of 5-vinylresorcinol dibenzylether, as prepared in the preceding step, and 200 mg of 10% Pd/C in 20 mL of ethanol was hydrogenated at atmospheric pressure and ambient temperature for 14 h. The reaction mixture was filtered through diatomaceous earth (ethanol rinse) and concentrated to give 511 mg of the crude title compound which was used as is in the next reaction. $^1$H-NMR (300 MHz, CDCl$_3$): δ 6 6.27 (dd, 1H, J=0.4, 2.2 Hz), 6.18 (t, 2H), 2.53 (q, 2H), 1.19 (t, 3H). Mass spectrum (MALDI-TOF; sinapinic acid matrix) calcd. for C$_8$H$_{10}$O$_2$:139.1 (M+H). Found: 139.5.

d) 2-Chlorobenzenesulfonic acid 3-hydroxy-5-ethylphenyl ester:

A biphasic mixture of 298 mg (2.25 mmol) of 5-ethylresorcinol, as prepared in the preceding step, 714 mg (3.38 mmol) of 2-chlorobenzenesulfonyl chloride in 10 mL of ether and 10 mL of saturated NaHCO$_3$ was vigorously stirred for 3 days. The reaction mixture was extracted into a mixture of ethyl acetate/ether, washed with saturated NaHCO$_3$, and dried (MgSO$_4$H). Concentration in vacuo and purification by flash chromatography (methylene chloride:ether (98:2 to 95:5)) gave 324 mg (47% yield) of the title compound as a colorless oil. $^1$H-NMR (300 MHz, CDCl$_3$): δ 7.95 (dd, 1H, J=2, 7 Hz), 7.55–7.64 (m, 2H), 7.34–7.40 (m, 1H), 6.56 (m, 1H), 6.51 (m, 1H), 6.47 (t, 1H), 5.22 (bs, 1H), 2.50 (q, 2H), 1.26 (t, 3H). Mass spectrum (MALDI-TOF; gentisic acid matrix) calcd. for C$_{14}$H$_{13}$ClO$_4$S: 335.0 (M+Na). Found: 334.9.

e) 2-Chlorobenzenesulfonic acid 3-[1-N-(tert-butoxycarbonyl)-piperidin-4-yl-5-ethylphenyl ester:

To a solution of 324 mg (1.06 mmol) of 2-chlorobenzenesulfonic acid 3-hydroxy-5-ethylphenyl ester, as prepared in the preceding step, in 5 mL of tetrahydrofuran containing 314 mg (1.46 mmol) of N-tert-butoxycarbonyl-4-piperidinemethanol, as prepared in step f of Example 1, 400 μL (3.6 mmol) of N-methylmorpholine, and 416 mg (2.53 mmol) of triphenylphosphine was added 250 μL (1.59 mmol) of diethyl azodicarboxylate. The reaction mixture was stirred at ambient temperature for 14 h, quenched with H$_2$O, and extracted into ethyl acetate. The organic phase was dried (MgSO$_4$H) and concentrated in vacuo. Purification by flash chromatography (ether:methylene chloride 1:99H) gave 427 mg (80% yield) of the title compound as a colorless oil. $^1$H-NMR (300 MHz, CDCl$_3$H): δ 8 7.96 (dd, 1H, J=1, 7 Hz), 7.55–7.64.(m, 2H), 7.34–7.40 (m, 1H), 6.59 (m, 1H), 6.49–6.56 (m, 2H), 4.13 (br, 2H), 3.69 (d, 1H, J=6 Hz), 2.73 (t, 2H, J=12 Hz), 2.51 (q, 2H), 1.84–1.95 (m, 1H), 1.77 (br d, 2H), 1.46 (s, 9H), 1.21 (t, 3H). Mass spectrum (MALDI-TOF; gentisic acid matrix) calcd. for C$_{25}$H$_{32}$ClNO$_6$S: 532.2 (M+Na). Found: 532.5, 410.1 (M-(tert-butoxycarbonyl) +H).

f) 2-Chlorobenzensulfonic acid 3-[|piperidin-4-yl] methoxy]-5-ethylphenyl ester hydrochloride:

A solution of 420 mg (0.834 mmol) of 2-chlorobenzenesulfonic acid 3-[1-N-(tert-butoxycarbonyl) piperidin-4-yl] methoxy]-5-ethylphenyl ester, as prepared in the preceding step, in 2 mL of methylene chloride was treated with 2 mL of 4N HCl in dioxane. The reaction mixture was stirred for 1 h at ambient temperature and then concentrated repeatedly from ether/methylene chloride to provide 373 mg (91% yield) of the title compound as a foam. $^1$H-NMR (300 MHz, CDCl$_3$H): δ 9.72 (bs, 1H), 9.42 (bs, 1H), 7.96 (dd, 1H, J=1, 7 Hz), 7.57–7.66 (m, 2H), 7.35–7.41 (m, 1H), 6.59 (s, 1H), 6.52 (s, 1H), 6.49 (t, 1H), 3.74 (d, 2, J=5 Hz), 3.57 (d, 2, J=11 Hz), 2.92 (br, 2H), 2.52 (q, 2H), 2.05bd,2H), 1.80 (br t, 2H), 1.10 (t, 3H). Mass spectrum (MALDI-.TOF; gentisic acid matrix) calcd. for C$_{20}$H$_{24}$ClN$_4$S: 410.1 (M+H), 432.1 (M+Na). Found: 410.6, 432.6.

g) 2-Chlorobenzenesulfonic acid 3-[[1-(aminoiminomethyl) piperidin-4-yl] methoxy]-5-ethylphenyl ester hydrochloride:

2-Chlorobenzenesulfonic acid 3-[|piperidin-4-yl] methoxy]-5-ethylphenyl ester hydrochloride (313 mg), as prepared in the preceding step, was dissolved in methylene chloride (20 mL) and washed with saturated NaHCO$_3$ (20 mL), dried (K$_2$CO$_3$H), and concentrated to provide the free base (307 mg) as an oil. This was diluted with 2 mL of DMF and then treated with 680 μL (6.18 mmol) of N,N-diisopropylethylamine, and 227 mg (1.55 mmol) of 1H-pyrazole-1-carboxamidine hydrochloride. The reaction mixture was stirred at ambient temperature overnight. The reaction mixture was quenched with saturated Na$_2$CO$_3$ then 1N NaOH, extracted into methylene chloride/tetrahydrofuran, dried (K$_2$CO$_3$) and concentrated. The residue was dissolved in a minimal amount of methylene chloride, treated with 2 mL of 4N HCl in dioxane and concentrated. Silica gel chromatography (10 g Water's Associates Silica gel Sep Pak SPE column) with elutions of methylene chloride: methanol (4:1) did not remove fully pyrazole contamination. Purification of 75 mg of the crude material was accomplished by preparative (two 1000 micron plates, 20×20 cm) silica gel thin layer chromatography (methylene chloride:methanol (4:1)) to provide pure product. To insure complete HCl salt formation, the material was dissolved in methylene chloride and treated with 500 μL of 4N HCl in dioxane. Repeated concentrations from toluene/methylene chloride provided the title compound (65 mg) as a white powder. $^1$H-NMR (300 MHz, CDCl$_3$): δ 7.95 (d, 1H), 7.57–7.65 (m, 2H), 7.33–7.41 (m, 1H), 6.59 (s, 1H), 6.48–6.50 (m, 2H), 4.04 (br s, 2H), 3.72 (d, 2 H, J=3 Hz), 3.09 (br s, 3H), 2.50 (q, 2H), 1.93–2.09 (m, 3H), 1.09 (t, 3H). Mass spectrum (MALDI-TOF; gentisic acid matrix) calcd. for $C_{21}H_{26}ClN_3O_4S$: 452.1 (M +H, $^{35}Cl$) and 454.1 (M +H, $^{37}Cl$). Found: 452.5 and 454.6.

EXAMPLE 41 a) 2-Chlorobenzenesulfonic acid 3-||5-(N-tert-butoxycarbonyl)amino|pentoxy|-5-methylphenyl ester:

A solution of 2-chlorobenzenesulfonic acid 3-hydroxy-5-methylphenyl ester (600 mg, 2.0 mmol), as prepared in step c of Example 3, N-(tert-butoxycarbonyl)-5-aminopentanol (426 mg, 2.0 mmol) and triphenylphosphine (525, mg, 2.0 mmol) in tetrahydrofuran (20 mL) at 0° C. was treated with diethyl azodicarboxylate (349 mg, 2.0 mmol). The reaction mixture was stirred it 0° C. for 2 h and at room temperature for 3 h. Water (50 mL) was added and the reaction mixture was extracted into ethyl acetate (3×50 mL). The organic phase was washed sequentially with saturated $NaHCO_3$ (2×50 mL) and brine (2×50 mL), dried over $Na_2SO_4$ and concentrated in vacuo. The residue was purified by flash column chromatography (1:2 ethyl acetate:hexane) to give the title compound as a colorless oil (819 mg, 85%). $^1$H-NMR (300 MHz, $CDCl_3$): δ 1.45 (s, 9H), 1.52 (m, 4H), 1.69 (m, 2H), 2.24 (s, 3H), 3.13 (t, 2H), 3.82 (t, 2H), 4.57 (bs, 1H),6.45 (s, 1H), 6.52 (d, 1H), 6.58 (s, 1H), 7.38 (t, 1H), 7.62 (m, 2H), 7.96 (dd, 1H).

b) 2-Chlorobenzenesulfonic acid 3-|[5(aminoiminomethyl)amino|pentoxy|-5-methylphenyl ester hydrochloride:

2-Chlorobenzenesulfonic acid 3-|[5-(N-tert-butoxycarbonyl)amino|pentoxy]-5-methylphenyl ester (484 mg, 1.0 mmol), as prepared in the preceding step, was treated with 1.0 mL of 4N HCl in 1,4-dioxane and stirred at room temperature for 2 h. The solvent was removed in vacuo and the residue concentrated from methylene chloride several times to give the amine salt. The salt was dissolved in DMF (10 mL) and treated with triethylamine (0.5 mL) and 1H-pyrazole-1-carboxamidine hydrochloride (220 mg, 1.5 mmol). The reaction mixture was stirred at room temperature for 2 days. The DMF was removed in vacuo. The residue was dissolved in methylene chloride (200 mL), washed with 10% $K_2CO_3$ (3×50 mL), dried over $K_2CO_3$, and concentrated in vacuo. The residue was acidified with 4N HCl in 1,4-dioxane (0.5 mL) and purified by flash column chromatography (10% methanol in methylene chloride) to give the title compound as a colorless foam (325 mg, 70%). $^1$H-NMR (300 MHz, $CDCl_3$H): δ 1.52 (m, 2H), 1.67 (m, 2H), 2.07 (m, 2H), 2.19 (s, 3H), 3.21 (t, 2H), 3.79 (t, 2H), 6.45 (s, 1H), 6.47 (s, lH), 6.56 (s, 1H), 7.37 (t, 1H), 7.60 (m, 2H), 7.94 (d, 1H). Mass spectrum (MALDI-TOF, sinapinic acid matrix) calcd. for $Cl_{19}H_{24}N_3O_4SCl$: 426.1 (M+H). Found: 426.1

EXAMPLE 42 a) 2,3-Dichlorobenzenesulfonic acid 3-hydroxy-5-methylphenyl ester:

A mixture of Orcinol monohydrate (0.71 g, 5.0 mmol) and 2,3-dichlorobenzenesulfonyl chloride (1.23 g, 5.0 mmol) in saturated $NaHCO_3$ (20 mL) and ethyl ether (20 mL) was stirred vigorously at room temperature for 2 days. The reaction mixture was partitioned between ethyl acetate (200 mL) and water (50 mL). The organic extract was washed with brine (2×50 mL), dried over $Na_2SO_4$ and concentrated in vacuo. The residue was purified by flash column chromatography (methylene chloride to 2% ethyl acetate in methanol) to give the title compound as a pale-yellow liquid (0.89 g, 55%). $^1$H-NMR (300 MHz, $CDCl_3$): δ 2.24 (s, 3H), 5.23 (s, 1H), 6.43 (t, 1H), 6.54 (dd, 2H), 7.34 (t, 1H), 7.75 (dd, 1H), 7.91 (dd, 1H).

b) 2,3-Dichlorobenzenesulfonic acid 3-||N-(tert-butoxycarbonyl)piperidin-4-yl| methoxy|-5-methylphenyl ester:

A solution of 2,3-dichlorobenzenesulfonic acid 3-hydroxy-5-methylphenol (644 mg, 2.0 mmol), as prepared in the preceding step, N-(tert-butoxycarbonyl)-4-piperidinemethanol (430 mg, 2.0 mmol), as prepared in step f of EXAMPLE 1, and triphenylphosphine (525 mg, 2.0 mmol) in tetrahydrofuran (20 mL) at 0° C. was treated with diethyl azodicarboxylate (349 mg, 2.0 mmol). The reaction mixture was stirred at 0° C. for 2 h and at room temperature for 3 h. The reaction mixture was diluted with water (50 mL), and extracted into ethyl acetate (3×50 mL). The organic extract was washed sequentially wit saturated $NaHCO_3$ (2×50 mL) and brine (2×50 mL), dried over $Na_2SO_4$, and concentrated in vacuo. The residue was purified by flash column chromatography (1:3 ethyl acetate:hexane) to give the title compound as a colorless syrup (930 mg, 88%). $^1$H-NMR (300 MHz, $CDCl_3$): δ 1.26 (m, 2H), 1.47 (s, 9H), 1.75 (m, 2H), 1.90 (m, 1H), 2.25 (s, 3H), 2.73 (t, 2H), 3.68 (d, 2H), 4.13 (m, 2H), 6.47 (d, 1H), 6.53 (d, 1H), 6.59 (s,1H), 7.34 (t, 1H), 7.75 (dd, 1H), 7.92 (dd, 1H).

c) 2,3-Dichlorobenzenesulfonic acid 3-||1-(aminoiminomethyl)piperidin-4-yl| methoxy|-5-methylphenyl ester hydrochloride:

2,3-Dichlorobenzenesulfonic acid 3-|[N-(tert-butoxycarbonyl) piperidin-4-yl|methoxy|-5-methylphenyl ester (530 mg, 1.0 mmol), as prepared in the preceding step, was treated with 10 mL of 4N HCl (in 1,4-dioxane) and stirred at room temperature for 2 h. The solvent was evaporated in vacuo and concentrated from methylene chloride several times to give the amine salt. The salt was dissolved in DMF (10 mL) and treated with triethylamine (0.5 mL) and 1H-pyrazole-1-carboxamidine hydrochloride (293 mg, 2.0 mmol). The reaction mixture was stirred at room temperature for 2 days. The DMF was removed in vacuo. The residue was dissolved in methylene chloride (200 mL), washed with 10% $K_2CO_3$ (3×50 mL), dried over $K_2CO_3$, and concentrated in vacuo. The residue was acidified with 4N HCl in 1 ,4-dioxane (0.5 mL) and purified by flash column chromatography (10% methanol in methylene chloride) to give the title compound as a colorless foam (245 mg, 48%). $^1$H-NMR (300 MHz, $CDCl_3$): δ 1.43 (m, 2H), 1.92 (m, 2H), 2.01 (m, 1H), 2.22 (s, 3H), 3.08 (t, 2H), 3.71 (d, 2H), 4.10 (m, 2H), 6.49 (s, 2H), 6.58 (s, 1H), 7.30 (bs, 4H), 7.36 (t, 1H), 7.77 (d, 1H), 7.91 (d, 1H). Mass spectrum (MALDI-TOF, sinapinic acid matrix) calcd. for $C_{20}H_{23}N_3O_4SCl_2$: 472.1 (M+H) Found: 472.0.

EXAMPLE 43 a) 2-Chlorobenzenesulfonic acid 3-hydroxynaphthalen-1-yl ester:

To a solution of 1.0 g (6.24 mmol) of 1,3-dihydroxynaphthalene in methylene chloride (20 mL) containing 1.4 mL (12.8 mmol) of N-methylmorpholine was added 1.35 g (6.40 mmol) of 2-chlorobenzenesulfonyl chloride. The reaction mixture was stirred overnight at ambient temperature, quenched with 1N HCl, and extracted into ether. The organic phase was dried ($MgSO_4$) and concentrated in vacuo. The product was purified by flash chromatography (methylene chloride:ether (100:0 to 95:5)) to give impure title compound (205 mg, 9.8% yield; contamination with 3-isomer). $^1$H-NMR (300 MHz, DMSO-$d_6$) δ 8.03 (d, 1 H, J=7 Hz), 7.2–7.7 (m, 7H), 7.07 (d, 1H), 6.89 (d, 1H), 5.38 (bs, 1H). A difference nOe experiment (irradiation at phenolic H) determined the regioisomeric composition of the major product in which enhancements of the proton doublets at 6.89 at 7.07 ppm were observed. Mass spectrum (MALDI-TOF gentisic acid matrix) calcd. for $C_{16}H_{11}ClO_4S$: 335.0 (M+H) and 357.0 (M+Na). Found: 334.4, 356.8.

b) 2-Chlorobenzenesulfonic acid 3-||1-N-(tert-butoxycarbonyl)piperidin-4-yl| methoxy|naphtlalen-1-yl ester:

To 205 mg (0.613 mmol) of the mixture of 2-chlorobenzenesulfonic acid 3-hydroxynaphthalen- 1 -yl ester, contaminated with 2-chlorobenzenesulfonic acid 1 -hydroxynaphthalen-3-yl ester, as prepared in the preceding step, in methylene chloride (3 mL) containing 209 mg (0.80 mmol) of triphenylphosphine, 140 mg (1.46 mmol) of N-tert-butoxycarbonyl-4-piperidinemethanol, as prepared in step f of Example 1, and 400 μL (3.6 mmol) of N-methylmorpholine was added 225 μL (0.796 mmol) of diethyl azodicarboxylate. The reaction mixture was stirred at ambient temperature for 30 min, quenched with $H_2O$, and extracted into ether. The organic phase was dried (MgSO₄) and concentrated in vacuo. Partial purification was accomplished by flash chromatography (13% ether/methylene chloride) to give 173 mg (53% yield) of the title compound as a colorless hardened oil, contaminated with ca. 20% of the 1,3-regioisomer. ¹H-NMR (300 MHz, CDCl₃H): δ 8.00–8.05 (m, 2H), 7.30–7.70 (m, 6H), 7.03 (d, 1H), 6.91 (s, 1H), 4.18 (bs, 2H), 3.85 (d, 2H), 2.76 (t, 2H), 1.8–2.0 (m, 2H), 1.81 (d, 2 H), 1.48 (s, 9H).

c) 2-Chlorobenzenesulfonic acid 3-|(piperidin-4-yl) methoxy|naphthalen-1-yl ester hydrochloride:

A solution of 153.7 mg (0.289 mmol) of 2-chlorobenzenesulfonic acid 3-[[1 -N-(tert-butoxycarbonyl) piperidin-4-yl]methoxy] naphthalen-1-yl ester, as prepared in the preceding step, in methylene chloride (2 mL) was treated with 500 μL of 4N HCl in dioxane. The reaction mixture was stirred at ambient temperature for 1 h. Concentration in vacuo and repeated concentrations from methylene chloride/ether/hexane gave 143 mg of crude title compound (contaminated with ca. 20% 1,3-regioisomer) which was used as is in the next reaction. 1H-NMR (300 MHz, CDCl₃): δ 9.75 (bs, 1H), 9.46 (bs, 1H), 8.02–8.05 (m, 2H), 7.3–7.7 (m, 6H), 7.02 (d, 1H, J=2 Hz), 6.93 (d, 1H, J=2 Hz), 3.91 (d, 2H), 3.60 (d, 1H), 2.96 (bs, 2H), 2.03–2.17 (m, 3H), 1.80–1.88 (m, 2H). Mass spectrum (MALDI-TOF; gentisic acid matrix) calcd. for $C_{22}H_{22}ClN_4O_4S$: 432.1 (M+H). Found: 432.0.

d) 2-Chlorobenzenesulfonic acid 3-[[1-aminoiminomethyl) piperidin-4-yl] methoxy|naphthalen-1-yl ester hydrochloride:

A solution of 124.6 mg (0.266 mmol) of 2-chlorobenzenesulfonic acid 3-[[piperidin-4-yl]methoxy] naphthalen-1-yl ester hydrochloride, as prepared in the preceding step, in 2 mL of DMF was treated with 260 μL (2.34 mmol) of N,N-diisopropylethylamine, and 60 mg (0.40 mmol) of 1H-pyrazole-1-carboxamidine hydrochloride was stirred at ambient temperature for 2 days. The reaction mixture was concentrated to remove DMF. The residue was then treated with 25 mL of methylenechloride and 3 mL of 1N NaOH. The organic phase was separated, dried ($K_2CO_3$), and concentrated. The residue was dissolved in 1 mL of methylene chloride and treated with 200 μL of acetic acid. Preparative thin layer chromatography (two×1000 micron silica gel plates, 20×20 cm) using methylene chloride:methanol:acetic acid (93.6:6.5:0.5) gave 45 mg of the title compound as a white powder after concentration from methylene chloride/ether/methylene chloride/hexane. ¹H-NMR (300 MHz, CDCl₃): δ 8.01 (dd, 1H, J=2, 8 Hz), 7.82–7.94 (m, 4H), 7.51–7.63 (m, 2H), 7.39–7.44 (m, 2H), 6.75 (d, 1H), 3.93 (d,2 H, J=6 Hz), 3.86 (d, 2 H, J=12 Hz), 2.96 (t, 2 H, J=12 Hz), 1.9–2.1 (bs, 2H), 1.19–1.30 (m, 2H). Mass spectrum (MALDI-TOF; gentisic acid matrix) calcd. for $C_{23}H_{24}ClN_3O_4S$: 474.1 (M+H). Found: 474.5.

EXAMPLE 44 a) 2-Chlorobenzenesulfonic acid 3-||1-N-(tert-butoxycarbonyl)piperidin-4-yl| methoxy|-5-hydroxyinethylphenyl ester:

A solution of 2-chlorobenzenesulfonic acid 3-||1-(aminoiminomethyl) piperidin-4-yl| methoxy|-5-carbomethoxyphenyl ester (1.34 g, 2.49 mmol), as prepared in step b of Example 7 in tetrahydrofuran (30 mL) was treated with lithium borohydride (1.52 mL of 2M in tetrahydrofuran, 3.0 mmol) and then warmed to 50° C. After 3.5 h, an additional 0.5 mL of 2M lithium borohydride was added and warming was continued for a total of 10 h. The reaction was quenched with methanol and evaporated to dryness. The residue was treated with diethyl ether and methylene chloride/acetonitrile. The filtrate was evaporated to an oil, which was purified by silica gel chromatography with 30% ethyl acetate in hexanes to give 0.78 g (61% yield). Mass spectrum (MALDI-TOF) calcd. for $C_{24}H_{30}N_1O_7SCl$: 412.2 (M-tert-butoxycarbonyl +H). Found: 412. 1.

b) 2-Chlorobenzenesulfonic acid 3-||1-(aminoiminomethyl) piperidin-4-yl| methoxy]-5-hydroxymethylphenylester. The N-tert-butoxycarbonyl group of the compound of the preceding step (0.78 g, 1.53 mmol) was removed by treatment with 25% trifluoroacetic acid (12 mL) in methylene chloride at ambient temperature for 15 min. The reaction mixture was evaporated to dryness, then treated with acetonitrile and evaporated to dryness (3 times). ¹H-NMR (CDCl₃; 300 MHz): δ 1.61–1.78 (m, 2H), 2.09 (m, 3H), 2.49 (s, 2H), 2.93 (m, 2H), 3.46–3.53 (m, 2H), 3.78 (d, 2H), 4.60 (s, 1H), 6.59–6.81 (m, 3H), 7.36–7.43 (m, 1H), 7.57–7.66 (m, 2H), 7.96 (m, 1H), 8.89 (m, 1H), 9.45 (m, 1H). This material was dissolved in methanol (15 mL) and treated with triethylamine (0.64 mL, 4.59 mmol) a d 1H-pyrazole-1-carboxamidine hydrochloride (0.45 g, 3.06 mmol) and allowed to stir at ambient temperature over 4.5 days. The methanol was evaporated and the residue was placed under high vacuum. The residue was dissolved in acetonitrile and diluted with diethyl ether. The precipitate was filtered off and the filtrate was evaporated to dryness. The residue was dissolved in methanol and diluted with water to produce a flocculent precipitate which was recrystallized from methanol/water. The white solid was collected by filtration and dried under high vacuum to give 210 mg. ¹H-NMR (DMSO-d₆; 300 MHz): δ 1.24 (m, 2H), 1.77 (d, 2H), 2.0 (m, 1H), 3.01 (t, 2H), 3.78 (d, 2H), 3.87 (d, 2H), 4.39 (s, 2H), 6.50 (t,1H), 6.64 (s, H), 6.84 (s, 1H), 7.42 (m, 4H), 7.58 (dt, 1H), 7.8–7.96 (m, 3H). Mass spectrum (MALDI-TOF): calcd. for $C_{20}H_{24}N_3O_5SCl$: 454.1 (M+H). Found: 454.0.

EXAMPLE 45 a) 3-Trifluoromethyl-5-nitrophenol:

3-Methoxy-5-nitrobenzotrifluoride (5 g, 23 mmol) was dissolved in anhydrous methylene chloride (100 mL) and cooled to −80° C. under a nitrogen atmosphere. To this solution was added via dropping funnel a 1M solution of BBr₃ in methylene chloride (67.8 mL, 69 mmol). This solution was allowed to warm to room temperature and stirred for 3 days. Water was slowly added to the mixture and mixed well to quench the excess BBr₃. To this mixture ether (500 mL) was added. The organic layer was separated and extracted with 2N NaOH (240 mL). The alkaline extract was neutralized with dilute HCl and extracted with ether (3×300 mL). The ether extracts were combined, washed with saturated NaCl and dried over anhydrous MgSO$_4$. Evaporation of ether gave a brownish yellow oil which was chromatographed on a silica column to give 1.6 g (34%) of a yellow solid. $^1$H-NMR (CDCl$_3$/CD$_3$OD; 300 MHz): δ 7.38-7.40 (m, 1H), 7.82 (t, J=2.2 Hz, 1H), 7.95-7.96 (m, 1H).

b) 3-[[1-(tert-Butoxycarbonyl)piperidin-4-yl]methoxyl-5-nitrobenzotrifluoride:

The title compound was synthesized by treating 3-(trifluoromethyl)-5-nitrophenol (1.47 g, 7.1 mmol), as prepared in the preceding step, in a manner analogous to step b of Example 19 to give 2.17 g (76%) as an oil. $^1$H-NMR (CDCl$_3$, 300 MHz): δ 1.24-1.38 (m, 2H), 1.48 (s, 9H), 1.82-1.87 (m, 2H), 1.96-2.10 (m, 1H), 2.73-2.81 (m, 2H), 3.93 (d, J=6.3 Hz, 2H), 4.09-4.21 (m, 2H), 7.45-7.46 (m, 1H), 7.89 (t, J=2.2 Hz, 1H), 8.07-28.08 (m, 1H).

c) 2-Chloro-N-{3-[[1-(tert-butoxycarbonyl)piperidin4-yl]methoxy]-5-[trifluoromethyl]phenyl}benzenesulfonamide:

To a methanolic solution of 3-[(piperidin-4-yl)methoxy]-5-nitrobenzotrifluoride (2.17 g in 200 mL), as prepared in the preceding step, and 10% Pd/C (300 mg) was stirred under a hydrogen atmosphere for 20 h. The catalyst was removed by filtration and the methanol was evaporated to give a white foam. The foam was dried under high vacuum overnight and dissolved in anhydrous methylene chloride (10 mL). The methylene chloride solution was cooled in an ice bath under a nitrogen atmosphere. To this solution, 2-chlorobenzenesulfonyl chloride (1.17 g, 5.5 mmol) and N-methylmorpholine (6.05 mmol) were added and the mixture allowed to warm to room temperature. The mixture was stirred for 2 days at which time N-methylmorpholine (200 μL) was added. The mixture heated to reflux for 3 h. The methylene chloride solution was diluted with another 50 mL of methylene chloride and extracted with 10% citric acid and saturated NaHCO$_3$. The organic layer was separated, washed with saturated NaCl and dried over anhydrous MgSO$_4$. Evaporation of the methylene chloride gave an oil which was chromatographed on a silica column to give 2.4 g (80%) of a white solid. $^1$H-NMR (CDCl$_3$, 300 MHz): δ 1.17-1.31 (m, 2H), 1.47 (s, 9H), 1.75-1.80 (m, 2H), 1.83-1.98 (m, 1H), 2.69-2.78 (m, 2H), 3.74 (d, J=6.2 Hz, 2H), 4.09-4.16 (m, 2H), 6.81 (broad s, 1H), 6.87-6.89 (m, 1H), 6.90 (broad s, 1H), 7.34-7.43 (m, 2H), 7.50-7.54 (m, 2H), 8.05-8.08 (m, 1H).

d) 2-{(2-Cholorobenzenesulfonyl)-[3-[[1-(tert-butoxycarbonyl) piperidin-4-yl]methoxy]-5-[trifluoromethyl]phenyl]amino}acetic acid benzyl ester:

A solution of 2-chloro-N-{3-[(piperidin-4-yl)methoxy]-5-[trifluoromethyl]phenyl}benzenesulfonamide (300 mg, 0.55 mmol), as prepared in the preceding step, in DMF (5 mL) was treated with Cs$_2$CO$_3$ (178 mg) and α-bromoacetic acid benzyl ester (138 mg). This solution was stirred overnight at room temperature. The DMF was removed under high vacuum and the resulting residue was dissolved in ethyl acetate and extracted with 10% citric acid and saturated NaCl. The ethyl acetate solution was dried over anhydrous MgSO$_4$ and evaporated to give an oil. This oil was chromatographed on a silica column to give 313 mg (82%) of an oil. $^1$H-NMR (CDCl$_3$, 300 MHz): δ 1.15-1.40 (m, 2H), 1.48 (s, 9H), 1.68-1.78 (m, 2H), 1.83-1.93 (m, 1H), 2.69-2.77 (m, 2H), 3.68 (d, J=6.2 Hz, 2H), 4.09-4.16 (m, 2H) 4.71 (s, 2H), 5.17 (s, 2H), 6.92 (broad s, 1H), 6.98 (broad s, 1H), 7.12-7.25 (m, 1H), 7.28-7.39 (m, 6H), 7.45-7.55 (m, 2H), 7.86-7.89 (m, 1H).

e) 2-{(2-chorobenzenesulfonyl)-[3-[[1-[bis-(tert-butoxycarbonyl) aminoiminomethyl]piperidin-4-yl] methoxy]-5-[trifluoromethyl]phenyl]amino}acetic acid benzyl ester:

2-{(2-Chlorobenzenesulfonyl)-[3-[[1-(tert-butoxycarbonyl)piperidin-4-yl]methoxy]-5-[trifluoromethyl]phenyl]amino}acetic acid benzyl ester (293 mg, 0.42 mmol), as prepared in the preceding step, was dissolved in 4N HCl/dioxane and stirred for 3 h. Dioxane and excess HCl were removed under vacuum. The residue was evaporated from ether (3×) and dried under high vacuum. The resulting HCl salt was dissolved in anhydrous tetrahydrofuran and treated with bis-(tert-butoxycarbonyl)-1H-pyrazole-1-carboxamidine (130 mg, 0.42 mmol) and N,N-diisopropylethylamine (80.5 μL, 0.46 mmol). This mixture was stirred at room temperature for 2 days. The solvent was evaporated and the residue was chromatographed on a silica column to give 193 mg (55%) of product as a white solid. $^1$H-NMR (CDCl$_3$, 300 MHz): δ 1.29-1.45 (m, 2H), 1.50 (s, 18H), 1.76-1.87 (m, 2H), 1.88-2.05 (m, 1H), 2.96-3.04 (m, 2H), 3.69 (d, J=6.3 Hz, 2H), 4.09-4.25 (m, 2H), 4.72 (s, 2H), 5.17 (s, 2H), 6.94 (broad s, 1H), 6.98 (broad s, 1H), 7.11-7.12 (m, 1H), 7.28-7.40 (m, 6H), 7.45-7.55 (m, 2H), 7.87-7.90 (m, 1H).

f) 2-{(2-Chlorobenzenesulfonyl)-[3-[[1-[bis-(tert-butoxycarbonyl) aminoiminomethyl]piperidin-4-yl] methoxy]-5-[trifluoromethyl]phenyl]amino}acetic acid:

2-{(2-(Chlorobenzenesulfonyl)-[3-[[1-[(bis-tert-butoxycarbonyl)aminoiminomethyl]piperidin-4-yl] methoxy]-5-[trifluoromethyl]phenyl]amino}acetic acid benzyl ester (8 mg), as prepared in the preceding step, was dissolved in methanol (2 mL). To this solution, LiOH (2 eq in H$_2$O 2 mL) was added and the mixture stirred over night at room temperature. The reaction mixture was concentrated in vacuo and the resulting residue was partitioned between 10% citric acid and ethyl acetate. The ethyl acetate layer was separated and washed with saturated NaCl and dried over anhydrous MgSO$_4$. Evaporation of the solvent gave an oil which was purified by preparative TLC to give 4.5 mg (64%) of the title compound. $^1$H-NMR (CDCl$_3$, 300 MHz): δ 1.15-1.37 (m, 2H), 1.47 (s, 18H), 1.64=1.68 (m, 2H), 1.76-1.78 (m, 1H), 2.81-2.88 (m, 2H), 3.60 (d, J=6.2 Hz, 2H), 3.80-4.25 (m, 2H), 4.40 (s, 2H), 6.71 (broad s, 1H), 7.04 (broad s, 1H), 7.05 (broad s, 1H), 7.18-7.20 (m, 1H), 7.38 (s, 1H), 7.39 (s, 1H), 7.80 (d, J=7.8 Hz, 1H), 10.09 (broad s, 1H).

g) 2- {(2-Chlorobenzenesulfonyl)-[3-[[1-(aminoiminomethyl) piperidin-4-yl]methoxy]-5-[trifluoromethyl]phenyl]aminoacetic acid hydrochloride:

The title compound was synthesized by treating 2-{(2-chlorobenzenesulfonyl)-[3[[1-[(bis-tert-butoxycarbonyl) aminoiminomethyl]piperidin-4-yl]methoxy]-5-[trifluoromethyl]phenyl]amino}acetic acid, as prepared in the preceding step, with 4N HCl in dioxane for 5 h. Removal of solvent and evaporation from ether (3×) gave 3.3 mg (100%) of the title compound. $^1$H-NMR (CD$_3$OD, 300 MHz): δ 1.25-1.45 (m, 2H), 1.91-1.95 (m, 2H), 2.10-2.61 (m, 1H), 3.08-3.18 (m, 2H), 3.72-3.91 (m, 4H), 4.69 (s, 2H), 7.08 (s, 1H), 7.11 (s, 1H), 7.20 (s, 1H), 7.37-7.42 (m, 1H), 7.56-7.66 (m, 2H), 7.87-7.90 (m, 1H). Mass spectrum (MALDI-TOF) calcd. for C$_{22}$H$_{24}$ClF$_3$N$_4$O$_5$S: 549.1 (M+H). Found: 548.7.

The following additional compound was synthesized using a process analogous to steps (a)–(e) and (g) in Example 45:

EXAMPLE 46

6-((2-Chlorobenzenesulfonyl)-{3-[[(1-aminoiminomethyl) piperidin-4yl]methoxy]-5-methylphenyl}amino)hexanoic acid methyl ester hydrochloride:

$^1$H-NMR (300 MHz, DMSO-d$_6$) δ 1.22-1.49 (m, 8H), 1.77 (d, J=11.9 Hz, 2H), 1.98 (m, 1H), 2.19 (s, 3H), 2.25 (t,

J=7.2 Hz, 2H), 3.01 (t, J=12.2 Hz, 2H), 3.57 (s, 3H), 3.73 (m, 4H), 3.89 (d, J=13.5 Hz, 2H), 6.50 (s, 1H), 6.59 (s, 1H), 6.70 (s, 1H), 7.46 (m, 1H), 7.51 (br s, 3H), 7.69 (m, 2H), 7.79 (d, J=7.9 Hz, 1H). Mass spectrum (MALDI-TOF, sinapinic acid matrix) calcd. for $C_{27}H_{37}ClN_4O_5S$: 565.2 (M+H); Found: 565.7.

The following additional compound was synthesized using a process analogous to step (f) in Example 45:

EXAMPLE 47

6-((2-Chlorobenzenesulfonyl)-{3-||(1-aminoiminomethyl)piperidin-4-yl|methoxy]-5-methylphenyl}amino)hexanoic acid hydrochloride:

$^1$H-NMR (300 MHz, DMSO-$d_6$) δ 1.22–1.46 (m, 8H), 1.77 (d, J=11.1 Hz, 2H), 1.98 (m, 1H), 2.15 (t, J=7.3 Hz, 2H), 2.19 (s, 3H), 3.01 (t, J=12.0 Hz, 2H), 3.73 (m, 4H), 3.88 (d, J=13.2 Hz, 2H), 6.51 (s, 1H), 6.59 (s, 1H), 6.70 (s, 1H), 7.42 (br s, 3H), 7.48 (m, 1H), 7.69 (m, 2H), 7.80 (d, J=7.8 Hz, 1H). Mass spectrum (MALDI-TOF, sinapinic acid matrix) calcd. for $C_{26}H_{35}ClN_4O_5S$: 551.2 (M+H), 573.2 (M+Na); Found: 551.6, 573.3.

The following additional compound was synthesized using a process analogous to steps (a)–(g) in Example 45:

EXAMPLE 48

6-((2-Chlorobenzenesulfonyl)-{3-[[(1-aminoiminomethyl)piperidin-4-yl|methoxy]-5-(trifluoromethyl)phenyl}amino)hexanoic acid:

$^1$H-NMR (300 MHz, CDCl$_3$/TFA) δ 1.26–1.68 (m, 8H), 1.98–2.20 (m, 3H), 2.40 (t, 2H), 3.16 (t, 2H), 3.79–3.86 (m, 6H), 6.90 (s, 1H), 7.05 (d, 2H), 7.32 (t, 1H), 7.49–7.57 (m, 2H), and 7.83 (dd, 1H). Mass spectrum (MALDI-TOF, (α-cyano-4-hydroxycinnamic acid matrix) calcd. for $C_{26}H_{32}N_4O_5SF_3Cl$: 605.2 (M+H). Found: 605.1.

The following additional compound was synthesized using a process analogous to steps (a)–(e) and (g) in Example 45:

EXAMPLE 49

N-(2-Propyl)-N-{[3-(1-aminoiminomethyl)piperidin-4-ylmethoxy]-5-trifluoromethyl}phenyl-2-chlorobenzenesulfonamide hydrochloride:

$^1$H-NMR (300 MHz, DMSO-$d_6$) δ 1.09 (d, J=6.7 Hz, 6H), 1.14–1.37 (m, 2H), 1.75 (d, J=11.17 Hz, 2H), 1.95–11.99 (m, 1H), 2.92 (t, J=12.2 Hz, 2H), 3.87–3.90 (m, 4H), 4.54–4.63 (m, 1H), 6.78 (s, 1H), 6.85 (s, 1H), 7.33 (s, 1H), 7.44–7.50 (m, 1H), 7.66–7.82 (m, 3H); Mass spectrum (MALDI-TOF, sinapinic acid matrix) calcd. for $C_{23}H_{28}N_4O_3ClSF_3$, 533.2 (M+H); Found: 533.3.

EXAMPLE 50 a) 2-[N-1,3-[[1-[bis-(tert-butoxycarbonyl) aminoiminomethyl]piperidin-4-yl]methoxy]-5-[trifluoromethyl]phenyl}benzenesulfonamide]acetic acid:

2-{(2-Chlorobenzenesulfonyl)-[3-[[1-[bis-(tert-butoxycarbonyl) aminoiminomethyl]piperidin-4-yl]methoxy]-5-|trifluoromethyl]phenyl] amino}acetic acid benzyl ester (173 mg), as prepared in step e of Example 27, in MeOH containing 10% Pd/C was stirred under a hydrogen atmosphere for 1.5 h. The catalyst was removed by filtration and the solvent evaporated to give 147 mg of the product as a white solid. $^1$H-NMR (CDCl$_3$, 300 MHz): δ 1.51 (s, 18H), 1.63–1.77 (m, 2H), 1.91–1.95 (m, 2H), 2.09–2.18 (m, 1H), 3.35–3.52 (m, 2H), 3.82 (d, J=6.1 Hz, 2H), 4.07–4.11 (m, 2H), 4.39 (s, 2H), 6.81 (broad s, 1H), 6.84 (broad s, 1H), 6.97 (broad s, 1H), 7.29–7.69 (m, 5H).

b) 2-{Benzenesulfonyl-[3-[[1-(aminoiminomethyl) piperidin-4-yl]methoxy]-5-[trifluoromethyl]phenyl] amino}acetic acid hydrochloride:

2-{Benzenesulfonyl-[3-||1-|(bis-tert-butoxycarbonyl) aminoiminomethyl| piperidin-4-yl|methoxy|-5-|trifluoromethyl|phenyl|amino}acetic acid, as prepared in the preceding step, was treated with 4N HCl in dioxane for 5 h. The reaction mixture was concentrated in vacuo and the final product was crystallized from MeOH/Et$_2$O to give 50 mg (60%). $^1$H-NMR (CD$_3$OD, 300 MHz): δ 1.43–1.51 (m, 2H), 1.93–1.97 (m, 2H), 2.14–2.15 (m, 1H), 3.09–3.17 (m, 2H), 3.86–3.97 (m, 4H), 4.46 (s, 2H), 6.95 (broad s, 1H), 7.11 (s, 1H), 7.12 (s, 1H), 7.53–7.69 (m, 5H). Mass spectrum (MALDI-TOF) calcd. for $C_{22}H_{25}F_3N_4O_5S$: 515.2 (M+H). Found: 515.0.

EXAMPLE 51 a) 2-Chloro-N-1,3-||1-|bis-(tert-butoxycarbonyl) aminoiminomethyl|piperidin-4-yl|methoxy|-5-|trifluoromethyl|phenyl} benzenesulfonamide:

2-Chloro-N-{3-{[1-(tert-butoxycarbonyl)piperidin-4-yl] methoxy]-5-|trifluoromethyl|phenyl}benzenesulfonamide, prepared as in step c of Example 27, was treated in manner similar to step e of Example 27, except DMF was used instead of tetrahydrofuran as solvent, to give 100 mg (10%) of product as a white solid. $^1$H-NMR (CDCl$_3$, 300 MHz): δ 1.26–1.28 (m, 2H), 1.49 (s, 18H), 1.72–1.88 (m, 2H), 2.01–2.04 (m, 1H), 2.93-3.04 (m, 2H), 3.76 (d, J=6.3 Hz, 2H), 4.09–4.22 (m, 2H), 6.80 (broad s, 1H),6.87–6.88 (m, 1H), 6.93 (broad s, 1H), 7.36–7.48 (m, 1H), 7.50–7.53 (m, 2H), 8.06–8.09 (m, 1H).

b) 2-Chloro-N-{3-[[1-(aminoiminomethyl)piperidin4-yl] methoxy]-5-[trifluoromethyl] phenyl}benzenesulfonamidehydrochloride:

2-Chloro-N-{3-||1-[(bis-tert-butoxycarbonyl) aminoiminomethyl]piperidin-4-yl|methoxy]-5-[trifluoromethyl]phenyl}benzenesulfonamide, as prepared in the preceding step, was treated with 4N dioxane in HCl and stirred for 5 h. Dioxane and excess HCl were removed under vacuum and the resulting residue was evaporated from Et$_2$O (3×). The resulting residue was dried under high vacuum to give a white solid 35 mg (100%). $^1$H-NMR (CD$_3$OD, 300 MHz): δ 8 1.25–1.28 (m, 2H), 1.90–1.95 (m, 2H), 2.03–2.11 (m, 1H), 3.08–3.30 (m, 2H), 3.84 (d, J=6.1 Hz, 2H), 3.91–3.96 (m, 2H), 6.82 (s, 1H), 6.92 (s, 1H), 6.97 (s, 1H), 7.44–7.49 (m, 1H), 7.56 (s, 1H), 7.57 (s, 1H), 8.11 (d, J=7.4 Hz, 1H). Mass spectrum (MALDI-TOF) calcd. for $C_{20}H_2ClF_{32}N_4O_3S$: 491.1 (M+H). Found: 490.9.

EXAMPLE 52 a) N-(3-Nitrophenyl)-2-chlorobenzenesulronamide:

To 1.79 g (13.0 mmol) of 3-nitroaniline and 1.68 mL (15.3 mmol) of 4-methylmorpholine in 25 mL of anhydrous dichloromethane was added 2.50 g (11.8 mmol) of 2-chlorobenzenesulfonyl chloride. After stirring for 14 h, the mixture washed with 2N HCl (3×20 mL) and extracted with 1N NaOH (2×20 mL). The organic layer was washed with brine (25 mL), dried (Na$_2$SO$_4$) and concentrated to afford 0.62 g (22%) of the disulfonated byproduct, N-(3-nitrophenyl)-2.2'-dichlorobenzenesulfonamide. The combined NaOH extracts were acidified with 2N HCl and extracted with ethyl acetate HCl (3×20 mL). The combined ethyl acetate extracts were then washed with brine (25 mL), dried (Na$_2$SO$_4$) and concentrated to give 2.68 g (73%) of the title compound as a cream-colored solid. $^1$H-NMR (300 MHz, CDCl$_3$) δ 8.09 (m, 1H), 7.92–7.98 (m, 2H), 7.37–7.55 (m, 6H). Mass spectrum (MALDI-TOF, gentisic acid matrix) calcd. for $C_{12}H_9ClN_2O_4S$: 335.0 (M+Na), 337.0 (M+Na) ($^{37}$Cl). Found: 334.9, 336.9.

b) N-Benzyl-N-(3-nitrophenyl)-2-chlorobenzenesulfonamide:

To 1.40 g (4.48 mmol) of N-(3-nitrophenyl)-2-chlorobenzenesulfonamide in 3.0 mL of anhydrous N,N-dimethylformamide under nitrogen was added 0.929 g (6.72 mmol) of powdered anhydrous potassium carbonate and 0.586 mL (4.93 mmol) of benzyl bromide. After stirring for 1 h, the mixture was partitioned between 20 mL of ethyl acetate and 100 mL of water. The aqueous layer was extracted with 10 mL of ethyl acetate and the combined organic phases washed with water (2×50 mL), brine (50 mL) and dried ($Na_2SO_4$). Concentration afforded 1.90 g of a residue which was heated under vacuum (0.1 torr/70° C./3 h) to yield 1.78 g (99%) of title compound as a light yellow resin. $^1$H-NMR. (300 MHz, $CDCl_3$) δ 7.91–8.02 (m, 2H), 7.48–7.59 (m, 2H), 7.22–7.39 (m, 4H), 5.09 (s, 2H). Mass spectrum (MALDI-TOF, gentisic acid matrix) calcd. for $C_{19}H_{15}ClN_2O_4S$: 425.0 (M+Na), 427.0 (M+Na) ($^{37}Cl$). Found: 425.0, 427.0.

c) N-Benzyl-N-(3-aminophenyl)-2-chlorobenzenesulfonamide:

To 0.795 g (1.97 mmol) of N-benzyl-N-(3-nitrophenyl)-2-chlorobenzenesulfonamide in 10 mL of tetrahydrofuran was added 60 mg of 10% palladium on carbon. After stirring the mixture under a balloon of hydrogen for 18 h, the mixture was filtered (Diatomaceous earth) and concentrated to afford a yellow syrup. Heating the residue under vacuum (50°–60° C./2.5 h) afforded 0.727 g (99%) of the title compound as a yellow resin which crystallized on standing. $^1$H-NMR (300 MHz, $CDCl_3$) δ 7.88 (dd, 1H, J=7.9, 1.6 Hz), 7.53 (dd, 1H, J=8.0, 1.3 Hz), 7.40 (td, 1H, J=7.9, 1.6 Hz), 7.20–7.30 (m, 6H), 6.90 (t, 1H, J=8.3 Hz), 6.46 (m, 3H), 5.02 (s, 2H), 3.35 (br, 2H). Mass spectrum (MALDI-TOF, gentisic acid matrix) calcd. for $C_{19}H_{17}ClN_2O_2S$: 373.1 (M+H), 395.1 (M +Na). Found: 373.0, 395.1.

d) N-Benzyl-N-[[3-(1-tert-butoxycarbonyl)piperidin-4-yl)carbonylaminol-phenyl]-2-chlorobenzenesulfonamide:

To 479 mg (2.09 mmol) of 1-tert-butoxycarbonylisonipecotic acid, as prepared in step e of Example 1, and 924 mg (2.09 mmol) of Castro's Reagent (benzotriazolyloxytris(dimethylaminophosphonium hexafluorophosphate, BOP) in 3.0 mL of anhydrous N,N-dimethylformamide (DMF) was added 497 gL (2.85 mmol) of N,N-diisopropylethylamine and the mixture stirred under nitrogen for 10 min. A solution of 710 mg (1.90 mmol) N-benzyl-N-(3-aminophenyl)-2-chlorobenzenesulfonamide in 1.0 mL of DMF was added. After stirring for 16 h, 25 mL of saturated $NaHCO_3$ was added and the mixture poured into 45 mL of water. The mixture was extracted with ethyl acetate (2×25 mL) and the combined extracts washed with water-brine (1:1, 2×50 mL), brine (20 mL), dried ($Na_2SO_4$) and concentrated to afford 1.06 g of a brown foam. Flash chromatography on 50 g of silica eluting with 8% ethyl acetate/dichloromethane afforded 56 mg (8%) of unreacted starting aniline. Elution with 10% ethyl acetate/dichloromethane afforded 583 mg (48%) the title compound (53% based on recovered starting material) as a pale amber resin which was crystallized to a light pink solid from ether-hexane. $^1$H-NMR (300 MHz, $CDCl_3$): δ 7.86 (dd, 1H, J=8.0, 1.6 Hz), 7.55 (m, 1H), 7.46 (td, 1H, J=7.7, 1.6 Hz), 7.26 (m, 5H), 7.13 (m, 3H), 6.81 (d, 1H, J=7.8 Hz), 5.03 (s, 2H), 4.18 (br, 2H), 2.75 (br t, 2H J=11.8 Hz), 2.30 (m, 1H), 1.83 (br t, 2H, J=11.2 Hz), 1.70 (td, 2H, J=11.8,4.2 Hz), 1.47 (s, 9H),. Mass spectrum (MALDI-TOF, gentisic acid matrix) calcd. for $C_{30}H_{34}ClN_3O_5S$: 606.2 (M+Na). Found: 606.1.

e) N-Benzyl-N-[[[3-(1-tert-butoxycarbonylpiperidin-4-ylcarbonyl]-benzyloxycarbonylmethyl]amino]phenyl]-2-chlorobenzenesulfonamide:

To 200 mg (0.342 mmol) of N-benzyl-N-[[3-(1-tert-butoxycarbonylpiperidin-4-yl)carbonylamino]phenyl]-2-chlorobenzenesulfonamide in 2.0 mL of anhydrous DMF at −10° C. under nitrogen was added 15.0 mg (0.616 mmol) of dry sodium hydride. After stirring for 5 min, 59.6 μL (0.376 mmol) of benzyl bromoacetate was added. After 1 h, the mixture was warmed to room temperature. After 2.5 h, an additional 59.6 μL ( 0.376 mmol) of benzyl bromoacetate was added and the mixture stirred for 30 min. The reaction was quenched with 0.5 mL of 10% citric acid, poured into 60 mL of water and extracted with ethyl acetate (2×15 mL). The combined extracts were washed with water (2×50 mL) and brine (50 mL), dried ($Na_2SO_4$) and concentrated to 298 mg of an amber oil. Chromatography on three preparatory TLC plates (Whatman, 20×20 cm, 1000 μM thickness) developed with 4% methanol-dichloromethane afforded 126 mg (50%) of the title compound as a pale yellow resin along with 66 mg (33%) of recovered starting secondary amide. Yield based on recovered starting material was 75%. $^1$H-NMR (300 MHz, $CDCl_3$): δ 7.91 (dd, 1H, J=8.0, 1.6 Hz), 7.44–7.54 (m, 2H), 7.09–7.40 (m, 15H), 5.15 (s, 2H), 4.96 (s, 2H), 4.15 (s, 2H), 3.94 (br, 2H), 2.33 (br, 2H), 2.15 (m, 1H), 1.44 (s, 9H), 1.35–1.65 (m, 4H). Mass spectrum (MALDI-TOF, gentisic acid matrix) calcd. for $C_{39}H_{42}ClN_3O_7S$: 754.2 (M+Na). Found: 754.3.

f) N-Benzyl-N-[[[3-(1-tert-butoxycarbonyl)piperidin-4-ylmethyl]benzyloxycarbonylmethyl]amino]phenyl]2-chlorobenzenesulfonamide:

To 0.386 mL (0.771 mmol) of 2M lithium borohydride in tetrahydrofuran was added 1.0 mL of tetrahydrofuran followed by 0.195 mL (1.54 mmol) of chlorotrimethylsilane. After stirring for 5 min, 188 mg (0.257 mmol) of N-benzyl-N-[[[3-(1 -tert-butoxycarbonyl)piperidin-4-ylcarbonyl]benzyloxycarbonylmethyl]amino]phenyl]-2-chlorobenzenesulfonamide in 2.0 mL of tetrahydrofuran was added, the mixture heated at 50° C. under nitrogen for 3 h, cooled to room temperature over 1 h and let stand for 10 h. After quenching the reaction with 0.2 mL of MeOH, 1.0 mL of saturated $NaHCO_3$ was added, the mixture stirred for 2 min and then 2 mL of 1M pH 7 buffer was added. The mixture was extracted with ethyl acetate (2×10 mL) and the combined extracts were washed with brine (10 mL), dried ($Na_2SO_4$) and concentrated to 190 mg of colorless resin. Chromatography on a Waters Associates 10 g silica Sep-Pak SPE column eluting with 4% ethyl acetate-dichloromethane afforded 78.6 mg (42%) of the title compound as a colorless resin. $^1$H-NMR (300 MHz, $CDCl_3$) δ 7.86 (dd, 1H, J=7.9, 1.6 Hz), 7.52 (dd, 1H, J=7.9, 1.3 Hz), 7.43 (td, 1H, J=7.7, 1.6 Hz), 7.19-7.38 (m, 11H), 6.93 (t, 1H, J=8.0 Hz), 6.30–6.40 (m, 3H), 5.00 (s, 2H), 4.71 (d, 2H, J=3.2 Hz), 4.09 (br, 2H), 3.87 (s, 2H), 3.03 (d, 2H, J=6.8 Hz), 2.56 (br t, 2H, J=12.2 Hz), 1.60 (m, 3H), 1.47 (s, 9H), 0.90–1.21 (m, 2H). Mass spectrum (MALDI-TOF, gentisic acid matrix) calcd. for $C_{39}H_{44}ClN_3O_6S$: 740.3 (M+Na). Found: 741.0.

g) N-Benzyl-N-[[3-(1-aminoiminomethyl)piperidin-4-ylmethyl]benzyloxycarbonylmethyl]-amino]phenyl]-2-chlorobenzenesulfonamide:

To 70.0 mg (0.195 mmol) of N-benzyl-N-[3-(1-tert-butoxycarbonyl)piperidin-4-ylmethyl]benzyloxycarbonylmethyl]amino]phenyl]-2-chlorobenzenesulfonamide in 1.5 mL of anhydrous dichloromethane was added 0.50 mL of trifluoroacetic acid. After stirring for 20 min, the solution was concentrated and placed under vacuum (0.1 torr/1 h) to afford 70 mg of a colorless resin. Mass spectrum (MALDI-TOF, gentisic acid matrix) calcd. for $C_{34}H_{36}ClN_3O_4S$: 618.2 (M+H). Found: 618.2. To 61 mg of this residue in 2.0 mL of anhydrous methanol was added 48.7 mg (0.332 mmol) aminoiminomethanesulfonic acid and 136 gL (0.780 mmol) of N,N- diisopropylethylamine and the mixture stirred for 1.25 h. 2 mL of saturated NaHCO$_3$ and 2 mL of water were added and the mixture stirred for 10 min. After concentration to dryness, the residue was partitioned between 10 mL of water and 10 mL of dichloromethane. The aqueous phase was extracted with dichloromethane (4×5 mL) and the combined organic phases dried (Na$_2$SO$_4$) and concentrated to afford 60.1 mg (93%) of the title compound as a colorless glass. $^1$H-NMR (300 MHz, CDCl$_3$) δ 7.84 (dd, 1H, J=8.0, 1.6 Hz), 7.51 (dd, 1H, J=8.0, 1.3 Hz), 7.43 (td, 1H, J=7.7, 1.6 Hz), 7.20–7.38 (m, 11H), 6.93 (t, 1H, J=8.1 Hz), 6.34 (m, 3H), 5.10 (s, 2H), 4.95 (s, 2H), 3.88 (obscured br d, 2H), 3.86 (s, 2H), 3.02 (d, 2H, J=6.3 Hz), 2.84 (t, 2H, J=12.9 Hz), 1.70 (m, 3H), 1.13 (m, 2H). Mass spectrum (MALDI-TOF, gentisic acid matrix) calcd. for C$_{34}$H$_{36}$ClN$_3$O$_4$S: 660.2 (M+H). Found: 660.0.

h) N-Benzyl-N-||3-(1-aminoiminomethyl)piperidin-4-ylmethyl|carboxymethyl|amino|phenyl|-2-chlorobenzenesulfonamide:

To 54.2 mg (82.1 μmol) of N-benzyl-N-||3-(1-aminoiminomethyl)piperidin-4-ylmethyl|benzyloxycarbonylmethyl|amino|phenyl|-2-chlorobenzenesulfonamide in 2 mL of tetrahydrofuran:methanol (1:1) was added 410 μL of 1M aqueous lithium hydroxide. After stirring for 30 min, the mixture was concentrated to near dryness. The residue was dissolved in 8 mL of water, acidified with 1M HCl and extracted with ethyl acetate (5×8 mL). The combined extracts were dried (Na$_2$SO$_4$) and concentrated to a white residue. Trituration with ether and concentration afforded 41.4 mg (83%) of the title compound as a white solid. $^1$H-NMR (300 MHz, CD$_3$OD) δ 7.85 (dd, 1H, J=7.9, 1.5 Hz), 7.65 (dd, 1H, J=8.0, 1.1 Hz), 7.56 (td, 1H, J=7.7, 1.5 Hz), 7.24–7.38 (m, 6H), 6.95 (t, 1H, J=8.1 Hz), 6.44 (d, 2H, J=9.6 Hz), 6.36 (m, 2H), 3.92 (s, 2H), 3.87 (d, 2H, J=13.8 Hz), 3.11 (d, 2H, J=7.0 Hz), 2.98 (t, 2H, J=12.1 Hz), 1.86 (m, 1H), 1.76 (d, 2H, J=13.3 Hz), 1.90 (m, 2H). Mass spectrum (MALDI-TOF, gentisic acid matrix) calcd. for C$_{28}$H$_{32}$ClN$_5$O$_4$S: 570.2 (M+H). Found: 570.0.

EXAMPLE 53 a) 2-Chlorobenzenesulfonic acid 3-[[1[-(N-methoxycarbonylaminoiminomethyl)piperidin-4-yl]methoxyl]-5-methylphenyl ester:

A suspension of 2-chlorobenzenesulfonic acid 3-[[1-(aminoiminomethyl)piperidin-4-yl]methoxy]-5-methylphenyl ester (0.3 g, 0.63 mmol), as prepared in the step f of the Example 3, in acetonitrile (10 mL) was treated with diisopropyl ethylamine (0.11 mL, 0.63 mmol) followed by dimethyl pyrocarbonate (0.067 mL, 0.63 mmol) and stirred it ambient temperature for 41 h. The reaction mixture was evaporated to dryness and the residue was partitioned between methylene chloride and water. The organic layer was separated and washed with water. The aqueous layers were combined and extracted with methylene chloride. The organic layers were combined, washed with brine, dried, and evaporated to dryness. The residue was applied to a 10 g SepPak silica-gel column and eluted with methylene chloride, followed by 10%, then 20% ethyl acetate in methylene chloride. The appropriate fractions were combined and evaporated to dryness. The residue was treated with hexane overnight. The solid was collected by filtration, washed with ether, and dried under high vacuum to give the title compound as a white solid (0.188 g, 61%). $^1$H-NMR (300 MHz, CDCl$_3$) δ 1.33 (dq, 2H), 1.87 (br d, 2H), 2.00 (m, 1H), 2.24 (s, 3H), 2.89 (dt, 2H), 3.69 (m, 5H), 4.25 (br d, 2H), 6.49 (br t, 1H), 6.52 (br s, 1H), 6.58 (br s, 1H), 7.39 (dt, 1H), 7.56-7.65 (m, 2H), and 7.97 (m, 1H). Mass spectrum (MALDI-TOF, α-cyano-4-hydroxycinnamic acid matrix) calcd. for C$_{22}$H$_{26}$N$_3$O$_6$SCl: 496.1 (M+H). Found: 495.9.

EXAMPLE 54 a) N-carboxymethyl-1H-pyrazole-1-carboxamidine:

A solution of commercially available 1H-pyrazole-1-carboxamidine hydrochloride (2.92 g, 0.02 mol) in anhydrous N,N-dimethylformamide (20 mL) and methylene chloride (20 mL) was treated with N,N-diisopropylethylamine (3.5 mL, 0.02 mol) followed by dimethyl pyrocarbonate (2.14 mL, 0.02 mol). The reaction mixture was stirred at ambient temperature for 3 h, then evaporated to dryness. The residue was applied to a 10 g SepPak silica-gel column and eluted with methylene chloride. The appropriate fractions were combined and evaporated. The residue was applied to another 10 g SepPak silica-gel column and eluted with methylene chloride. The appropriate fractions were combined and evaporated. The residue was dissolved in methylene chloride and washed with water. The organic layer was separated, dried, and evaporated to give the title compound as a white solid (2.83 g, 84%). $^1$H-NMR (300 MHz, CDCl$_3$) δ 3.81 (s., 3H), 6.44 (dd, 1H), 7.64 (br m, 1H), 7.71 (dd, 1H), 8.44 (dd, 1H), and 9.04 (br m, 1H).

b) N,N'-bis-carboxymethyl-1H-pyrazole-1-carboxamidine:

A suspension of sodium hydride (0.85 g, 0.035 mol) in anhydrous tetrahydrofuran (30 mL) was cooled in an ice-water bath and treated with a solution of N-carboxymethyl-1H-pyrazole-1-carboxamidine (2.83 g, 0.017 mol), as prepared in the preceding step, in anhydrous tetrahydrofuran (15 mL) via a cannula. After stirring for 0.5 h, dimethyl pyrocarbonate (1.8 mL, 0.017 mol) was added to the reaction mixture via syringe. The reaction mixture was allowed to warm to room temperature. The reaction was quenched with water and treated with 1N HCl until pH 7.0. The mixture was extracted with ethyl acetate (three times). The aqueous layer was treated with saturated sodium chloride solution and re-extracted with ethyl acetate. The organic extracts were combined, washed with brine, dried, and evaporated to dryness. The residue was recrystallized from hexane, collected by filtration, washed with hexane, and dried under high vacuum to give a mixture consisting of two bis-carboxymethylated materials in a ratio of (31%) A and (69%) B. $^1$H-NMR (300 MHz, CDCl$_3$) of A: δ 3.80 (s, 6H), 6.44 (m, 1H), 7.71 (m, 1H), 8.44 (dd, 1H), and 9.04 (br m, 1H). $^1$H-NMR (300 MHz, CDCl$_3$) of B: δ 3.85 (s, 3H), 3.87 (s, 3H), 6.47 (m, 1H), 7.66 (m, 1H), 8.30 (dd, 1H), and 9.29 (br m, 1H).

c) 2-Chlorobenzenesulfonic acid 3-[[1-((N-methoxycarbonylamino)-N-methoxycarbonyliminomethyl)piperidin-4-yl]methoxy]-5-methylphenyl ester:

A solution of 2-chlorobenzenesulfonic acid 3-[(piperidin-4-yl)-methoxy]-5-methylphenyl ester (0.25 g, 0.5 mmol), as prepared in the step e of the Example 3, and triethylamine (0.077 mL, 0.55 mmol) in anhydrous tetrahydrofuran (10 mL) was treated with N,N'-bis-carboxymethyl-1H-pyrazole-1-carboxamidine (0.18 g, 0.55 mmol), as prepared in the preceding step, at ambient temperature. The reaction mixture was evaporated to dryness and the residue was partitioned between methylene chloride and water. The organic layer was separated and washed with water. The aqueous layers were combined and extracted with methylene chloride. The organic layers were combined, washed with brine, dried, and evaporated to dryness. The residue was applied to a 10 g SepPak silica-gel column and eluted with methylene chloride, followed by 10% ethyl acetate in methylene chloride. The appropriate fractions were combined and evaporated to dryness. The residue was treated with hexane and sonicated. The resulting solid was collected by filtration, washed with ether, and dried under high vacuum to give the title compound as a white solid (0.189 g, 68%). $^1$H-NMR (300 MHz, CDCl$_3$/TFA) δ 1.25–1.31 (m, 1H), 1.69–1.80 (m, 2H), 2.03–2.31 (m, 5H), 3.48 (t, 2H), 3.76 (d, 2H), 3.88 (s, 6H), 4.03 (br d, 2H), 6.50 (s, 1H), 6.54 (s, 1H), 6.59 (s, 1H), 7.37 (br t, 1H), 7.57–7.65 (m, 2H), and 7.95 (d, 1H). Mass spectrum (MALDI-TOF, α-cyano-4-hydroxycinnamic acid matrix) calcd. for C$_{24}$H$_{28}$N$_3$O$_8$SCl: 554.3 (M+H) and 576.3 (M+Na). Found: 554.3 and 576.3.

EXAMPLE 55

2-Chlorobenzenesulfonic acid 3-|[1-((N,N-di(methyloxycarbonyl) amino)-N-methoxycarbonyliminomethyl)piperidin-4-yl]methoxy|-5-methylphenylester:

A suspension of 2-chlorobenzenesulfonic acid 3-|[1-(aminoiminomethyl)piperidin-4-yl]methoxy]-5-methylphenyl ester (0.2 g, 0.45 mmol), as prepared in the step (f) of Example 3, in acetonitrile (10 mL) was treated with N,N-diisopropylethylamine (0.08 mL, 0.45 mmol) followed by excess dimethyl pyrocarbonate. The reaction mixture was stirred at ambient temperature for 2 h. The reaction mixture was evaporated to dryness. The residue was applied to a 10 g SepPak silica-gel column and eluted with 5%, then 10% ethyl acetate in methylene chloride. The appropriate fractions were combined and evaporated to dryness. The residue was recrystallized from ethanol and water. The solid was collected by filtration and dried under high vacuum to give the title compound as a white foam (0.190 g, 69%). $^1$H-NMR (300 MHz, CDCl$_3$) δ 1.25–1.55 (m, 2H), 1.90 (br d, 2H), 2.04 (m, 1H), 2.23 (s, 3H), 3.03 (m, 2H), 3.70–3.75 (m, 5H), 3.85-3.94 (m, 7H), 4.82 (br d, 1H), 6.51 (br t, 1H), 6.53 (br s, 1H), 6.57 (br s, 1H), 7.39 (m, 1H), 7.56–7.65 (m, 2H), and 7.97 (dd, 1H). Mass spectrum (MALDI-TOF, α-cyano-4-hydroxycinnamic acid matrix) calcd. for C$_{26}$H$_{30}$N$_3$O$_{10}$SCl: 612.4 (M+H). Found: 612.5.

EXAMPLE 56 a) 2-Chlorobenzenesulfonic acid 3-formylphenyl ester.:

To a solution of 2.0 (16.4 mmol) of 3-hydroxybenzaldehycLe in methylene chloride (10 mL) containing 10 mL (78.5 mmol) of N,N-diisopropylethylamine was added 3.45 g (16.3 mmol) of 2-chlorobenzenesulfonyl chloride. After stirring at ambient temperature for 1 h, the reaction mixture was quenched with 3N HCl (acidic to pH paper) and extracted into diethyl ether. The organic phase was washed with 3N HCl and then saturated sodium bicarbonate. Drying (MgSO$_4$) and purification by flash chromatography (methylene chloride/ petroleum ether 4:1) gave 4.28 g of the title compound as a colorless solid. $^1$H-NMR (300 MHz, CDCl$_3$) δ 9.94 (s, 1H), 7.96 (d, 1H), 7.94 (d, 1H), and 7.36–7.8 (m, 6H). Mass spectrum (MALDI-TOF; gentisic acid matrix) calcd. for C$_{13}$H$_9$ClO$_4$S: 319.0 (M+Na). Found: 319.0.

b) 3-(tert-Butyloxycarbonyl)aminopropionaldehyde:

A mixture of 2.0 g (11.6 mmol) of 3-N-(tert-butyloxycarbonyl)propanol and 4.45 g (21 mmol) of pyridinium chlorochromate in methylene chloride (30 mL) was stirred at ambient temperature for 30 min. Another 3 g of pyridinium chlorochromate was added and the reaction mixture further stirred for 30 min. The mixture was filtered through a thick pack of silica gel (diethyl ether/methylene chloride (1:9) elution) and concentrated. The crude product (1.2 g) was used as is: $^1$H-NMR (300 MHz, CDCl$_3$) δ 9.8 (1H), 4.91 (bs, 1H), 3.42 (q, 2H), 2.71 (t, 2H), and 1.43 (s, 9H).

c) 2-Chlorobenzenesulfonic acid 3-N-methylaminomethylphenyl ester:

A mixture of 500 mg (1.73 mmol) of 2-chlorobenzenesulfonic acid 3-formylphenyl ester, as prepared in step a of this Example, and 800 mg (11.9 mmol) of methylamine hydrochloride in methylene chloride/methanol (10: 1; 11 mL) was treated with 800 mg (3 mmol) of tetramethylammonium triacetoxyborohydride. The reaction mixture was stirred for 1 h, quenched with saturated sodium bicarbonate until foaming ceased, and extracted into diethyl ether. The organic phase was washed with saturated sodium bicarbonate solution, (3×20 mL), dried (K$_2$CO$_3$), and concentrated to give 508 mg of crude product (94% yield) which was used without further purification: Mass spectrum (MALDI-TOF; α-cyano-4-hydroxycinnamic acid matrix) calcd. for C$_{14}$H$_{14}$ClNO$_3$S: 312.1 (M+H). Found: 312.1.

d) 2-Chlorobenzenesulfonic 7 acid 3-||(N-3-tert-butoxycarbonylamino)propyl|-N-methylamino| methylphenyl ester:

To a solution of 190 mg (0.610 mmol) of 2-chlorobenzenesulfonic acid 3-N-methylaminomethylphenyl ester, as prepared in the preceding step, and 168 mg (0.97 mmol) of 3-(tert-butyloxycarbonyl)aminopropionaldehyde, as prepared in step b of this Example, in 10 mL of methylene chloride/1 mL methanol was added 400 mg (1.5 mmol) of tetramethylammonium triacetoxyborohydride. After stirring for 30 min, another 90 mg of the aldehyde was added. The reaction mixture was stirred for 30 min, quenched with saturated sodium bicarbonate solution and extracted into diethyl ether (70 mL). The organic extract was washed with 4×20 mL of sodium bicarbonate, dried (MgSO$_4$), and purified by flash chromatography (methylene chloride/diethyl ether (1:1) to methylene chloride/diethyl ether/methanol (40:50:10) to give 158 mg of the title compound as an oil: $^1$H-NMR (300 MHz, CDCl$_3$) δ 7.92 (dd, 1H), 7.54-7.64 (m, 2H), 7.36 (dt, 1H), 6.9–7.21 (m, 4H), 3.41 (s, 2H), 3.14 (q, 2H), 2.36 (t, 2H), and 1.47 (s, 9H).

e) 2-Chlorobenzenesulfonic acid 3-|(N-3-aminopropyl)-N-methylamino]methylphenyl ester dihydrochloride:

A solution of 156 mg of 2-chlorobenzenesulfonic acid 3-[[(N-3-tert-butoxycarbonylamino)propyl]-N-methylamino]methylphenyl ester, as prepared in the preceding step, in methylene chloride (1 mL) was treated with 1 mL of 4N HCl in dioxane. The reaction mixture was stirred for 30 min, and concentrated from diethyl ether/hexane to give 160 mg of the title compound as a solid: (MALDI-TOF; gentisic acid matrix) calcd. for C$_{17}$H$_{21}$ClN$_2$O$_3$S: 369.1 (M+H). Found: 369.0.

j) 2-Chlorobenzenesulfonic acid 3-[N-[[3-(aminoiminomethyl)amino|propyl]-N-(methyl)aminomethyl]phenylesteracetic acid salt:

A mixture of 66 mg (0.179 mmol) of 2-chlorobenzenesulfonic acid 3[(N-3-aminopropyloxy)-N-methylamino]methylphenyl ester dihydrochloride, as prepared in the preceding step, was treated with 66 mg (0.532 mmol) of aminoiminosulfuric acid, and 425 μL (2.44 mmol) of diisopropylethylamine in 1 mL of N,N-dimethylformamide. The reaction mixture was stirred overnight concentrated, and treated with 3 mL of 2N sodium hydroxide. The reaction mixture was diluted with water, extracted into methylene chloride, dried (K$_2$CO$_3$), and concentrated. The residue was treated with 200 μL of acetic acid and passed through a Sep-Pak silica gel column (10 g) using elutions of methylene chloride/methanol/acetic acid (57.3:39.7:3) to give 27 mg of the title compound as a gum: $^1$H-NMR (300 MHz, DMSO-d$_6$) δ 8.8 (br s, 1H), 7.77–7.90

(m, 7H), 7.56 (dt, 1H), 7.34 (t, 1H), 7.22 (d, 1H), 6.98–7.03 (m, 1H), 2.28 (t, 2H), 1.91 (s, 3H), 1.76 (s, 3H), and 1.59 (pentet, 2H). Mass spectrum (MALDI-TOF; α-cyano-4-hydroxycinnamic acid matrix) calcd. for $C_{18}H_{23}ClN_4O_3S$: 411.1 (M+H). Found: 411.1.

EXAMPLE 57
In Vitro Inhibition of Purified Enzymes Reagents:

All buffer salts were obtained from Sigma Chemical Company (St. Louis, MO), and were of the highest purity available. The enzyme substrates, N-benzoyl-Phe-Val-Arg-p-nitroanilide (Sigma B7632), N-benzoyl-Ile-Glu-Gly-Arg-p-nitroanilide (Sigma B2291), N-p-tosyl-Gly-Pro-Lys-p-nitroanilide (Sigma T6140), and N-succinyl-Ala-Ala-Pro-Phe-p-nitroanilide (Sigma S7388) were all obtained from Sigma.

Human α-thrombin, human factor Xa, and human plasmin were obtained from Enzyme Research Laboratories (South Bend, Ind.). Bovine α-chymotrypsin and bovine trypsin were obtained from Sigma.

$K_i$ Determinations: All assays are based on the ability of the test compound to inhibit the enzyme-catalyzed hydrolysis of a peptide p-nitroanilide substrate. In a typical $K_i$ determination, substrate is prepared in DMSO, and diluted into an assay buffer consisting of 50 mM HEPES, 200 mM NaCl, pH 7.5. The final concentration for each of the substrates is listed below. In general, substrate concentrations are lower than the experimentally determined value for $K_m$. Test compounds are prepared as a 0.16 mg/mL solution in DMSO. Dilutions are prepared in DMSO yielding 8 final concentrations encompassing a 200-fold concentration range. Enzyme solutions are prepared at the concentrations listed below in assay buffer.

In a typical $K_i$ determination, into each well of a 96 well plate is pipetted 280 µL of substrate solution, 10 µL of inhibitor solution, and the plate allowed to thermally equilibrate at 37° C. in a Molecular Devices plate reader for >10 minutes. Reactions were initiated by the addition of a 20 µL aliquot of enzyme, and the absorbance increase at 405 nM is recorded for 15 minutes. Data corresponding to less than 10% of the total substrate hydrolysis were used in the calculations. The ratio of the velocity (rate of the change in absorbance as a function of time) for a sample containing no inhibitor is divided by the velocity of a sample containing inhibitor, and is plotted as a function of inhibitor concentration. The data are fit to a linear regression, and the value of the slope of the line calculated. The inverse of the slope is the experimentally determined $K_i$ value.

Thrombin: Thrombin activity was assessed as the ability to hydrolyze the substrate Suc-Ala-Ala-Pro-Arg-pNA. Substrate solutions were prepared at a concentration of 20 µM (20 µM<<$K_m$=180 µM) in assay buffer. Final DMSO concentration was 0.3%. Purified human α-thrombin was diluted into assay buffer to a concentration of 450 nM. Final reagent concentrations were: |thrombin|=0.5 nM, |Suc-Ala-Ala-Pro-Arg-pNA|=20 µM.

Factor Xa: Factor Xa activity was assessed as the ability to hydrolyze the substrate Bz-Ile-Glu-Gly-Arg-pNA. Substrate solutions were prepared at a concentration of 51 µM (51 µM<<$K_m$=1.3 mM) in assay buffer. Final DMSO concentration was 0.3%. Purified activated human Factor Xa was diluted into assay buffer to a concentration of 300 nM. Final reagent concentrations were: |FXa|=20 nM, |Bz-Ile-Glu-Gly-Arg-pNA|=51 µM.

Plasmin: Plasmin activity was assessed as the ability to hydrolyze the substrate Tos-Gly-Pro-Lys-pNA. Substrate solutions were prepared at a concentration of 22 µM (22 µM<<$K_m$=240 µM) in assay buffer. Final DMSO concentration was 0.3%. Purified human plasmin was diluted into assay buffer to a concentration of 225 nM. Final reagent concentrations were: |plasmin|=15 nM, |Tos-Gly-Pro-Lys-pNA|=22 µM.

Chymotrypsin: Chymotrypsin activity was assessed as the ability to hydrolyze the substrate Suc-Ala-Ala-Pro-Phe-pNA. Substrate solutions were prepared at a concentration of 14 µM (14 µM<<$K_m$=61 uM) in assay buffer. Final DMSO concentration was 0.3%. Purified bovine α-chymotrypsin was diluted into assay buffer to a concentration of 45 nM. Final reagent concentrations were: |chymotrypsin|=3 nM, |Suc-Ala-Ala-Pro-Phe-pNA|=14 µM.

Trypsin: Trypsin activity was assessed as the ability to hydrolyze the substrate Bz-Phe-Val-Arg-pNA. Substrate solutions were prepared at a concentration of 14 µM (14 µM<<$K_m$=291 µM) in assay buffer. Final DMSO concentration was 0.3%. Purified bovine trypsin was diluted into assay buffer to a concentration of 150 nM. Final reagent concentrations were: |Trypsin|=10 nM, |Bz-Phe-Val-Arg-pNA|=14 µM.

The results obtained employing synthesized compounds are given in Table 1.

TABLE 1

| Product of Example Number | Enzyme | $K_i$ (µM) |
|---|---|---|
| 1 | Thrombin | 0.25 |
| 3 | Thrombin | 0.008 |
| 4 | Factor Xa | 58.1 |
| 5 | Plasmin | 29.2 |
| 6 | Thrombin | 0.33 |
| 11 | Trypsin | 5.3 |
| 12 | Chymotrypsin | 12.6 |
| 14 | Thrombin | 0.026 |
| 17 | Thrombin | 0.036 |
| 24 | Thrombin | 0.040 |
| 33 | Thrombin | 0.034 |
| 38 | Thrombin | 0.019 |
| 42 | Thrombin | 0.021 |
| 44 | Thrombin | 6.9 |

The results indicate that the compounds of the present invention are potent inhibitors of proteases. Compounds of the present invention inhibit a number of proteases, such as chymotrypsin, plasmin, factor Xa, thrombin and trypsin.

Having now fully described this invention, it will be understood to those of ordinary skill in the art that the same can be performed within a wide and equivalent range of conditions, formulations, and other parameters without affecting the scope of the invention or any embodiment thereof. All patents and publications cited herein are fully incorporated by reference herein in their entirety.

What is claimed is:

1. A compound having the Formula I:

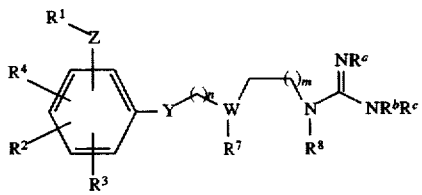

or a solvate, a hydrate or a pharmaceutically acceptable salt thereof; wherein:

$R^1$ is one of $C_{6-12}$alkyl, cycloalkyl, alkenyl, alkynyl, aryl, aralkyl or heteroaryl, any of which may be optionally substituted;

Z is one of —NR$^{10}$SO$_2$—, —SO$_2$NR$^{10}$—, —NR$^{10}$C(R$^y$R$^z$)—, —C(R$^y$R$^z$)NR$^{10}$—, —OSO$_2$—, —SO$_2$O, —OC(R$^y$R$^z$)—, —C(R$^y$R$^z$)O—, —NR$^{10}$CO— or —CONR$^{10}$—, where R$^y$ and R$^z$ are each independently one of hydrogen, alkyl, cycloalkyl, aryl, aralkyl, hydroxyalkyl, carboxylalkyl, aminoalkyl, monoalkylaminoalkyl, dialkylaminoalkyl or carboxy; and R$^{10}$ is defined below;

R$^2$, R$^3$ and R$^4$ are each independently one of hydrogen, alkyl, cycloalkyl, alkenyl, alkynyl, aryl, aralkyl, heteroaryl, trifluoromethyl, halogen, hydroxyalkyl, cyano, nitro, carboxamido, —CO$_2$R$^x$, —CH$_2$OR$^x$ or —OR$^x$, or when present on adjacent carbon atoms R$^2$ and R$^3$ may also be taken together to form one of —CH=CH—CH=CH— or —(CH$_2$)$_q$—, where q is from 2 to 6, and R$^4$ is defined as above;

R$^x$, in each instance, is independently one of hydrogen, alkyl or cycloalkyl wherein said alkyl or cycloalkyl groups may optionally have one or more unsaturations;

Y is one of —O—, —NR$^5$—, —S—, —CR$^5$R$^9$— or a covalent bond;

W is N or CR$^{10}$;

R$^7$ and R$^8$ are each independently one of hydrogen, alkyl, aralkyl, aryl, hydroxyalkyl or carboxylalkyl, or R$^7$ and R$^8$ are taken together to form —(CH$_2$)$_y$—, where y is zero, 1 or 2, with the proviso that when W is N, y cannot be zero or 1;

R$^5$, in each instance, is independently one of hydrogen, alkyl, aralkyl, aryl, hydroxyalkyl, aminoalkyl, monoalkylaminoalkyl, dialkylaminoalkyl or carboxylalkyl;

R$^9$ is one of alkyl, aralkyl, aryl, hydroxyalkyl or carboxylalkyl;

R$^{10}$ is hydrogen, aryl, aralkyl, alkyl, alkyloxyalkyl, wherein said alkyl or alkyloxyalkyl may be substituted by a single amino, monoalkylamino, dialkylamino, carboxy, or by one or more hydroxy groups, wherein the hydroxy groups can be further substituted by alkyl, hydroxyalkyl, alkyloxyalkyl, hydroxyalkyloxyalkyl or alkylcarbonyl groups and wherein two vicinal hydroxy groups can each be linked by an alkylidene group; or R$^{10}$ can form the group —E—P(O)R$^{11}$R$^{12}$, where E is alkylene, preferably having one to 4 carbon atoms; and R$^{11}$ and R$^{12}$ are independently C$_{1-6}$alkyl groups;

R$^a$, R$^b$ and R$^c$ are independently hydrogen, alkyl, hydroxy, alkoxy, aryloxy, aryloxy, alkoxycarbonyloxy, cyano or —CO$_2$R$^w$, where R$^w$ is alkyl, cycloalkyl, phenyl, benzyl,

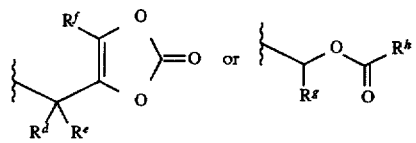

where R$^d$ and R$^e$ are independently hydrogen, C$_{1-6}$ alkyl, C$_{2-6}$ alkenyl or phenyl, R$^f$ is hydrogen, C$_{1-6}$ alkyl, C$_{2-6}$ alkenyl or phenyl, R$^g$ is hydrogen, C$_{1-6}$ alkyl, C$_{2-6}$ alkenyl or phenyl, and R$^h$ is aralkyl or C$_{1-6}$ alkyl;

n is from zero to 8, with the proviso that when W is N and Y is other than —CR$^9$R$^{10}$—, then n is from 2 to 8; and m is from zero to 4, provided that when (a) W is N, or (b) W is CR$^{10}$, R$^7$ and R$^8$ together form —(CH$_2$)$_y$— and y is 2, then m is not zero.

2. A compound of claim 1, wherein

R$^1$ is one of C$_{6-12}$alkyl, cycloalkyl, aryl, aralkyl or heteroaryl, any of which may be optionally substituted by one or more of hydroxy, nitro, trifluoromethyl, halogen, alkoxy, cyano, amino, monoalkylamino, dialkylamino, carboxyalkoxy, mono(carboxylalkyl) amino, di(carboxylalkyl)amino, amidino, guanidino, ditrifluoromethoxy or perfluoroethoxy, and wherein said aryl, cycloalkyl and aralkyl may further be optionally substituted by one or more alkyl moieties;

Z is one of —NR$^{10}$SO$_2$—, —SO$_2$NR$^{10}$—, —NR$^{10}$CH$_2$—, —CH$_2$NR$^{10}$—, —OSO$_2$—, —SO$_2$O—, —OCH$_2$— or —CH$_2$O—;

R$^2$, R$^3$ and R$^4$ are each independently one of hydrogen, alkyl, cycloalkyl, aryl, aralkyl, heteroaryl, trifluoromethyl, halogen, hydroxyalkyl, cyano, nitro, carboxamide, —CO$_2$R$^x$, —CH$_2$OR$^x$ or —ORx, or when present on adjacent carbon atoms, R$^2$ and R$^3$ may also be taken together to form one of —CH=CH—CH=CH— or —(CH$_2$)$_q$—, where q is from 2 to 6, and R$^4$ is defined as above;

R$^x$, in each instance, is independently one of hydrogen, alkyl or cycloalkyl wherein said alkyl or cycloalkyl groups may optionally have one or more unsaturations;

Y is one of —O—, —NR$^{10}$—, —S—, —CR$^5$R$^9$— or a covalent bond;

W is N or CR$^{10}$;

R$^a$, R$^b$ and R$^c$ are independently one of hydrogen, alkyl, cyano or —CO$_2$R$^y$, where R$^y$ is alkyl or cycloalkyl;

R$^7$ and R$^8$ are each independently one of hydrogen, alkyl, aralkyl, aryl, C$_{2-10}$hydroxyalkyl or carboxylalkyl, or R$^7$ and R$^8$ are taken together to form —(CH$_2$)$_y$—, where y is zero, 1 or 2, with the proviso that when W is N, y cannot be zero or 1;

R$^9$ is one of alkyl, aralkyl, aryl, hydroxyalkyl or carboxylalkyl;

R$^5$ and R$^{10}$, in each-instance, are independently one of hydrogen, alkyl, aralkyl, aryl, C$_{2-10}$hydroxyalkyl or carboxylalkyl;

n is from zero to 8, with the proviso that when W is N and Y is other than —CR$^9$R$^{10}$—, then n is from 2 to 8; and m is from zero to 4, provided that when (a) W is N, or (b)W is CR$^{10}$, R$^7$ and R$^8$ together form —(CH$_2$)$_y$— and y is 2, then m is not zero.

3. A compound of claim 1, wherein Z is —SO$_2$NR$^{10}$—, —SO$_2$O— or —CH$_{2l\ O}$—.

4. A compound of claim 1, wherein R$^1$ is one of C$_{4-7}$cycloalkyl or C$_{6-12}$aryl, either of which is optionally substituted by one or more of hydroxy, nitro, trifluoromethyl, halogen, C$_{1-6}$alkoxy, C$_{1-6}$alkyl, amino, mono(C$_{1-6}$)alkylamino, di(C$_{1-6}$)alkylamino, cyano, amidino, guanidino, carboxyalkoxy, trifluoromethoxy or perfluoroethoxy.

5. A compound of claim 1, wherein R$^1$ is heteroaryl, optionally substituted by one or more of hydroxy, nitro, trifluoromethyl, halogen, C$_{1-6}$alkoxy, C$_{1-6}$alkyl, amino, mono(C$_{1-6}$)alkylamino, di(C$_{1-6}$)alkylamino, cyano, amidino, guanidino, carboxyalkoxy, trifluoromethoxy or perfluoroethoxy.

6. A compound of claim 1, wherein Y is one of —O— or —NR$^{10}$—, and R$^{10}$ in each instance is one of hydrogen, C$_{1-6}$alkyl, benzyl, phenethyl, C$_{2-10}$hydroxyalkyl or C$_{2-7}$carboxylalkyl.

7. A compound of claim 1, wherein R$^a$, R$^b$ and R$^c$ are hydrogen.

8. A compound of claim 1, wherein R$^7$ and R$^8$ are independently hydrogen, C$_{1-6}$alkyl, C$_{6-10}$ar(C$_{1-6}$)alkyl, C$_{6-10}$aryl, C$_{2-10}$hydroxyalkyl or C$_{2-7}$carboxylalkyl.

9. A compound of claim 1, wherein $R^7$ and $R^8$ are taken together to form —($CH_2$)$_y$—, and y is 0, 1 or 2.

10. A compound of claim 1, wherein n is from 1 to 4.

11. A compound of claim 1, wherein:

$R^1$ is one of $C_{6-10}$ aryl, pyridinyl, quinizolinyl, quinolinyl or tetrahydroquinolinyl, any of which is optionally substituted by one or two of hydroxy, nitro, trifluoromethyl, halogen, $C_{1-6}$ alkyl, $C_{1-6}$ alkoxy, $C_{1-6}$ aminoalkyl, $C_{1-6}$ aminoalkoxy, amino, mono($C_{1-4}$)alkylamino, di($C_{1-4}$)alkylamino, $C_{2-6}$ alkoxycarbonylamino, $C_{2-6}$ alkoxycarbonyl, carboxy, $C_{1-6}$ hydroxyalkyl, $C_{2-6}$ hydroxyalkoxy, $C_{2-10}$ mono(carboxylalkyl)amino, di($C_{2-10}$ carboxylalkyl)amino, $C_{6-14}$ ar($C_{1-6}$) alkoxycarbonyl, $C_{2-6}$ alkynylcarbonyl, $C_{1-6}$ alkylsulfonyl, $C_{2-6}$ alkenylsulfonyl, $C_{2-6}$ alkynylsulfonyl, $C_{1-6}$ alkylsulfinyl, $C_{1-6}$ alkylsulfonamido, amidino, guanidino, $C_{1-6}$ alkyliminoamino, formyliminoamino, $C_{2-6}$ carboxyalkoxy, $C_{2-6}$ carboxylalkyl, carboxyalkylamino, cyano, trifluoromethoxy, and perfluoroethoxy;

Z is one of —$SO_2O$—, —$SO_2NR^{10}$—, —C($R^yR^z$)O— or —OC($R^yR^z$)—, where $R^y$ and $R^z$ are each hydrogen;

$R^2$, $R^3$ and $R^4$ are independently one of hydrogen, $C_{1-6}$ alkyl, $C_{3-8}$ cycloalkyl, phenyl, benzyl, trifluoromethyl, halogen, hydroxy($C_{1-8}$)alkyl, cyano, nitro, carboxamido, carboxy, $C_{1-4}$ alkoxycarbonyl, $C_{1-4}$ alkoxymethyl or $C_{1-4}$ alkoxy; or alternatively, $R^2$ and $R^3$, when present on adjacent carbon atoms, may also be taken together to form one of —CH=CH—CH=CH— or —($CH_2$)$_q$—, where q is from 2 to 6, and $R^4$ is as defined above;

Y is one of —O—, —S—, —$NR^{10}$—, or a covalent bond;

$R^6$ is one of hydrogen, $C_{1-6}$ alkyl, $C_{6-10}$ ar($C_{1-6}$)alkyl, $C_{6-10}$ aryl, $C_{2-10}$ hydroxyalkyl, $C_{2-10}$ aminoalkyl, mono($C_{1-4}$)alkylamino($C_{2-8}$)alkyl, di($C_{1-4}$)alkylamino($C_{2-8}$)alkyl or $C_{2-10}$ carboxylalkyl;

$R^7$ and $R^8$ are independently one of hydrogen, $C_{1-6}$ alkyl, $C_{2-10}$ carboxylalkyl or $C_{2-10}$ hydroxyalkyl, or $R^7$ and $R^8$ are taken together to form —$CH_2$)$_y$— where y is zero, 1 or 2;

$R^5$, in each instance, is independently hydrogen, $C_{1-6}$ alkyl, benzyl, phenyl, $C_{2-10}$ hydroxyalkyl, $C_{2-10}$ aminoalkyl, $C_{1-4}$ monoalkylamino($C_{2-8}$)alkyl, $C_{1-4}$ dialkylamino($C_{2-8}$)alkyl or $C_{2-10}$ carboxylalkyl;

$R^9$ is one of $C_{1-6}$ alkyl, benzyl, phenyl, $C_{2-10}$ hydroxyalkyl or $C_{2-10}$ carboxylalkyl;

$R^{10}$ is hydrogen, $C_{1-6}$ alkyl, benzyl, phenyl, $C_{1-6}$ alkyloxy($C_{1-6}$)alkyl, wherein said $C_{1-6}$ alkyl or $C_{1-6}$ alkyloxy($C_{1-6}$)alkyl may be substituted by a single amino, $C_{1-4}$ monoalkylamino, di($C_{1-4}$)alkylamino, carboxy, or by one or more hydroxy groups, or $R^{10}$ can form the group —E—P(O)$R^{11}R^{12}$, where E is alkylene, preferably having one to 4 carbon atoms; and $R^{11}$ and $R^{12}$ are independently $C_{1-6}$alkyl groups;

$R^a$, $R^b$ and $R^c$ are each one of hydrogen, $C_{1-4}$ alkyl, hydroxy, $C_{1-4}$ alkoxy, phenoxy, $C_{1-4}$ alkyloxycarbonyl, benzyloxycarbonyl, cyano,

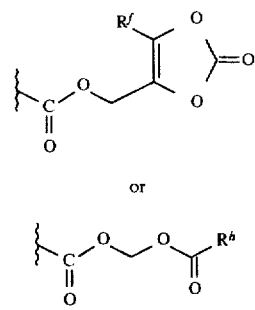

or where $R^h$ is benzyl, methyl, ethyl, isopropyl, sec-butyl or t-butyl, and where $R^f$ is hydrogen or $C_{1-6}$ alkyl;

n is from zero to 8, with the proviso that when W is N, then n is from 2 to 8; and m is from zero to 4, provided that when W is N, then m is not zero.

12. A compound of claim 1 1, wherein:

$R^1$ is one of phenyl-or naphthyl, optionally substituted by one or two of chloro, trifluoromethyl, amino or dimethylamino;

Z is one of -$SO_2O$—, —$SO_2NR^{10}$—, —$CH_2O$— or —$OCH_2$—;

$R^2$ and $R^3$ are each hydrogen or $R^2$ and $R^3$ may also be taken together to form —CH=CH—CH=CH— or —$CH_2$—$CH_2$—$CH_2$—;

$R^4$ is one of hydrogen, methyl, methoxy or trifluoromethyl;

Y is one of —O—, —$NR^{10}$— or a covalent bond, where $R^{10}$ is defined below;

$R^7$ and $R^8$ are independently one of hydrogen, $C_{1-6}$ alkyl, $C_{2-10}$ hydroxyalkyl or $C_{2-10}$ carboxylalkyl, or $R^7$ and $R^8$ are taken together to form —($CH_2$)$_y$—, where y is zero, 1 or 2;

$R^{10}$ is independently hydrogen, $C_{1-4}$ alkyl, $C_{2-4}$ hydroxyalkyl, $C_{2-4}$ carboxylalkyl, $C_{2-4}$ aminoalkyl, dimethylamino($C_{2-8}$)alkyl, methylamino($C_{2-8}$)alkyl;

$R^a$, $R^b$ and $R^c$ are hydrogen, hydroxy,

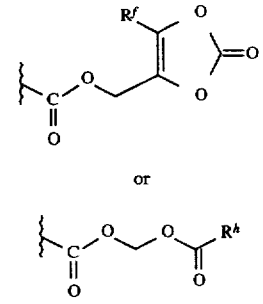

or where $R^h$ is benzyl or t-butyl, and where $R^f$ is hydrogen or methyl;

n is from zero to 4; and m is zero, 1, 2 or 3.

13. A compound of claim 1, which is one of 2-chlorobenzenesulfonic acid 3-[[1-(aminoiminomethyl)piperidin-4-yl]methoxy]phenyl ester, 2-chlorobenzenesulfonic acid 3-[[1-(aminoiminomethyl)piperidin-3-yl]methoxy]phenyl ester, 2-chlorobenzenesulfonic acid 3-[[1-(aminoiminomethyl)piperidin-4-yl]methoxy]-5-methylphenyl ester, 2-chlorobenzenesulfonic acid 3-[[1-(aminoiminomethyl) piperidin-3-yl]methoxy]-5-methylphenyl ester, 2-chlorobenzenesulfonic acid 3-[[1-(aminoiminomethyl) piperidin-4-yl]methoxy]-5-carbomethoxyphenyl ester, 3-(2-chlorobenzyloxy)-5-[[(1-aminoiminomethyl)piperidin-4-yl]methoxy]toluene acetic acid salt, N-benzyl-N-[[3-(1-aminoiminomethyl)piperidin-4-ylmethylamino]phenyl] benzenesulfonamide, 2-chlorobenzenesulfonic acid 3-[[1-aminoiminomethyl) piperidin-4-yl]methoxy]-4-benzylphenyl ester acetic acid salt, 1-naphthalenesulfonic acid 3-[[1-(aminoiminomethyl) piperidin-4-yl]methoxy]-5-methylphenyl ester acetic acid salt, 3-trifluoromethylbenzenesulfonic acid 3-[[1-(aminoiminomethyl)piperidin-4-yl]methoxy]-5-methylphenyl ester acetic acid salt, benzenesulfonic acid 3-[[1-(aminoiminomethyl) piperidin-4-yl]methoxy]-5-methylphenyl ester acetic acid salt, 3-chlorobenzenesulfonic acid 3-[[1-(aminoiminomethyl) piperidin-4-yl)methoxy]-5-methylphenyl ester acetic acid salt, 2-chlorobenzenesulfonic acid 3-[[1-(aminoiminomethyl) piperidin-4-yl]methoxy]-5-methoxyphenyl ester, 2-chlorobenzenesulfonic acid 3-[[1-(aminoiminomethyl) piperidin-4-yl]methoxy]-4-ethoxycarbonyl-5-methylphenyl ester hydrochloride, 2-trifluoromethylbenzenesulfonic acid 3-[[1-(aminoiminomethyl)piperidin-4-yl]methoxy]-5-methylphenyl ester acetic acid salt, 3-methylbenzenesulfonic acid 3-[[1-(aminoiminomethyl) piperidin-4-yl]methoxy]-5-methylphenyl ester acetic acid salt, 2-chlorobenzenesulfonic acid 3-[[1-aminoiminomethyl) piperidin-4 -yl]methoxy]-5-ethylphenyl ester hydrochloride, 2,3-dichlorobenzenesulfonic acid 3-[[1-(aminoiminomethyl)piperidin-4-yl]methoxy]-5-methylphenyl ester hydrochloride, 2-chlorobenzenesulfonic acid 3-[[1-(aminoiminomethyl) piperidin-4-yl] methoxy]naphthalen-1-yl ester hydrochloride, 2-chlorobenzenesulfonic acid 3-[[1-(aminoiminomethyl) piperidin-4-yl]methoxy]-5-hydroxymethylphenyl ester, 2-{(2-chlorobenzenesulfonyl)-[3-[[1-(aminoiminomethyl)piperidin-4-yl]methoxy]-5-[trifluoromethyl]phenyl]amino}acetic acid hydrochloride, 2-{benzenesulfonyl-[3-[[1-(aminoiminomethyl) piperidin-4-yl]methoxy]-5-[trifluoromethyl]phenyl] amino}acetic acid hydrochloride, 2-chloro-N-{3-[[1-(aminoiminomethyl)piperidin-4-yl] methoxy]-5-[trifluoromethyl] phenyl}benzenesulfonamide hydrochloride, or N-benzyl-N-[[3-(1-aminoiminomethyl)-piperidin-4-ylmethyl]-carboxymethyl]amino]phenyl}-2-chlorobenzenesulfonamide.

14. A compound of claim 1, which is one of:
2-chlorobenzenesulfonic acid 3-[2-[1-(aminoiminomethyl)piperazin-4-yl]-ethoxy]phenyl ester diacetic acid salt, or 2-chlorobenzenesulfonic acid 3-[2-[1-(aminoiminomethyl)piperazin-4-yl]ethoxy]-5-methylphenyl ester diacetic acid salt.

15. A compound of claim 1, which is one of:
N-methyl-N-[2-[(4-aminoiminomethylamino)butyloxy]-4-methylphenyl]-benzenesulfonamide, acetic acid salt, 2-chlorobenzenesulfonic acid 3-[3-(aminoiminomethyl) amino]propoxy]-5-methylphenyl ester acetic acid salt, 2-chlorobenzenesulfonic acid 3-[[4-(aminoiminomethyl) amino]butoxy]-5-methylphenyl ester acetic acid salt, or 2-chlorobenzenesulfonic acid 3-[[5-(aminoiminomethyl) amino]pentoxy]-5-methylphenyl ester hydrochloride.

16. A compound of claim 1, which is one of:
3-methoxybenzenesulfonic acid 3-[[1-(aminoiminomethyl)piperidin-4-yl]methoxy]-5-methylphenyl ester hydrochloride;

3-[(carboxy)methoxy]benzenesulfonic acid 3-[[1-(aminoiminomethyl)piperidin-4-yl]methoxy]-5-methylphenyl ester;

3-hydroxybenzenesulfonic acid 3-[[1-(aminoiminomethyl)piperidin-4-yl]methoxy]-5-methylphenyl ester hydrochloride;

3-(2'-hydroxyethoxy)benzenesulfonic acid 3-[[1-(aminoiminomethyl)piperidine-4-yl]methoxy]-5-methylphenyl ester hydrochloride;

3-(2',3'-dihydroxypropoxy)benzenesulfonic acid 3-[[1-(aminoiminomethyl)piperidin-4-yl]methoxy]-5-methylphenyl ester hydrochloride;

2-chlorobenzenesulfonic acid 3-[[1-(aminoiminomethyl) piperidin-4-yl]methoxy]-5-chlorophenyl ester hydrochloride;

3-nitrobenzenesulfonic acid 3-[[1-(aminoiminomethyl]) piperidin-4-yl]methoxy]-5-methylphenyl ester hydrochloride;

3-aminobenzenesulfonic acid 3-[[1-(aminoiminomethyl) piperidin-4-yl]methoxy]-5-methylphenyl ester hydrochloride;

2-methoxycarbonylbenzenesulfonic acid 3-[[1-(aminoiminomethyl)piperidin-4-yl]methoxy]-5-methylphenyl ester hydrochloride;

4-nitrobenzenesulfonic acid 3-[[1-(aminoiminomethyl) piperidin-4-yl]methoxy]-5-methylphenyl ester hydrochloride;

4-aminobenzenesulfonic acid 3-[[1-(aminoiminomethyl) piperidin-4-yl]methoxy]-5-methylphenyl ester hydrochloride;

2-nitrobenzenesulfonic acid 3-[[1-(aminoiminomethyl) piperidin-4-yl]methoxy]-5-methylphenyl ester hydrochloride;

2-aminobenzenesulfonic acid 3-[[1-(aminoiminomethyl) piperidin-4-yl]methoxy]-5-methylphenyl ester hydrochloride;

2-chloro-3-nitrobenzenesulfonic acid 3-[[1-(aminoiminomethyl)piperidin-4-yl]methoxy]-5-methylphenyl ester hydrochloride;

3-amino-2-chlorobenzenesulfonic acid 3-[[1-(aminoiminomethyl)piperidin-4-yl]methoxy]-5-methylphenyl ester dihydrochloride;

2-chlorobenzenesulfonic acid 5-[[1 -(aminoiminomethyl) piperidin-4-yl]methoxy]-2-(ethoxycarbonyl)-3-methylphenyl ester hydrochloride;

2-chlorobenzenesulfonic acid 1-[[1-(aminoiminomethyl) piperidin-4-yl]methoxy]naphthalen-3-yl ester acetic acid salt;

79

3-(2-chlorobenzyloxy)-1-[[(1-aminoiminomethyl) piperidin-4-yl]methoxy]benzene acetic acid salt;

6-((2-chlorobenzenesulfonyl)-{3-[[(1-aminoiminomethyl)piperidin-4-yl]methoxy]-5-methylphenyl}amino)hexanoic acid methyl ester hydrochloride;

6-((2-chlorobenzenesulfonyl)-{3-[[(1-aminoiminomethyl)piperidin-4-yl]methoxy]-5-methylphenyl}amino)hexanoic acid hydrochloride;

6-((2-chlorobenzenesulfonyl)-{3-[[(1-aminoiminomethyl)piperidin-4-yl]methoxy]-5-(trifluoromethyl)phenyl}amino)hexanoic acid;

N-(2-propyl)-N-{[3-(1-aminoiminomethyl)piperidin-4-ylmethoxy]-5-trifluoromethyl}phenyl-2-chlorobenzenesulfonamide hydrochloride;

2-chlorobenzenesulfonic acid 3-[[1-(N-methoxycarbonyl-aminoiminomethyl)piperidin-4-yl]methoxy]-5-methylphenyl ester;

2-chloro-3-nitrobenzenesulfonic acid 3-[[1-((N-methoxycarbonylamino)-N-methoxy-carbonyliminomethyl)piperidin-4-yl]methoxy]-5-methylphenyl ester;

2-chloro-3-nitrobenzenesulfonic acid 3-[[1-((N,N-di(methoxycarbonyl)-amino)-N-methoxycarbonyliminomethyl)piperidin-4-yl]methoxy]-5-methylphenyl ester; and 2-chlorobenzenesulfonic acid 3-{N-[[3-(aminoiminomethyl)amino]propyl]-N-(methyl) aminomethyl}phenyl ester acetic acid salt.

17. A compound of claim 1, having the formula:

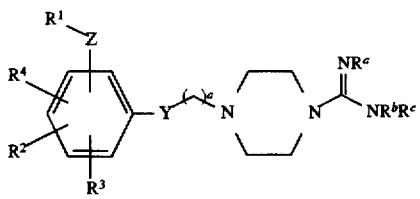

II or a solvate, a hydrate or a pharmaceutically acceptable salt thereof; wherein:

$R^1$, Z, $R^2$, $R^3$, $R^4$, Y, $R^a$, $R^b$ and $R^c$ are defined in claim 1; and a is from 1 to 8, provided that when Y is other than —$CR^5R^9$—, then a is from 2 to 8.

18. A compound of claim 1, having the formula:

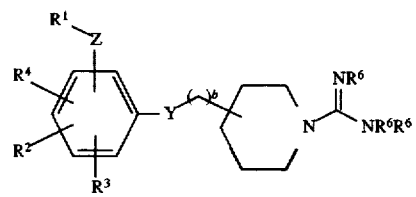

III or a solvate, a hydrate or a pharmaceutically acceptable salt thereof; wherein:

$R^1$, Z, $R^2$, $R^3$, $R^4$, Y, $R^a$, $R^b$ and RC are defined in claim 1; and b is from 1 to 8.

80

19. A compound of claim 1, having the formula:

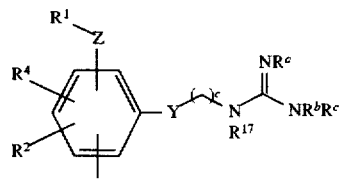

IV or solvates, hydrates or pharmaceutically acceptable salts thereof; wherein:

$R^1$, Z, $R^2$, $R^3$, $R^4$, Y, $R^a$, $R^b$ and RC are defined in claim 1;

$R^{17}$ is one of hydrogen, alkyl, aralkyl, aryl, $C_{2-10}$hydroxyalkyl or carboxylalkyl; and c is from 1 to 14, provided that when Y is other than —$CR^5R^9$—, then c is from 2-14.

20. A compound of claim 1, having the formula:

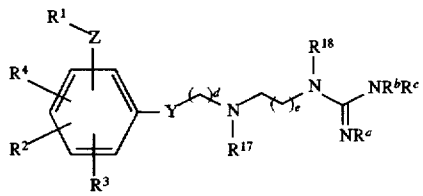

V or solvates, hydrates or pharmaceutically acceptable salts thereof; wherein:

$R^1$, Z, $R^2$, $R^3$, $R^4$, Y, $R^a$, $R^b$ and $R^c$ are defined in claim 1;

$R^{17}$ and $R^{18}$ are each independently one of hydrogen, alkyl, aralkyl, aryl, $C_{2-10}$hydroxyalkyl or carboxylalkyl;

d is from 1 to 8; with the proviso that when Y is other than —$CR^5R^9$— then d is from 2 to 8; and e is from 1 to 4.

21. A compound of any of claims 17, 18, 19 or 20, wherein:

R is one of $C_{1-612}$alkyl, cycloalkyl aryl, aralkyl or heteroaryl, any of which may be optionally substituted by one or more of hydroxy, nitro, trifluoromethyl, halogen, alkoxy, cyano, amino, monoalkylamino, dialkylamino, carboxyalkoxy, mono(carboxylalkyl) amino, di(carboxylalkyl)amino, amidino, guanidino, ditrifluoromethoxy or perfluoroethoxy, and wherein said aryl, cycloalkyl and aralkyl may further be optionally substituted by one or more alkyl moieties;

Z is one of —$NR^{10}SO_2$—, —$SO_2NR^{10}$—, —$NR^{10}CH_2$—, —$CH_2NR^{10}$—, —OSO—, —$SO_2O$—, —$OCH_2$— or —$CH_2O$—;

$R^2$, $R^3$ and $R^4$ are each independently one of hydrogen, alkyl, cycloalkyl, aryl, aralkyl, heteroaryl, trifluoromethyl, halogen, hydroxyalkyl, cyano, nitro, carboxamide, —$CO_2R^x$, —$CH_2OR^x$ or —$OR^x$, or when present on adjacent carbon atoms, $R^2$ and $R^3$ may also be taken together to form one of —CH=CH—CH=CH— or —$(CH_2)_q$—, where q is from 2 to 6, and $R^4$ is defined as above;

$R^x$, in each instance, is independently one of hydrogen, alkyl or cycloalkyl wherein said alkyl or cycloalkyl groups may optionally have one or more unsaturations;

Y is one of —O—, —$NR^{10}$—, —S—, —$CR^5R^9$— or a covalent bond;

$R^9$ is one of alkyl, aralkyl, aryl, hydroxyalkyl or carboxylalkyl;

$R^5$ and $R^{10}$, in each instance, is independently one of hydrogen, alkyl, aralkyl, aryl, $C_{2-10}$hydroxyalkyl or carboxylalkyl; and $R^a$, $R^b$ and $R^c$ are independently hydrogen, alkyl, cyano or —$CO_2R^y$, where $R^y$ is alkyl or cycloalkyl.

22. A compound of any of claims 17, 18, 19 or 20, wherein:

$R^1$ is one of $C_{6-10}$ aryl, pyridinyl, quinazolinyl, quinolinyl or tetrahydroquinolinyl, any of which is optionally substituted by one or two of hydroxy, nitro, trifluoromethyl, halogen, $C_{1-6}$ alkyl, $C_{1-6}$ alkoxy, $C_{1-6}$ aminoalkyl, $C_{1-6}$ aminoalkoxy, amino, mono($C_{1-4}$) alkylamino, di($C_{1-4}$)alkylamino, $C_{2-6}$ alkoxycarbonylamino, $C_{2-6}$ alkoxycarbonyl, carboxy, $C_{1-6}$ hydroxyalkyl, $C_{2-6}$ hydroxyalkoxy, $C_{2-10}$ mono (carboxylalkyl)amino, di($C_{2-10}$ carboxylalkyl)amino, $C_{6-14}$ ar($C_{1-6}$) alkoxycarbonyl, $C_{2-6}$ alkynylcarbonyl, $C_{1-6}$ alkylsulfonyl, $C_{2-6}$ alkenylsulfonyl, $C_{2-6}$ alkynylsulfonyl, $C_{1-6}$ alkylsulfinyl, $C_{1-6}$ alkylsulfonamido, amidino, guanidino, $C_{1-6}$ alkyliminoamino, formyliminoamino, $C_{2-6}$ carboxyalkoxy, $C_{2-6}$ carboxylalkyl, carboxyalkylamino, cyano, trifluoromethoxy, and perfluoroethoxy;

Z is one of—$SO_2O$—, —$SO_2NR^{10}$—, —$C(R^yR^z)O$— or —$OC(R^yR^z)$—, where $R^y$ and $R^z$ are each hydrogen;

$R^2$, $R^3$ and $R^4$ are independently one of hydrogen, $C_{1-6}$ alkyl, $C_{3-8}$ cycloalkyl, phenyl, benzyl, trifluoromethyl, halogen, hydroxy($C_{1-8}$)alkyl, cyano, nitro, carboxamido, carboxy, $C_{1-4}$ alkoxycarbonyl, $C_{1-4}$ alkoxymethyl or $C_{1-4}$ alkoxy; or alternatively, $R^2$ and $R^3$, when present on adjacent carbon atoms, may also be taken together to form one of —CH=CH—CH=CH— or —$(CH_2)_q$—, where q is from 2 to 6, and $R^4$ is as defined above;

Y is one of —O—, —S—, —$NR^{10}$—, or a covalent bond;

$R^5$, in each instance, is independently hydrogen, $C_{1-6}$ alkyl, benzyl, phenyl, $C_{2-10}$ hydroxyalkyl, $C_{2-10}$ aminoalkyl, $C_{1-4}$ monoalkylamino($C_{2-8}$)alkyl, $C_{1-4}$ dialkylamino($C_{2-8}$)alkyl or $C_{2-10}$ carboxylalkyl;

$R^9$ is one of $C_{1-6}$ alkyl, benzyl, phenyl, $C_{2-10}$ hydroxyalkyl or $C_{2-10}$ carboxylalkyl;

$R^{10}$ is hydrogen, $C_{1-6}$ alkyl, benzyl, phenyl, $C_{1-6}$ alkyloxy ($C_{1-6}$)alkyl, wherein said $C_{1-6}$ alkyl or $C_{1-6}$ alkyloxy ($C_{1-6}$)alkyl may be substituted by a single amino, $C_{1-4}$ monoalkylamino, di($C_{1-4}$)alkylamino, carboxy, or by one or more hydroxy groups, or $R^{10}$ can form the group —E—$P(O)R^{11}R^{12}$, where E is alkylene, preferably having one to 4 carbon atoms; and $R^{11}$ and $R^{12}$ are independently $C_{1-6}$alkyl groups; and $R^a$, $R^b$ and $R^c$ are each one of hydrogen, $C_{1-4}$ alkyl, hydroxy, $C_{1-4}$ alkoxy, phenoxy, $C_{1-4}$ alkyloxycarbonyl, benzyloxycarbonyl, cyano,

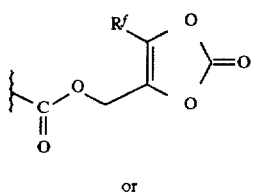

or

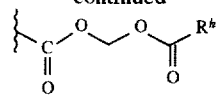

where $R^h$ is benzyl, methyl, ethyl, isopropyl, sec-butyl or t-butyl, and where $R^f$ is hydrogen or $C_{1-6}$ alkyl.

23. A compound of claim 22, wherein:

$R^1$ is one of phenyl or naphthyl, optionally substituted by one or two of chloro, trifluoromethyl, amino or dimethylamino;

Z is one of —$SO_2O$—, —$SO_2NR^{10}$—, —$CH_2O$— or —$OCH_2$—;

$R^2$ and $R^3$ are each hydrogen or $R^2$ and $R^3$ may also be taken together to form —CH=CH—CH=CH— or —$CH_2$—$CH_2$—$CH_2$—;

$R^4$ is one of hydrogen, methyl, methoxy or trifluoromethyl;

Y is one of —O—, —$NR^{10}$— or a covalent bond, where $R^{10}$ is defined below;

$R^{10}$ is independently hydrogen, $C_{1-4}$ alkyl, $C_{2-4}$ hydroxyalkyl, $C_{2-4}$ carboxylalkyl, $C_{2-4}$ aminoalkyl, dimethylamino($C_{2-8}$)alkyl, methylamino($C_{2-8}$)alkyl; and $R^a$, $R^b$ and $R^c$ are hydrogen, hydroxy,

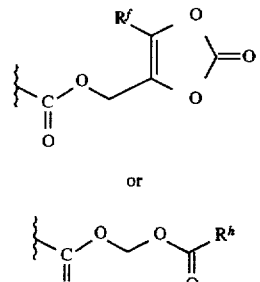

where $R^h$ is benzyl or t-butyl, and where $R^f$ is hydrogen or methyl.

24. A compound of any of claims 17, 18, 19 or 20, wherein Z is one of —$SO_2NR^{10}$—, —$SO_2O$— or —$CH_2O$—.

25. A compound of any of claims 17, 18, 19 or 20, wherein $R^1$ is one of $C_{4-7}$cycloalkyl or $C_{6-12}$aryl, either of which is optionally substituted by one or more of hydroxy, nitro, trifluoromethyl, halogen, $C_{1-6}$alkoxy, $C_{1-6}$alkyl, amino, mono($C_{1-6}$)alkylamino, di($C_{1-6}$)alkylamino, amidino, guanidino, cyano, carboxyalkyloxy, trifluoromethoxy or perfluoroethoxy.

26. A compound of any of claims 17, 18, 19 or 20, wherein $R^1$ is heteroaryl, optionally substituted by one or more of hydroxy, nitro, trifluoromethyl, halogen, $C_{1-6}$-alkoxy, $C_{1-6}$-alkyl, amino, mono($C_{1-6}$)alkylamino, di($C_{1-6}$)alkylamino, amidino, guanidino, cyano, carboxyalkyloxy, trifluoromethoxy or perfluoroethoxy.

27. A compound of any of claims 17, 18, 19 or 20, wherein Y is one of —O— or —$NR^{10}$—, and $R^{10}$ in each instance is one of hydrogen, $C_{1-6}$alkyl, benzyl, phenethyl, $C_{2-10}$hydroxyalkyl or $C_{2-7}$carboxylalkyl.

28. A compound of claim 20, wherein d is 2, 3 or 4, and e is 1 or 2.

29. A compound of any of claims 17, 18, 19 or 20, wherein $R^a$, $R^b$ and $R^c$ are hydrogen.

30. A pharmaceutical composition for inhibiting proteolysis in a mammal, comprising an amount of a compound of claim 1 effective to inhibit proteolysis, and a pharmaceutically acceptable carrier or diluent.

31. A pharmaceutical composition for inhibiting proteolysis in a mammal, comprising an amount of a compound of claim 11 effective to inhibit proteolysis, and a pharmaceutically acceptable carrier or diluent.

32. A pharmaceutical composition for inhibiting proteolysis in a mammal, comprising an amount of a compound of claim 12 effective to inhibit proteolysis, and a pharmaceutically acceptable carrier or diluent.

33. A pharmaceutical composition for inhibiting proteolysis in a mammal, comprising an amount of a compound of any one of claims 13, 14, 15 or 16 effective to inhibit proteolysis, and a pharmaceutically acceptable carrier or diluent.

34. A pharmaceutical composition for inhibiting proteolysis in a mammal, comprising an amount of a compound of any one of claims 17, 18, 19 or 20 effective to inhibit proteolysis, and a pharmaceutically acceptable carrier or diluent.

35. A method of inhibiting proteolysis in a mammal, comprising administering to the mammal a composition of claim 30.

36. A method of treating pancreatitis, thrombosis, ischemia, stroke, restenosis, emphysema or inflammation in a mammal, comprising administering to the mammal a composition of claim 30.

37. A method of inhibiting thrombin-induced platelet aggregation and clotting of fibrinogen in plasma, comprising administering to the mammal a composition of claim 30.

38. A method of inhibiting proteolysis in a mammal, comprising administering to the mammal a composition of claim 31.

39. A method of treating pancreatitis, thrombosis, ischemia, stroke, restenosis, emphysema or inflammation in a mammal, comprising administering to the mammal a composition of claim 31.

40. A method of inhibiting thrombin-inducet platelet aggregation and clotting of fibrinogen in plasma, comprising administering to the mammal a composition of claim 31.

41. A method of inhibiting proteolysis in a mammal, comprising administering to the mammal a composition of claim 32.

42. A method of treating pancreatitis, thrombosis, ischemia, stroke, restenosis, emphysema or inflammation in a mammal, comprising administering to the mammal a composition of claim 32.

43. A method of inhibiting thrombin-induced platelet aggregation and clotting of fibrinogen in plasma, comprising administering to the mammal a composition of claim 32.

44. A method of inhibiting proteolysis in a mammal, comprising administering to the mammal a composition of claim 33.

45. A method of treating pancreatitis, thrombosis, ischemia, stroke, restenosis, emphysema or inflammation in a mammal, comprising administering to the mammal a composition of claim 33.

46. A method of inhibiting thrombin-induced platelet aggregation and clotting of fibrinogen in plasma, comprising administering to the mammal a composition of claim 33.

47. A method of inhibiting proteolysis in a mammal, comprising administering to the mammal a composition of claim 34.

48. A method of treating pancreatitis, thrombosis, ischemia, stroke, restenosis, emphysema or inflammation in a mammal, comprising administering to the mammal a composition of claim 34.

49. A method of inhibiting thrombin-induced platelet aggregation and clotting of fibrinogen in plasma, comprising administering to the mammal a composition of claim 34.

* * * * *

UNITED STATES PATENT AND TRADEMARK OFFICE
CERTIFICATE OF CORRECTION

Page 1 of 2

PATENT NO. : 5,792,769

DATED : August 11, 1998

INVENTORS : Lu et al.

It is certified that an error appears in the above-identified patent and that said Letters Patent is hereby corrected as shown below.

At column 72, line 67, in claim 1, delete "—$SO_2O$" and insert therein -- —$SO_2O$— --.

At column 73, line 24, in claim 1, delete "—$CH_2)_y$—" and insert therein

-- —$(CH_2)_y$— --.

At column 73, line 46, in claim 1, delete the second occurrence of "aryloxy" and insert therein --aralkoxy--.

At column 74, line 15, in claim 2, delete "—ORx," and insert therein --$OR^x$,--.

At column 74, line 45, in claim 3, delete "—$CH_{2/O}$—" and insert therein -- —$CH_2O$ At column 75, line 2, in claim 9, delete "—$CH_2)_y$—" and insert therein -- —$(CH_2)$ At column 75, line 5, in claim 11, please delete "quinizolinyl" and insert therein --quinazolinyl--.

At column 75, line 46, in claim 11, please delete "—$CH_2)_y$—" and insert therein -- —$(CH_2)_y$— --.

At column 79, line 66, in claim 18, delete "RC" and insert therein --$R^C$--.

At column 80, line 13, in claim 19, delete "RC" and insert therein --$R^C$--.

At column 80, line 41, in claim 21, delete "R" and insert therein --$R^1$--.

UNITED STATES PATENT AND TRADEMARK OFFICE
CERTIFICATE OF CORRECTION

PATENT NO. : 5,792,769

DATED : August 11, 1998

INVENTORS : Lu et al.

It is certified that an error appears in the above-identified patent and that said Letters Patent is hereby corrected as shown below.

At column 80, line 41, in claim 21, delete "$C_{1-612}$" and insert therein --$C_{6-12}$--.

At column 80, line 51, in claim 21, please delete "—OSO—" and insert therein -- —$OSO_2$— --.

At column 81, line 49, in claim 22, please delete "$C_{,1-4}$" and insert therein --$C_{1-4}$--.

At column 84, line 1, in claim 40, please delete "inducet" and insert therein --induced--.

Signed and Sealed this

Twenty-sixth Day of January, 1999

Attest:

Attesting Officer

*Acting Commissioner of Patents and Trademarks*